United States Patent [19]
McMurry et al.

[11] Patent Number: 6,096,724
[45] Date of Patent: Aug. 1, 2000

[54] PYRIMIDINE DERIVATIVES AND GUANINE DERIVATIVES, AND THEIR USE IN TREATING TUMOR CELLS

[75] Inventors: Thomas Brian Hamilton McMurry; Robert Stanley McElhinney; Joan Elizabeth McCormick; Dorothy Josephine Donnelly; Paul Murray; Christophe Carola, all of Dublin 2, Ireland; Rhoderick Hugh Elder, Manchester, United Kingdom; Jane Kelly, Manchester, United Kingdom; Geoffrey Paul Margison, Manchester, United Kingdom; Amanda Jean Watson, Manchester, United Kingdom; Joseph Anthony Rafferty, Manchester, United Kingdom; Mark Andrew Willington, Manchester, United Kingdom; Mark Ross Middleton, Manchester, United Kingdom

[73] Assignee: Cancer Research Campaign Technology Limited, London, United Kingdom

[21] Appl. No.: 09/088,740

[22] Filed: Jun. 2, 1998

Related U.S. Application Data

[63] Continuation-in-part of application No. 08/568,576, Dec. 7, 1995, and a continuation-in-part of application No. 08/572,966, Dec. 15, 1995, Pat. No. 5,929,046, and a continuation-in-part of application No. PCT/IE96/00084, Dec. 9, 1996.

[51] Int. Cl.[7] ............................. A01N 43/04; C07H 19/00
[52] U.S. Cl. ................................ 514/45; 514/46; 514/47; 514/48; 536/27.13; 536/27.2; 536/27.21; 536/27.7; 536/27.8; 536/27.81; 536/28.4; 536/28.54
[58] Field of Search .................................. 514/45, 46, 47, 514/48; 536/27.13, 27.2, 27.21, 27.7, 27.8, 27.81, 28.4, 28.54

[56] References Cited

U.S. PATENT DOCUMENTS

| | | |
|---|---|---|
| 5,091,430 | 2/1992 | Moschel et al. . |
| 5,260,291 | 11/1993 | Lunt et al. . |
| 5,352,669 | 10/1994 | Moschel et al. . |

FOREIGN PATENT DOCUMENTS

| | | |
|---|---|---|
| 0184473 A1 | 6/1996 | European Pat. Off. . |
| 2139107 | 2/1973 | Germany . |
| WO 91/13898 | 9/1991 | WIPO . |
| WO 94/29312 | 12/1994 | WIPO . |
| WO 96/04281 | 2/1996 | WIPO . |

OTHER PUBLICATIONS

Chemical Abstracts, vol. 101, No. 25, Dec. 17, 1984, Columbus, Ohio, US; Abstract No. 230466q, p. 765; column R; XP00208572, see abstract & Heterocycles, vol. 22, No. 8, 1984, pp. 1789–1790, Ram SIYA, et al.

The Journal of Organic Chemistry, vol. 34, No. 7, Jul. 1969, pp. 2160–2163, XP002028568 Morris J. Robins et al., p. 2161, column 2, formula 13.

Journal of Medicinal Chemistry, vol. 38, No. 2, Jan. 20, 1995, pp. 359–365, XP002028569 Mi–Young Chae, et al.

Journal of Medicinal Chemistry, vol. 37, No. 3, Feb. 4, 1994, pp. 342–347, XP002028570 Mi–Young Chae, et al.

Journal of Medicinal Chemistry, vol. 35, No. 23, Nov. 13, 1992, pp. 4486–4491, XP002028571, Robert C. Moschel, et al.

Cancer Research, vol. 46, Sep. 1986, pp. 4500–4504. M. Eileen Dolan, et al.

Cancer Chemotherapy & Pharmacology, 1989, vol. 25, pp. 103–108, M. Eileen Dolan, et al.

Biochemistry, 1993, vol. 32, pp. 11998–12006, A. E. Pegg, et al.

Anti–Cancer Drug Design, 1994, vol. 9, pp. 401–408, C.E. Arris, et al.

Biochemical Pharmacology, 1994, vol. 48, pp. 2127–2134, U.K. Marathi, et al.

Proc. Natl. Acad. Sci. USA, 1990, vol. 87, pp. 5368–5372, M. Eileen Dolan et al.

Cancer Communications, 1990, vol. 2, No. 11, pp. 371–377, M. Eileen Dolan, et al.

Cancer Research, 1994, vol. 54, pp. 5123–5130.

(List continued on next page.)

Primary Examiner—James O. Wilson
Attorney, Agent, or Firm—Smith, Gambrell & Russell, LLP

[57] ABSTRACT

The present invention provides certain 6-hetarylalkyloxy pyrimidine derivatives of formula II

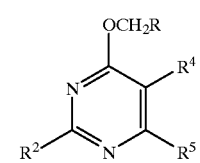

wherein R is (i) a cyclic group having at least one 5- or 6-membered heterocyclic ring, optionally with a carbocyclic or heterocyclic ring fused thereto, the or each heterocyclic ring having at least one hetero atom chosen from O, N, or S, or a substituted derivative thereof; or (ii) phenyl or a substituted derivative thereof, $R^2$ is selected from H, $C_1$–$C_5$ alkyl, halogen or $NH_2$, $R^4$ and $R^5$ which are the same or different are selected from H, $NH_2$ or $NO_n$ where n=1 or 2, or $R^4$ and $R^5$ together with the pyrimidine ring form a 5- or 6-membered ring structure containing one or more heterocyclic atoms, and pharmaceutically acceptable salts thereof, exhibit the ability to deplete $O^6$-alkylguanine-DNA alkyltransferase (ATase) activity.

34 Claims, 35 Drawing Sheets

OTHER PUBLICATIONS

Journal of Medicinal Chemistry, 1977, vol. 20, No. 3, pp. 341–344, Abelardo P. Martinez, et al.

Journal of Medicinal Chemistry, 1975, vol. 18, No. 10, pp. 968–973, Brajeswar Paul, et al.

Tetrahedron Letters, 1985, vol. 26, No. 15, pp. 1815–1818, Malcolm MacCross, et al.

Anti–Cancer Drug Design, 1995, vol. 10, pp. 75–95, J.E.A. Wibley, et al.

Biochemical Pharmacology, 1995, vol. 50, pp. 1141–1148, A.E. Pegg, et al.

Cancer Research, 1995, vol. 55, pp. 4606–4610, S.L. Berg, et al.

Cancer Research, 1995, vol. 55, pp. 2853–2857, M. Eileen Dolan, et al.

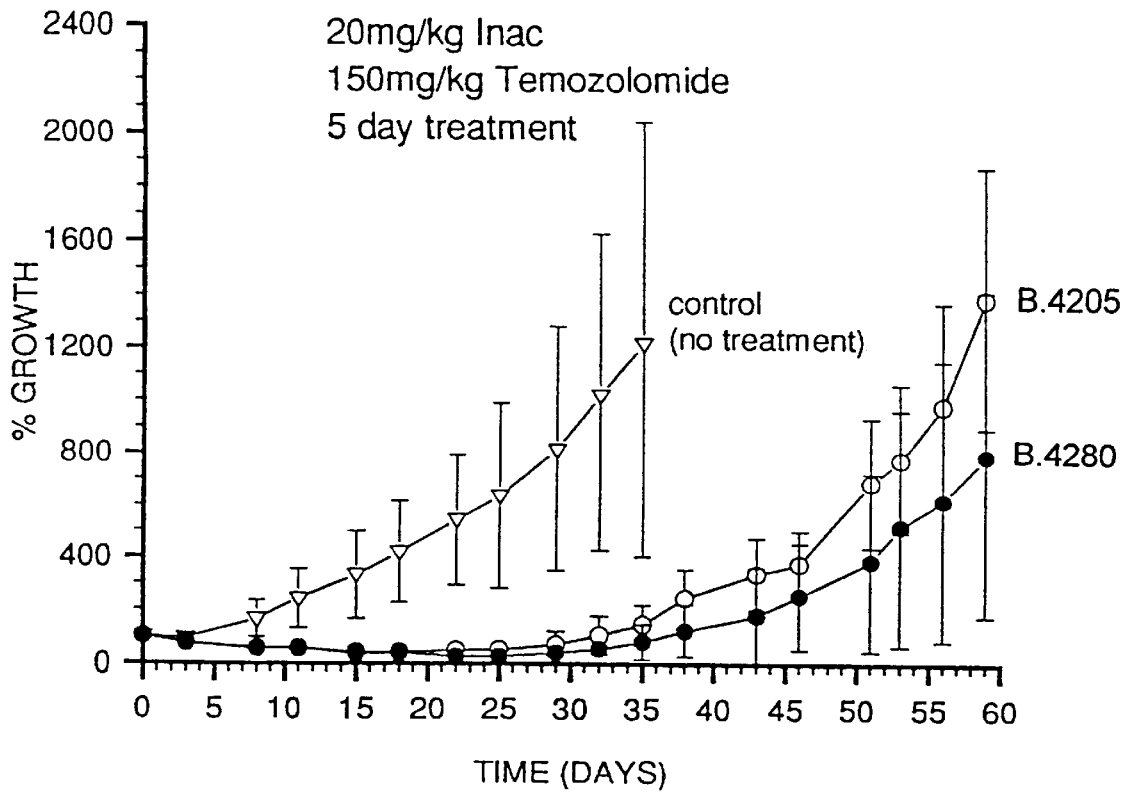
FIG. 24
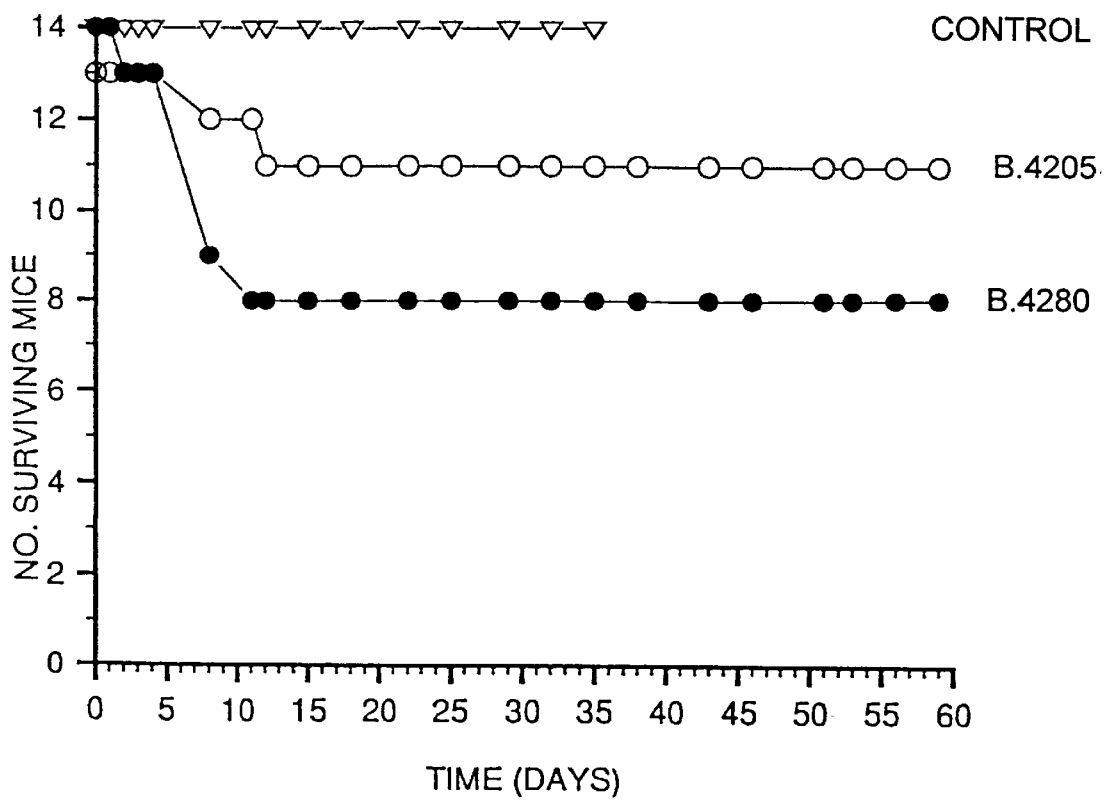

- no treatment (v.c)
- 20mg/kg B4349 only
- 20mg/kg B4351 only
- 100mg/kg Temozolomide only
- 20mg/kg B4349 + 100mg/kg Temozolomide
- 20mg/kg B4351 + 100mg/kg Temozolomide

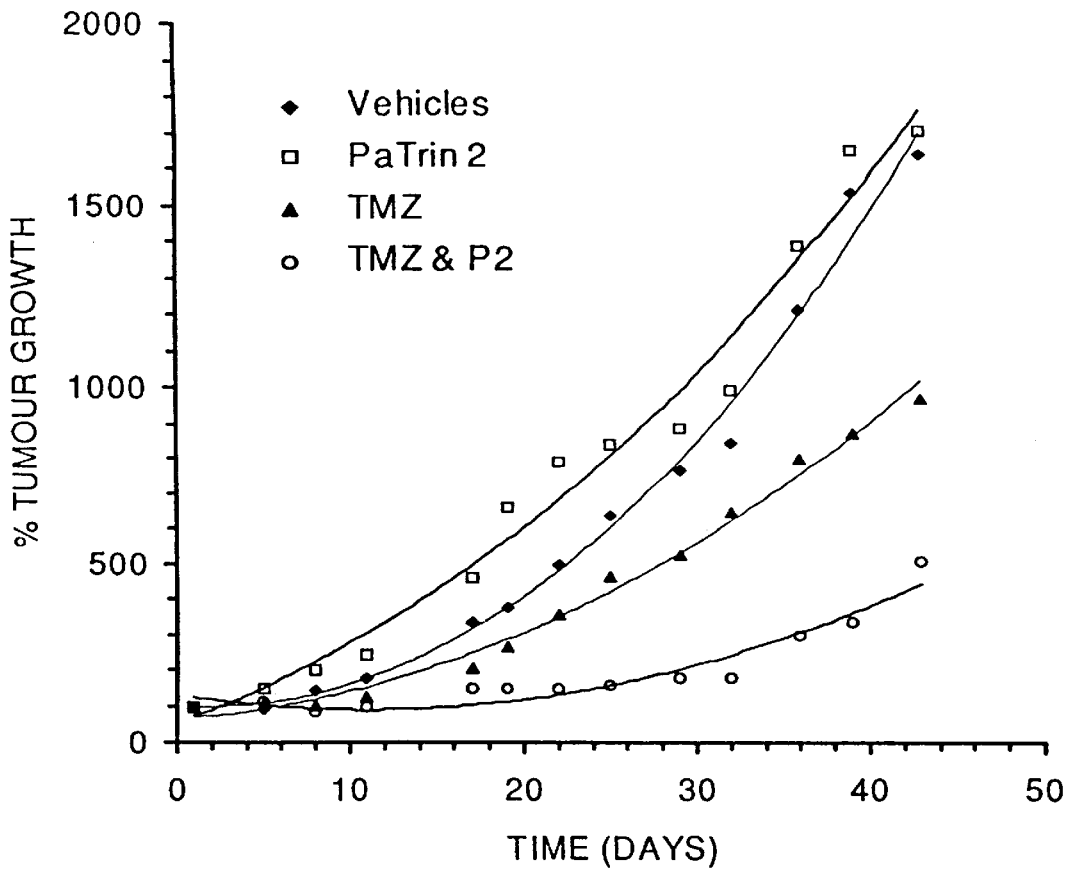
FIG. 27
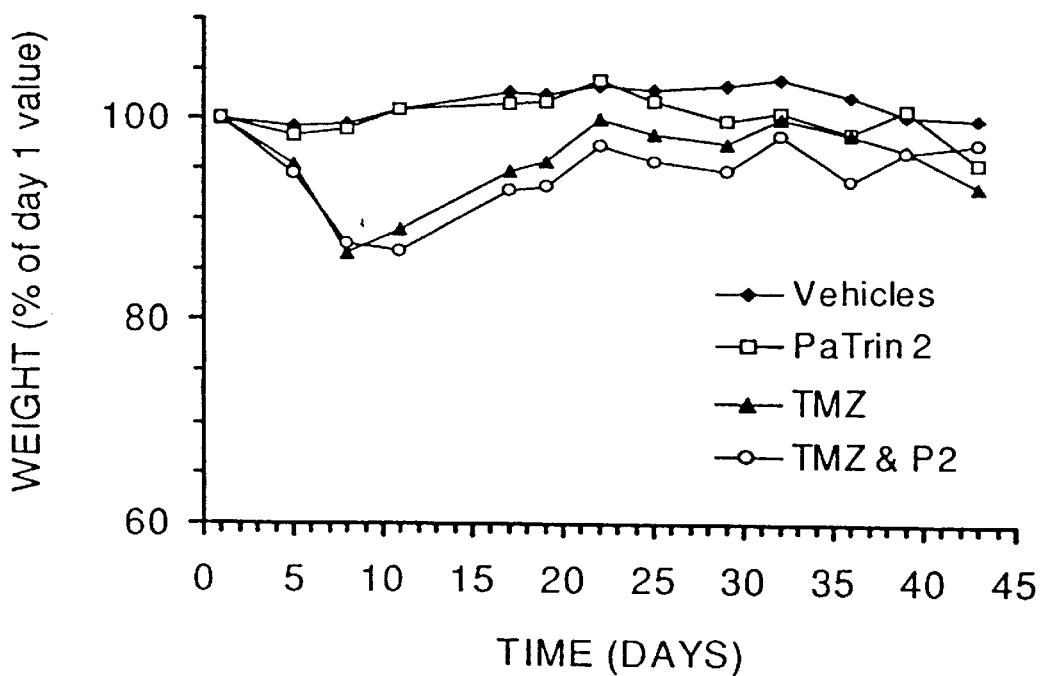

4-BROMO-2-THIOPHENECARBOXALDEHYDE $+ NaB[^3H]_4$

[³H]4-BROMOTHENYLALCOHOL       GUANINE SALT

+NaH

[³H]4-BROMOTHENYLGUANINE

PYRIMIDINE DERIVATIVES AND GUANINE DERIVATIVES, AND THEIR USE IN TREATING TUMOR CELLS

This application is a continuation-in-part of U.S. application Ser. Nos. 08/568,576, filed on Dec. 7, 1995 and 08/572,966, filed on Dec. 15, 1995. This application is also a continuation-in-part of international application PCT/IE96/00084, filed on Dec. 9, 1996.

TECHNICAL FIELD

The present invention relates to pyrimidine derivatives and guanine derivatives, and their use in treating tumour cells. In particular, it relates to 6-hetarylalkyloxy pyrimidine derivatives, $O^6$-substituted guanine derivatives and $S^6$-substituted thioguanine derivatives, these compounds exhibiting the ability to deplete $O^6$-alkylguanine-DNA alkyltransferase (ATase) activity in tumour cells.

BACKGROUND ART

It has been suggested to use $O^6$-alkyl guanine derivatives possessing $O^6$-alkylguanine-DNA alkyltransferase depleting activity in order to enhance the effectiveness of chemotherapeutic alkylating agents, principally those that methylate or chloroethylate DNA, used for killing tumour cells. There is increasing evidence that in mammalian cells the toxic and mutagenic effects of alkylating agents are to a large extent a consequence of alkylation at the $O^6$-position of guanine in DNA. The repair of $O^6$-alkylguanine is mediated by ATase, a repair protein that acts on the $O^6$-alkylated guanine residues by stoichiometric transfer of the alkyl group to a cysteine residue at the active site of the repair protein in an autoinactivating process. The importance of ATase in protecting cells against the biological effects of alkylating agents has been most clearly demonstrated by the transfer and expression of cloned ATase genes or cDNAs into ATase deficient cells: this confers resistance to a variety of agents, principally those that methylate or chloroethylate DNA. Whilst details of the mechanism of cell killing by $O^6$-methylguanine in ATase deficient cells is not yet clear, killing by $O^6$-chloroethylguanine occurs through DNA interstand crosslink formation to a cytosine residue on the opposite strand via a cyclic enthanoguanine intermediate, a process that is prevented by ATase-mediated chloroethyl group removal or complex formation.

The use of $O^6$-methylguanine and $O^6$-n-butylguanine for depleting ATase activity has been investigated (Dolan et al., Cancer Res., (1986) 46, pp. 4500; Dolan et al., Cancer Chemother. Pharmacol., (1989) 25, pp 103. $O^6$-benzylguanine derivatives have been proposed for depleting ATase activity in order to render ATase expressing cells more susceptible to the cytotoxic effects of chloroethylating agents (Moschel et al., J. Med. Chem., 1992, 35, 4486). U.S. Pat. No. 5,091,430 and International Patent Application No. WO 91/13898 Moschel et al. disclose a method for depleting levels of $O^6$-alkylguanine-DNA alkyltransferase in tumour cells in a host which comprises administering to the host an effective amount of a composition containing $O^6$-benzylated guanine derivatives of the following formula:

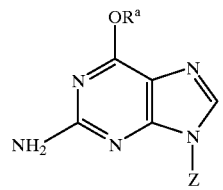

wherein Z is hydrogen, or

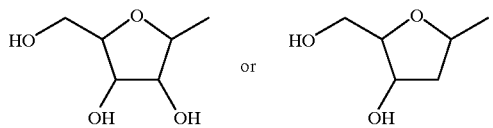

and $R^a$ is a benzyl group or a substituted benzyl group. A benzyl group may be substituted at the ortho, meta or para position with a substituent group such as halogen, nitro, aryl such as phenyl or substituted phenyl, alkyl of 1–4 carbon atoms, alkoxy of 1–4 carbon atoms, alkenyl of up to 4 carbon atoms, alkynyl of up to 4 carbon atoms, amino, monoalkylamino, dialkylamino, trifluoromethyl, hydroxy, hydroxymethyl, and $SO_nR^b$ wherein n is 0, 1, 2 or 3 and $R^b$ is hydrogen, alkyl of 1–4 carbon atoms or aryl. Chae et al., J. Med. Chem., 1994, 37, 342–347 describes tests on $O^6$-benzylguanine analogs bearing increasingly bulky substituent groups on the benzene ring or at position 9. Chae et. al., J. Med. Chem. 1995, 38, 359–365 describe several 8-substituted $O^6$-benzylguanines, 2- and/or 8-substituted 6-(benzyloxy)purines, substituted 6(4)-(benzyloxy) pyrimidines, and a 6-(benzyloxy)-s-triazine which were tested for their ability to inactivate ATase. Two types of compounds were identified as being significantly more effective than $O^6$-benzylguanine at inactivating ATase in human HT29 colon tumour cell extracts. These were 8-substituted $O^6$-benzylguanines bearing electron-withdrawing groups at the 8-position (e.g. 8-aza-$O^6$-benzylguanine and $O^6$-benzyl-8-bromoguanine) and 5-substituted 2,4-diamino-6-(benzyloxy)pyrimidines bearing electron withdrawing groups at the 5-position (e.g. 2,4-diamino-6-(benzyloxy)-5-nitroso- and 2,4-diamino-6-(benzyloxy)-5-nitropyrimidine). The latter derivatives were also more effective than $O^6$-benzylguanine at inactivating ATase in intact HT29 colon tumour cells. WO 96/04280 published after the priority dates of this application concerns similar substituted $O^6$-benzylguanines and 6(4)-benzyloxypyrimidines.

The present Applicants are also Applicants in International Patent Application PCT/IE94/00031 which was published under No. WO 94/29312. U.S. patent application Ser. No. 08/568,576, filed Dec. 7, 1995, is the corresponding application in the United States (the contents of which are incorporated herein by reference in their entirety) described $O^6$-substituted guanine derivatives of formula I:

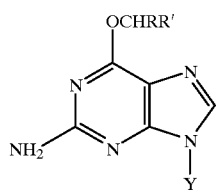 (I)

wherein
Y is H, ribosyl, deoxyribosyl, or

wherein X is O or S, R" and R'" are alkyl, or substituted derivatives thereof;
R' is H, alkyl or hydroxyalkyl;
R is (i) a cyclic group having at least one 5- or 6-membered heterocyclic ring, optionally with a carbocyclic or heterocyclic ring fused thereto, the or each heterocyclic ring having at least one hetero atom chosen from O, N, or S, or a substituted derivative thereof; or
(ii) naphthyl or a substituted derivative thereof;
and pharmaceutically acceptable salts thereof.

In order to be useful for depleting ATase activity and thus enhance the effects of the above-mentioned chemotherapeutic agents, compounds should have combination of characteristics assessed by reference to:
1) In vitro inactivation of recombinant ATase.
2) Stability.
3) Solubility.
4) Inactivation of ATase in mammalian cells and/or tumour xenografts.
5) Sensitization of mammalian cells and/or tumour xenografts to the killing or growth inhibitory effects of the said chemotherapeutic agents.

The behaviour of novel compounds in this combination of tests is unpredictable. Molecular interactions including steric factors in the unpredictability of ATase inactivation may be related to the nature of the environment of the cysteine acceptor site in the ATase molecule.

The structure of the ATase protein derived from *E. coli* (Ada gene) has been elucidated by X-ray crystallographic techniques (M. H. Moore et. al., *EMBO Journal,* 1994, 13, 1495.). While the amino acid sequence of human ATase differs somewhat from that of bacterial origin, all known ATases (human, rodent, yeast, bacterial) contain the cysteine (Cys) acceptor site in a common fragment, Pro-Cys-His-Arg. A homology model of human ATase generated by computer from the crystal structure of the Ada protein (J. E. A. Wibley et. al., *Anti-Cancer Drug Design,* 1995, 10, 75.) resembles it in having the Cys acceptor buried in a pocket deep in the protein. Considerable distortion of the structure is necessary to bring either an $O^6$-alkylated guanine residue in intact DNA, or even free guanine alkylated by a relatively large group like benzyl, close to the Cys acceptor. These configurational changes are initiated by a characteristic binding of duplex DNA to the protein (K. Goodtzova et. al. *Biochemistry,* 1994, 33, 8385).

Since the amino acid components and dimensions of the ATase active site "pocket" are still unknown as are the details of the mechanism involved, it is impossible to predict the activity of a particular $O^6$-alkylated guanine or analogous ring system.

Published work in this field relates predominantly to the use of $O^6$-alkyl guanine derivatives having a nucleus identical to that of guanine in DNA. Chae et. al., *J. Med. Chem.* 1995, 38, 359–365 have described tests on a limited number of compounds in which the guanine ring was modified. However these compounds all had benzyl substitution at the $O^6$-position of the modified guanine ring or 6(4)-benzyloxy substitution on the pyrimidine ring. The observation that subtle changes in the substituents on the guanine ring or in the purine skeleton can generate agents that are very ineffective ATase inactivators, in comparison with their "parent" structure, suggests that more substantial modifications might also disrupt the ATase inactivating function.

There is a need for additional novel compounds useful for depleting ATase activity in order to enhance the effects of chemotherapeutic agents such as chloroethylating or methylating anti-tumour agents. It is a further object to provide compounds having better ATase inactivating characteristics than $O^6$-benzylguanine and having different solubility patterns.

Another object of the invention is to provide pharmaceutical compositions containing compounds which are useful for depleting ATase activity. A further object of the present invention is to provide a method for depleting ATase activity in tumour cells. A still further object of the invention is to provide a method for treating tumour cells in a host in such a way that they become more sensitive to the above-mentioned alkylating agents.

The present invention provide 6-hetarylalkyloxy pyrimidine derivatives of formula II:

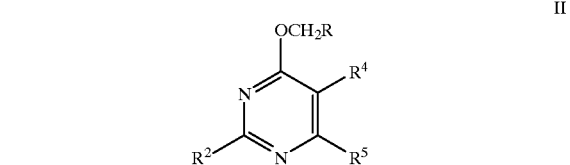

wherein
R is (i) a cyclic group having at least one 5- 6-membered heterocyclic ring, optionally with a carbocyclic or heterocyclic ring fused thereto, the or each heterocyclic ring having at least one hetero atom chosen from O, N or S, or a substituted derivative thereof; or
(ii) phenyl or a substituted derivative thereof,
$R^2$ is selected from H, $C_1$–$C_5$ alkyl, halogen or $NH_2$,
$R^4$ and $R^5$ which are the same or different are selected from H, NH—Y' or $NO_n$ wherein Y' is H, ribosyl, deoxyribosyl, arabinosyl, R"XCHR'" wherein X is O or S and R" is alkyl and R'" is H or alkyl, or substituted derivatives thereof,
n=1 or 2,
or $R^4$ and $R^5$ together with the pyrimidine ring form a 5- or 6-membered ring structure containing one or more hetero atoms,
and pharmaceutically acceptable salts thereof,
with the proviso that $R^2$ is not $NH^2$ if $R^4$ and $R^5$ form a ring structure IX

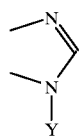

IX wherein Y is H, ribosyl, deoxyribosyl, or

wherein X is O or S, R" and R''' are alkyl, or substituted derivatives thereof, and with the proviso that R is not phenyl in the following circumstances a) to h):

a) if $R^2$ and $R^5$ are $NH_2$ and $R^4$ is NO or $NO_2$
b) if $R^2$ is $NH_2$ and $R^4$ and $R^5$ form a ring structure X

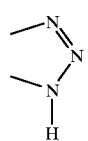

X c) if $R^2$ is $NH_2$ and $R^4$ and $R^5$ form a ring structure XI

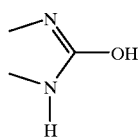

XI d) if $R^2$ is $NH_2$, and $R^4$ is $NO_2$ and $R^5$ is H or $CH_3$
e) if $R^2$, $R^4$ and $R^5$ are $NH_2$,
f) if $R^2$ and $R^5$ are $NH_2$ and $R^4$ is H,
g) if $R^2$ is H, and $R^4$ is $NO_2$ and $R^5$ is $NH_2$, or
h) if $R^2$ is F or OH, and $R^4$ and $R^5$ form a ring structure XII

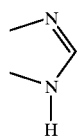

XII

Certain $O^6$-substituted guanine derivatives within the scope of the general formula in WO 94/29312 but not published therein have been found to have a surprisingly advantageous combination of properties which justifies the selection of such derivatives from among the class defined in WO 94/29312.

In another aspect, the present invention provides guanine derivatives of formula XIII:

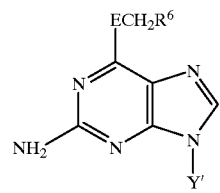

XIII wherein
E is O or S,
Y' is as defined for formula II above,
$R^6$ is a cyclic group having at least one 5- or 6-membered heterocyclic ring, optionally with a carbocyclic or heterocyclic ring fused thereto, the or each heterocyclic ring having at least one hetero atom chosen from O, N or S, or a substituted derivative thereof,
and pharmaceutically acceptable salts thereof, with the proviso that compounds published in WO 94/29312 are disclaimed.

In particular, the present invention selects advantageous compounds of formula XIV:

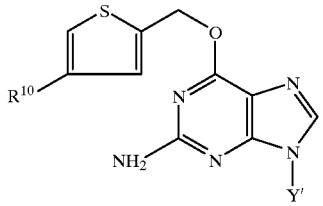

XIV wherein
$R^{10}$ is bromo, chloro or cyano, and
Y' is as defined for formula II.

Most preferably, $R^{10}$ is bromo. A particularly preferred and selected compound is $O^6$-(4-bromothenyl)guanine having the formula XV:

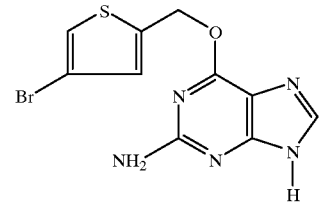

XV

This compound has an advantageous combination of properties including potential for oral administration.

R or $R^6$ may suitably be a 5- or 6-membered heterocyclic ring or a benzo derivative thereof, in which latter case the pyrimidine moiety may be attached to R or $R^6$ at either the heterocyclic or the benzene ring.

In preferred embodiments, R or $R^6$ is a 5-membered ring containing S or O, with or without a second ring fused thereto.

Preferably, R or $R^6$ is a heterocyclic ring having at least one S atom; more preferably, R or $R^6$ is a 5-membered heterocyclic ring having at least one S atom; and most preferably, R or $R^6$ is a thiophene ring or a substituted derivative thereof. Alternatively, R or $R^6$ may be a heterocyclic ring having at least one O atom, particularly, a 5-membered heterocyclic ring having at least one O atom and more particularly R or $R^6$ may be a furan ring or a substituted derivative thereof. As another alternative, R or $R^6$ may be a heterocyclic ring having at least one N atom, particularly R or $R^6$ may be a 6-membered heterocyclic ring having at least one N atom and in particular, R or $R^6$ may be a pyridine ring.

The carbocyclic or heterocyclic ring fused to the heterocyclic ring in R or $R^6$ may itself be bicyclic e.g. naphthalene.

In general the term "substituted derivative" as used in relation to any of the compounds of the invention means any substituted derivative whose presence in the compound is consistent with the compound having ATase depleting activity.

In the definition of Y or Y', the term "substituted derivative" includes further substitution by one or more of the following groups: hydroxy, halo, alkoxy, amino, alkylamino, amido or ureido. In a particularly preferred group of compounds, R" is hydroxy-substituted alkyl and R'" is H, so that Y' is hydroxyalkoxymethyl, preferably having 1 to 10 carbon atoms in the alkoxy group.

In the definition of R or $R^6$, the term "substituted derivative" includes substitution of the heterocyclic ring(s) and/or carbocyclic ring(s) by one or more of the following groups: alkyl, alkenyl, alkynyl, alkoxy, aryl, halo, haloalkyl, nitro, cyano, azido, hydroxyalkyl, $SO_nR^7$ where $R^7$ is alkyl and n=0, 1 or 2, or a carboxyl or ester group of the formula —$COOR^8$ wherein $R^8$ is H or alkyl. Halo, haloalkyl, cyano, alkylenedioxy, $SO_nR^7$ (as defined above) and —$COOR^8$ wherein $R^8$ is alkyl are preferred substituents.

An alkyl, alkoxy, alkenyl, or alkynyl group preferably contains from 1 to 20, more preferably from 1 to 10 and most preferably from 1 to 5 carbon atoms. Halo includes iodo, bromo, chloro or fluoro. An aryl group preferably contains from 1 to 20, more preferably from 1 to 10 carbon atoms, particularly 5 or 6 carbon atoms.

One embodiment of the invention provides a pharmaceutical composition containing compounds of formula II or formula XIII, as defined above, or a pharmaceutically acceptable salt thereof, and a pharmaceutically acceptable excipient. Optionally the composition may also contain an alkylating agent such as a chloroethylating or methylating agent.

In a further embodiment, the present invention provides a method for depleting ATase activity in a host comprising administering to the host an effective amount of a composition containing a compound of formula II or formula XIII as defined above, or a pharmaceutically acceptable salt thereof, more particularly a pharmaceutical composition as defined above. This method may alternatively be defined as a method of depleting ATase mediated DNA repair activity in a host.

The invention further provides a method for treating tumour cells in a host comprising administering to the host an effective amount of a composition containing a compound of formula II or formula XIII as defined above or a pharmaceutically acceptable salt thereof, more particularly a pharmaceutical composition as defined above and administering to the host an effective amount of a composition containing an alkylating agent. The method may be used for treatment of neoplasms including those which are known to be sensitive to the action of alkylating agents e.g. melanoma and glioma and others whose resistance to treatment with alkylating agents alone may be overcome by the use of an inactivator according to the invention.

The term "pharmaceutically acceptable salts" as used in this description and the claims means salts of the kind known in the pharmaceutical industry including salts with inorganic acids such as sulfuric, hydrobromic, nitric, phosphoric or hydrochloric acid and salts with organic acids such as acetic, citric, maleic, fumaric, benzoic, succinic, tartaric, propionic, hexamoic, heptanoic, cyclopentanepropionic, glycolic, pyruvic, lactic, malonic, malic, o-(4-hydroxybenzoyl)benzoic, cinnamic, mandelic, methanesulfonic, ethanesulfonic, 1,2-ethanedisulfonic, 2-hydroxyethanesulfonic, benzenesulfonic, p-chlorobenzenesulfonic 2-naphthalenesulfonic, p-toluenesulfonic, camphorsulfonic, 4-methyl-bicyclo [2.2.2]oct-2-ene-1-carboxylic, glucoheptonic, 4,4'-methylenebis(3-hydroxy-2-naphthoic), 3-phenylpropionic, trimethyl-acetic, tertiary butylacetic, lauryl sulfuric, gluconic, glutamic, hydroxynaphthoic, salicyclic, stearic, or muconic, and the like.

Subject to the provisos above the preferred compounds of the invention are those of:

Type 1

Formula III

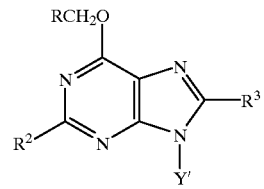

III wherein:

R is as defined for formula II, particularly furyl or thienyl unsubstituted or substituted, preferably with a halogen such as chlorine, bromine or fluorine, or with cyano Y' is as defined for formula XIII, preferably Y' is H or $HOCH_2CH_2OCH_2$—;

$R^2$ is H, $NH_2$, $C_1$–$C_5$ alkyl, preferably methyl, or halogen, preferably fluorine;

$R^3$ is H or OH:

Type 2

Formula IV

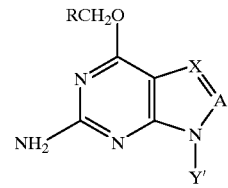

IV wherein:

R is as defined for formula II, particularly phenyl, thienyl or furyl unsubstituted or substituted preferably with a halogen such as chlorine, bromine or fluorine, or with cyano, or phenyl having a methylenedioxy ring structure fused thereto;

Y' is as defined for formula XIII;

X is CH or N;

A is CH or N; and preferably when X=N, A=CH

Formula V

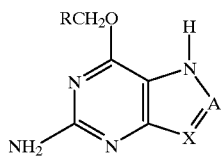

wherein:
R is as defined for formula II
X is CH or N
A is CH or N;

Type 3

Formula VI

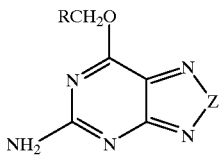

wherein:
R is as defined for formula II, particularly, thienyl or furyl unsubstituted or substituted preferably with a halogen such as chlorine or bromine;
Z is O or S or CH=CH
A particularly preferred group of compounds of this type are $O^6$-(4-halothenyl)-8-thiaguanines, particularly $O^6$-(4-bromothenyl)-8-thiaguanine.

Formula VII

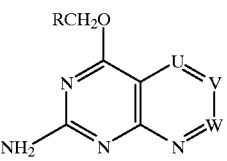

wherein:
R is as defined for formula II;
U is CH or N;
V is CH or N;
W is CH or N;
provided that U, V and W are not all CH.

Type 4

Formula VIII

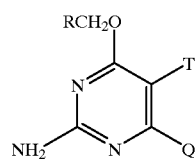

wherein:
R is as defined for formula II, particularly thenyl or furyl optionally substituted with halogen preferably one or more of chlorine, bromine or fluorine;

T is H, $NH_2$ or $NO_n$ where n=1 or 2;
Q is H, $NH_2$ or $NO_n$ where N=1 or 2;

Type 5

Formula XVI

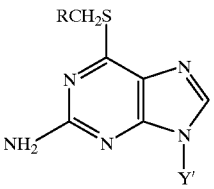

wherein
R is as defined for formula XIII
Y' is as defined for formula II

BRIEF DESCRIPTION OF DRAWINGS

The invention will be described in greater detail with reference to the accompanying drawings, in which:

FIG. 1 shows the effect of 1 uM B.4316 pretreatment of Raji cell sensitization to temozolomide.

FIG. 2 shows the effect of 10 μm B.4316 pretreatment on Raji cell sensitization to BCNU.

FIG. 3 shows the effect of 10 μM B.4316 pretreatment on Raji cell sensitization to fotemustine.

FIG. 4 shows the effect of 10 μM B4316 pretreatment on Raji cell sensitization to melphalan and cisplatin.

FIG. 15A is a graph of % tumour growth against time (days) showing the comparison of the effect of B.4280 given i.p. and orally (p.o.) on the sensitivity of human melanoma xenografts to growth inhibition by temozolomide. Animals were untreated, given temozolomide alone (100 mg/kg) or B.4280 alone (20 mg/kg, i.p.) or B.4280 (20 mg/kg, i.p.) or B.4280 (30 mg/kg, p.o.) followed 1 hour later by temozolomide (100 mg/kg, i.p.) on five consecutive days. Tumour growth was monitored as described. The data from a number of separate studies are presented.

FIG. 18 relates to B.4280 (20 mg/kg, i.p.) in A375M tumours and other tissues.

FIG. 19 relates to B.4280 (30 mg/kg, p.o.) in A375M tumours and other tissues.

FIG. 20 relates to B.4280 (30 mg/kg i.p.) in MCF-7 tumours and other tissues.

FIG. 21 relates to B.4280 (20 mg/kg i.p.) in DU-145 tumours and other tissues.

FIG. 24 consists of graphs of % tumour growth and number of surviving mice against time (days) for sensitization of A375M tumours with B.4205 (PaTrin-1) and B.4280 20 mg/kg pretreatment followed by 150 mg/kg temozolomide using a 5 day schedule as for FIG. 22.

Figure 1:
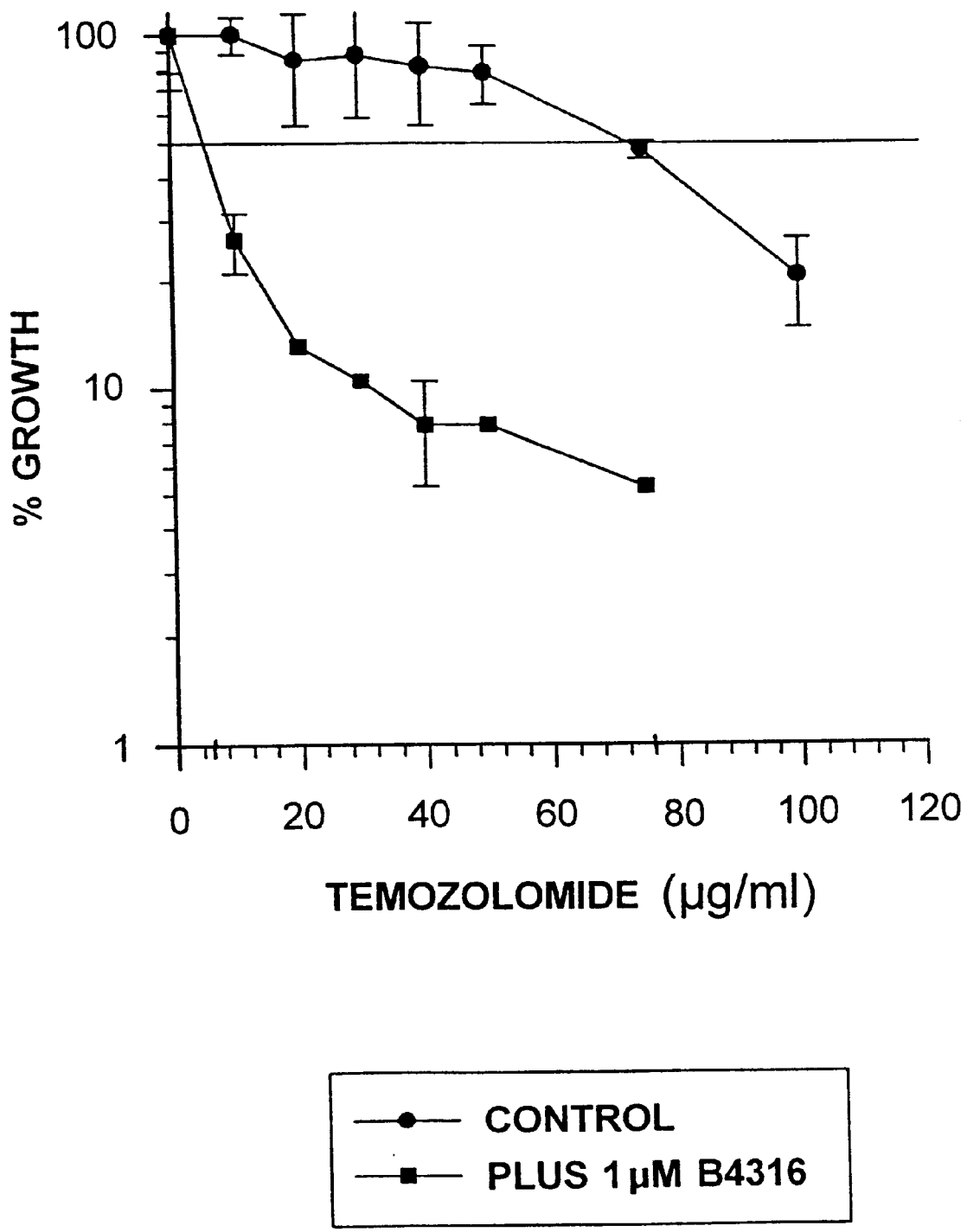
FIGS. 1 to 4 are graphs showing the effect of pretreatment with compound B.4316 on Raji cell sensitization to different chemotherapeutic agents. Each graph plots percentage growth against the concentration (μg/ml) of the chemotherapeutic agent in the presence and absence of B.4316.

In the specification the abbreviations "1 h" or "2 h" etc. mean "1 hour", "2 hours" etc. In the drawings the abbreviations "Temo" and "Tz" refer to temozolomide.

FIG. 27 consists of graphs of % tumour growth and weight (% of day 1 value) against time (days) showing tumour DU-145 prostate xenograft growth after temozolomide (100 mg/kg/day) and/or B.4280 (PaTrin-2) (20 mg/kg/day) days 1–5. Points are the means of values from at least 4 mice. Growth delays in each group were (p value): PaTrin-2 alone 0.1 days (>0.05); temozolomide alone 7.8 (>0.05). Both agents 15.3 (0238).

Figure 28:
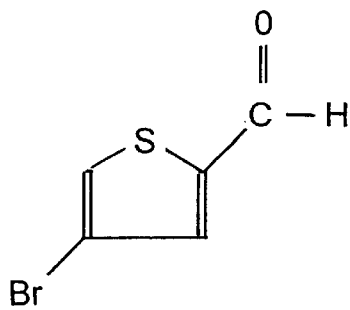
Figure 28:
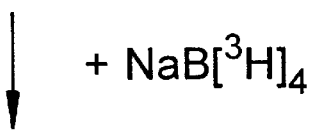
Figure 28:
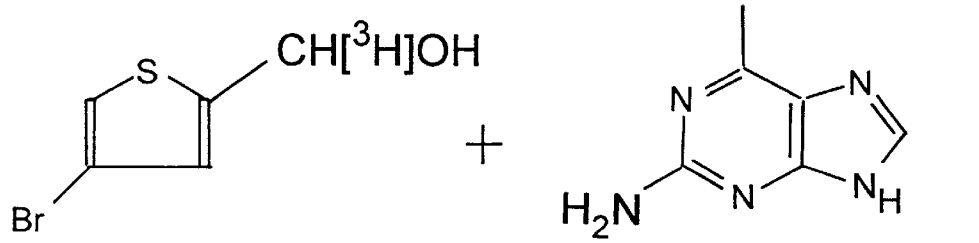
Figure 28:
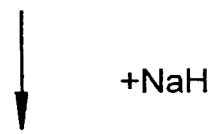
Figure 28:
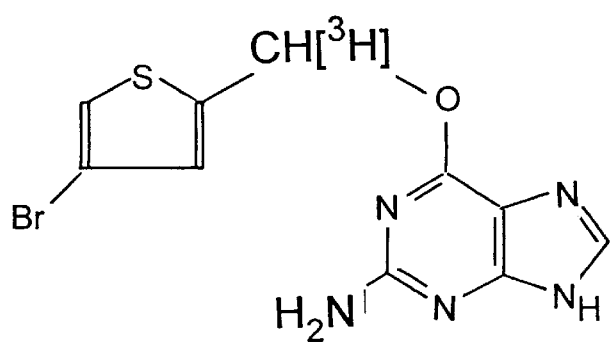

FIG. 28 is a reaction scheme for synthesis of $O^6$-[$^3$H]-(4-bromothenyl)guanine.

Figure 29:
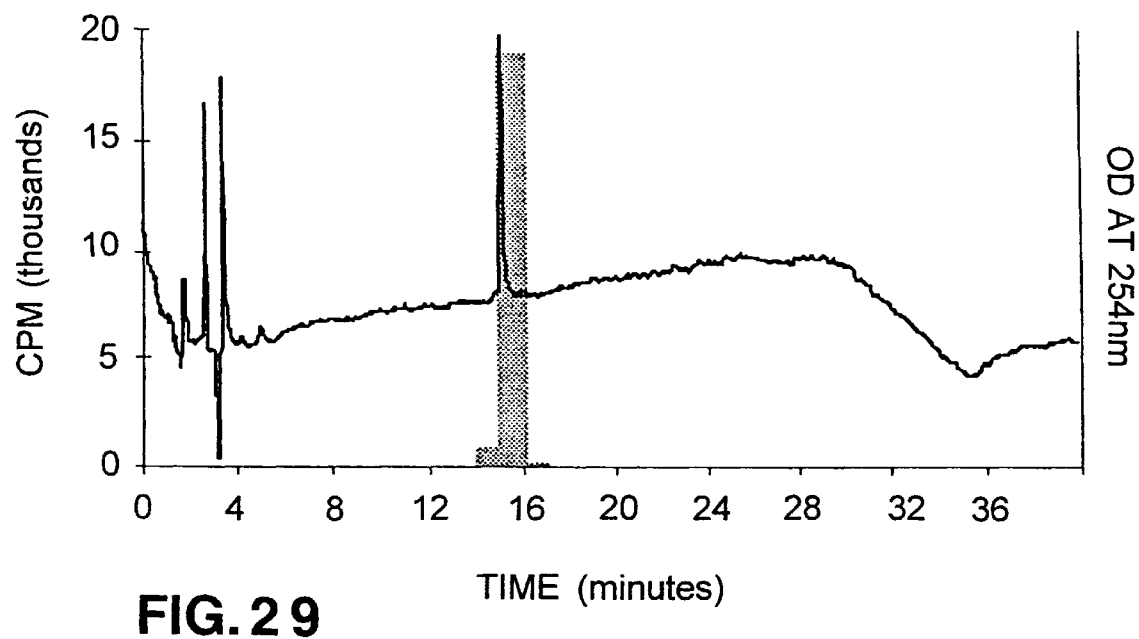

FIG. 29 shows co-chromatography of authentic B.4280 and readioactivity in the product of $O^6$-[$^3$H]-(4-bromothenyl)guanine synthesis. Shading indicates counts recovered (LH axis) and the line OD at 254 nm (RH axis).

Figure 30:
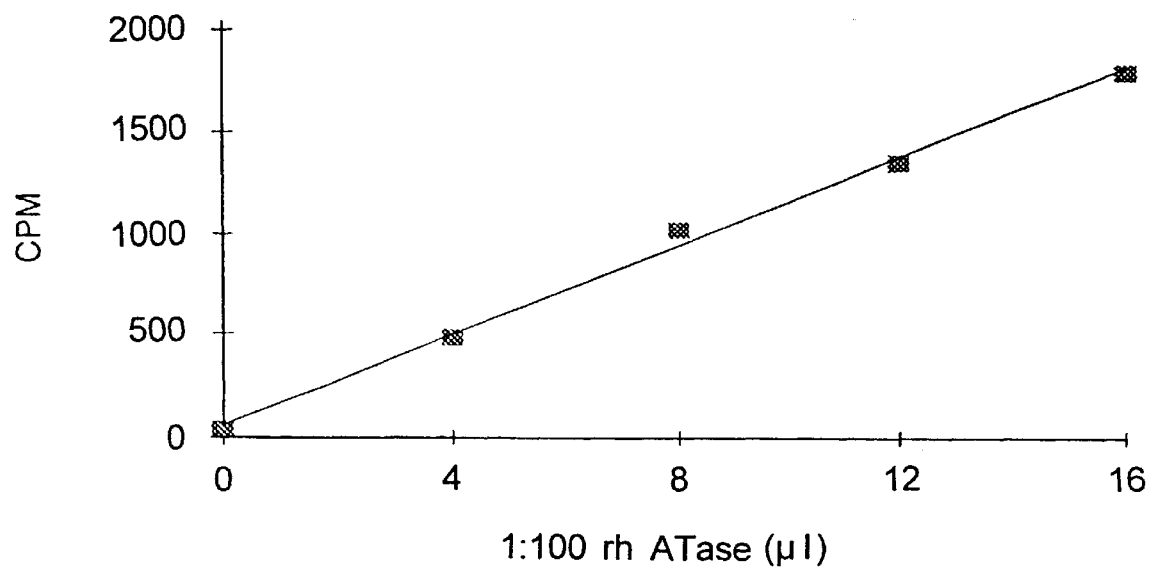

FIG. 30 shows transfer of radioactivity from $O^6$-[$^3$H]-(4-bromothenyl)guanine to rhATase after one hour incubation at 37° C.

DESCRIPTION OF THE PREFERRED EMBODIMENTS

Examples of compounds of the invention are shown in Tables 1a and 1b. They were synthesized by the procedures presented below, adapted as appropriate.

Type 1

A. $O^6$-Substituted hypoxanthines were made by the action of alkoxide $RCH_2ONa$ on the quaternary salt N,N,N-trimethyl-1H-purin-6aminium chloride.[1]

B. $O^6$-Substituted 2-methylhypoxanthines were made similarly, from the quaternary salt from diazabicyclooctane (DABCO) and 6-chloro-2-methylpurine.[2]

C. $O^6$-Substituted 2-fluorohypoxanthines were made by diazotisation of the corresponding guanines using sodium nitrite and concentrated fluoboric acid at −25° C.[3]

D. $O^6$-Substituted 9-(2-hydroxyethoxymethyl)guanines were made by condensing the corresponding guanines after silylation with 2-acetoxyethoxymethyl bromide in the presence of mercuric cyanide followed by saponification of the O-acetyl group.[4]

E. $O^6$-Substituted 8-hydroxyguanines were made from 6-hetarylmethyl-2,4,5-triaminopyrimidines and 1, 1-carbonyldiimidazole in DMF.[5] Reaction of 6-chloro-2, 4-diaminopyrimidine with alkoxide in DMSO, followed by nitrosation with sodium nitrite in aqueous acetic acid and reduction using sodium hydrosulphite in aqueous DMF, gave the 2, 4, 5-triamines.

Type 2

A. $O^6$-Substituted 8-azaguanines were made from the above triamines and sodium nitrite in aqueous acetic acid.[6]

B. $O^6$-Substituted 8-aza-7-deazaguanines were made from the alkoxide $RCH_2ONa$ and 2-amino-6-chloro-8-aza-7deazapurine[7] in sulfolane or from the DABCO quaternary salt (in DMSO solvent) derived from it.

Type 3

A. $O^6$-Substituted 8-oxaguanines were made by lead tetraacetate oxidation[8] of 6-hetarylmethyl-2,4-diamino-5-nitrosopyrimidines obtained as under Type IE.

B. $O^6$-Substituted 8-thiaguanines were made from the triamine intermedites under Type IE and N-tosylthionylimine in pyridine.[9]

C. $O^4$-Substituted pterins were made from these triamines and glyoxal with sodium metabisulphite.[10]

Type 4

A and B.

These pyrimidines were obtained as under Type IE.

C. $O^6$-Substituted 2,4-diamino-5-nitropyrimidines were made by the action of alkoxide $RCH_2ONa$ in DMSO on 6-chloro-2,4-diamino-5-nitropyrimidine.[11]

Type 5

$S^6$-Substituted 6-thioguanines were prepared from the thiolate $RCH_2SNa$ and the quaternary salt 2-amino-N,N,N-trimethyl-1H-purin-6-aminium chloride (WO 94/29312).

$O^6$-Substituted guanines as listed in Tables 6a and 6b were made by the standard preparation as described in WO 94/29312, usually with 3 mmol alcohol $RCH_2OH$ per mmol quaternary salt.

The alcohols were made as described in U.S. patent application Ser. No. 08/568,576, filed Dec. 7, 1995 by sodium borohydride reduction of the corresponding aldehydes, with two exceptions. For 4-bromothenyl alcohol[12] required for B.4280 the aldehyde is commercially available. 5-Chlorothiophen-2-aldehyde[13] and 5-methylthiothiophen-2-aldehyde[14] were prepared by Vilsmeier reaction on 2-chlorothiophen and 2-methylthiothiophen respectively. Sodium borohydride reduction of the methylthioaldehyde followed by sodium periodate oxidation[15] of the resulting methylthioalcohol yielded the methylsulphinylalcohol required for B.4294. Reduction of the chloroaldehyde gave 5-chlorothenyl alcohol[16] for B.4281.

Several other aldehydes were obtained by halogenation of the appropriate thiophen aldehyde or furfural. Thus, direct bromination gave 5-bromofurfural[17] and thence the alcohol[18] for B.4336. Halogen in presence of aluminum chloride on thiophen-2-aldehyde yielded 4-chlorothiophen-2-aldehyde[19] (for the alcohol for B.4298), on thiophen-3-aldehyde yielded 2-bromothiophen-4-aldehyde[20] (and eventually B.4313), and on 5-chlorothiophen-2-aldehyde yielded 4,5-dichlorothiophen-2-aldehyde[21] (for the alcohol[22] for B. 4318).

Cyanoaldehydes were obtained from copper cyanide and the corresponding bromoaldehydes in refluxing dimethylformamide. 5-Cyanothiophen-2-aldehyde[23] and its 4-cyano isomer[24] then gave the 5-cyano and 4-cyano[25] alcohols, for B.4283 and B.4317 respectively.

4-Methoxythenyl alcohol[26] (for B.4300) was prepared as described from 2,3-dibromosuccinic acid and methyl thioglycollate, and ultimate reduction of the methyl ester (not aldehyde in this case) by lithium aluminium hydride and 2-chloro-4-picolyl alcohol[27] (for B.4321) by sodium borohydride reduction[28] of the corresponding acid chloride, made in turn from reaction[29] of phosphorus oxychloride/pentachloride on isonicotinic acid N-oxide.

For B.4282, 3-pyridinemethanol N-oxide is commercially available. 5-Methylsulphonylthenyl alcohol (for B.4309) was obtained by m-chloroperbenzoic acid (MCPBA) oxidation of the alcohol resulting from reduction of 5-methylthio-2-thiophenecarboxaldehyde[30].

6-Chloro-3-pyridinemethanol (for B.4319) and 5-bromo-3-pyridinemethanol (for B.4320) were made by treatment of 6-chloro and 5-bromonicotinic acids respectively with phosphorus oxychloride/pentachloride and reduction of the resulting acid chlorides with sodium borohydride[28]. Isothiazole-4-methanol (for B.4354) was obtained by reduction of the corresponding methyl ester (A. Adams, and R. Slack, *J. Chem. Soc.* 1959, 3061) with lithium aluminium hydride (M. Hatanaka and T. Ishimaru, *J. Med. Chem.* 16, 1973, 978).

4-bromo-2-thiophenecarboxaldehyde was converted into the 4-lithio derivative (A. L. Johnson, *J. Org. Chem.* 41, 1976, 1320) of its ethylene acetal and reaction of this organometallic with dimethyl disulphide followed by acid hydrolysis gave 4-methylthio-2-thiophenecarboxaldehyde (R. Noto, L. Lamartina, C. Arnone and D. Spinelli, *J. Chem. Soc., Perkin Trans.* 2, 1987, 689). Sodium borohydride reduced this aldehyde to the 4-methylthio alcohol (for B.4356), which in turn with one of two equivalents of MCPBA yielded the 4-methylsulphinyl and 4-methylsulphonyl alcohols (for B.4377 and B.4361 respectively). reaction of the above organometallic with naphthalene-2-sulphonyl azide (A. B. Khare and C. E. McKenna, *Synthesis*, 1991, 405) and sodium pyrophosphate followed by hydrolysis by the method (P. Spagnolo and P. Zamirato, *J. Org. Chem.*, 43, 1978, 3539) for the preparation of other azidothiophene aldehydes gave 4-azido-2-thiophenecarboxaldehyde leading to the alcohol for B.4373.

5-Iodo-3-thiophenemethanol (for B.4357) came from the aldehyde obtained by treatment of 3-thiophenecarboxaldehyde with iodine-iodic acid-sulphuric acid (R. Guilard, P. Fournari and M. Person, *Bull. Soc. Chim. France*, 1967, 4121).

2-Naphtho[2,1-b]thienylmethanol (for B.4366) was prepared by lithium aluminium hydride reduction of the corresponding carboxylic acid (M. L. Tedjamulia,, Y. Tominaga, R. N. Castle and M. L. Lee, *J. Heterocycl. Chem.*, 20, 1983, 1143). 5-Phenylthenyl alcohol (m.p. 91.5° C. for B.4378) resulted from sodium borohydride reduction of the aldehyde (P. Demerseman, N. P. Buu-Hoi and R. Royer, *J. Chem. Soc.*, 1954, 4193) obtained by Vilsmeier reaction of 2-phenylthiophene (from Gomberg-Bachmann reaction (N. P. Buu-Hoi and N. Hoan, *Rec. trav. chim.*, 69, 1950, 1455) of benzenediazonium chloride and alkali with thiophene).

By way of specific example, the preparation of $O^6$-(4-bromothenyl)guanine (B.4280) will now be described.

Preparation of $O^6$-(4-bromothenyl)guanine

A solution of 4-bromothenyl alcohol[12] [4.63 g, 24 mmol; $R_f$ 0.38 in TLC (PhMe-MeOH, 4:1)] in DMSO (4 ml) was treated cautiously with sodium hydride (60% in oil; 0.64 g, 16 mmol). After 1 hour's stirring, 2-amino-N,N,N-trimethyl-1H-purin-6-aminium chloride (1.83 g, 8 mmol) was added. After 1 hour's further stirring, acetic acid (1.3 ml) followed by ether (240 ml) was added and the solid filtered off after 1–2 h. Removal of solvents and excess of alcohol (b.p. 85–90° C./0.4 mm) from the filtrate yielded a negligible second fraction (17 mg). The main crop was triturated with water (10 ml), affording substantially pure product (1.89 g, 73%) with $R_f$ 0.22 in TLC (PhMe-MeOH, 4:1). It was recrystallized by dissolving in hot methanol (100 ml) and then concentrating. Analytical data are given in Tables 6a and 6b, together with data for other compounds. Other typical synthetic procedures are described by way of example in a special section later in this text.

Compounds of formula II or XIII in which Y' is R"XCHR"' and R"' is alkyl (seco-nucleosides) may be prepared by an analogous preparation to the reaction of $O^6$-benzylguanine with -chloro-ethers (MacCoss et al., *Tetrahedron Lett.*; European Patent Application No. 184,473, loc. cit.) or with alkyl bromides (e.g. Kjellberg, Liljenberg and Johansson, *Tetrahedron Lett.*, 1986, 27, 877; Moschel, McDougall, Dolan, Stine, and Pegg, *J. Med. Chem.*, 1992, 35, 4486).

Typical "sugar" components corresponding to R"XCHR"', leading to seco-nucleosides, are made by methods described in e.g. McCormick and McElhinney, *J. Chem. Soc., Perkin Trans.* 1, 1985, 93; Lucey, McCormick and McElhinney, *J. Chem. Soc. Perkin Trans.* 1, 1990, 795.

Compounds of formula II or XIII in which Y is ribosyl or deoxyribosyl (nucleosides) may be prepared by methods analogous to the syntheses of $O^6$-benzylguanine riboside and 2-deoxyriboside (Moschel et al. 1992; cf. Gao, Fathi, Gaffney et al., *J. Org. Chem.*, 1992, 57, 6954; Moschel, Hudgins and Dipple, *J. Amer. Chem. Soc.*, 1981, 103, 5489) (see preparation of Ribosides above).

INDUSTRIAL APPLICABILITY

The amount of the compound of the present invention to be used varies according to the effective amount required for treating tumour cells. A suitable dosage is that which will result in a concentration of the compound of the invention in the tumor cells to be treated which results in the depletion of ATase activity, e.g. about 1–2000 mg/kg body weight, and preferably 1–800 mg/kg body weight, particularly 1–120 mg/kg body weight, prior to chemotherapy with an appropriate alkylating agent.

The pharmaceutical composition of the invention may be formulated in conventional forms with conventional excipients, as described for example in and U.S. Pat. Nos. 5,525,606 and 5,091,430 and 5,352,669, the contents of which are incorporated herein by reference in their entirety. The composition may contain the inactivator according to the invention together with an appropriate alkylating agent; or the composition may comprise two parts, one containing the inactivator and the other containing the alkylating agent. The method of administering the compounds of the invention to a host may also be a conventional method, as described in WO 91/13898 for example. For administration of an inactivator according to the invention to patients, the pharmaceutical composition may suitably contain the inactivator in a suitable vehicle such as 40% polyethyleneglycol 400 in saline solution, or in saline or 3% ethanol (in saline), for intravenous injection, or in a powder form in suitable capsules for oral administration.

Alkylating agents may be administered in accordance with known techniques and in conventional forms of administration, as described in WO 91/13898 for example or preferably as a single dose immediately after or up to 24 hours after but preferably around 2 hours after administration of the ATase inactivating agents and also at doses lower than those used in standard treatment regimen. A reduction in dose may be necessary because the inactivators would generally be anticipated to increase the toxicity of the alkylating agents. Examples of chloroethylating agents include 1,3 bis (2-chloroethyl)-1-nitrosourea (BCNU), 1-(2-chloroethyl)-3-cyclohexyl-1-nitrosourea (CCNU), fotemustine, mitozolomide and clomesone and those described in McCormick, McElhinney, McMurry and Maxwell *J. Chem. Soc. Perkin Trans.* 1, 1991, 877 and Bibby, Double, McCormick, McElhinney, Radacic, Pratesi and Dumont *Anti-Cancer Drug Design*, 1993, 8, 115. Examples of methylating agents include temozolomide and U.S. Pat. No. 5,260,291 the contents of which are incorporated herein in their entirety) and dacarbazine, procarbazine, and streptozocin.

METHODS $O^6$-alkylguanine-DNA-alkyltransferase assay

Varying amounts of recombinant ATase or cell/tissue extracts were incubated with [$^3$H]-methylnitrosourea-methylated calf thymus DNA (specific activity, 17 Ci/mmol) at 37° C. for 1 hour in a total volume of 300 µl buffer 1/[50 mM Tris/HCl (pH 8.3), 3 mM dithiothreitol (DTT), 1 mM EDTA] containing 1 mg/ml bovine serum albumin (IBSA) for recombinant ATases and tissue extracts, or 1.1 ml buffer 1 for cell extracts. After incubation, bovine serum albumin (100 µl of 10 mg/ml in buffer 1) and perchloric acid (100 µl of 4M perchloric acid for 300 µl volumes and 400 µl for 1.1 ml volumes) and 2 ml of 1M perchloric acid were added. Samples were then heated at 75° C. for 50 minutes to hydrolyze the DNA. Samples were then centrifuged at 3,000 rpm for 10 minutes and the precipitate washed once with 4 ml of 1M perchloric acid, before being resuspended in 300 µl of 0.01M sodium hydroxide and dissolved in 3 ml of aqueous scintillation fluid (Ecoscint A, National Diagnostics). Counting efficiency was approximately 30%.

ATase specific activity was calculated from the region where the activity was proportional to the amount of extract added, since with higher amounts of extracts the reaction becomes substrate limiting. ATase activity is expressed as fmol methyl transferred to protein per mg of total protein in the extract.

Method of Purification of Recombinant ATases

The cDNA cloning and overexpression of the human ATase has been reported previously[30]. Purification of the recombinant proteins was achieved either by affinity chromatography through a DNA-cellulose column as described by Wilkinson et al.,[31, 32] or by DEAE-cellulose ion-exchange chromatography. For the latter, the ATase protein was partially purified by ammonium sulphate precipitation (30–60%) and dialyzed against 10 mM Tris-HCl pH 7.5, 1 mM DTT, 2 mM EDTA, 10% glycerol, before loading on a DEAE-cellulose column. The ATase was then eluted with a 0–0.1 M NaCl gradient. The purified human ATase protein retained activity for more than one year when stored at high concentration at −20° C. in buffer 1 [50 mM-Tris/HCl (pH 8.3)/3 mM-dithiothreitol/1mM-EDTA] and could be thawed and refrozen several times without substantial loss of activity.

Incubation with Inactivators and ATase Assay

Compounds to be tested were dissolved in DMSO to a final concentration of 10 mM and diluted just before use in buffer 1. Recombinant ATase was diluted in buffer 1 containing 1 mg/ml bovine serum albumin (IBSA) and tilrated as described above in order that the reaction be conducted under ATase, and not substrate, limiting conditions. In each assay, fixed amounts of ATase (60–75 fmol) were incubated with varying amounts of $O^6$-benzylguanine, or test compound in a total volume of 200 $\mu$l of IBSA containing 10 $\mu$g of calf thymus DNA at 37° C. for 1 hour. The [$^3$H]-methylated-DNA substrate (100 $\mu$l) containing 4 $\mu$g of DNA and 100 fmol of $O^6$-methylguanine) was then added and incubation continued at 37° C. for 1 hour, until the reaction was complete. Following acid hydrolysis of the DNA as described above the [$^3$H]-methylated protein was recovered and quantitated by liquid scintillation counting. $I_{50}$ is the concentration of inactivator required to produce a 50% reduction in ATase activity under the above conditions.

Cell Culture and Preparation of Extracts

Mammalian cells including Raji cells (a human lymphoblastoid cell line from a Burkitt's lymphoma), A375M cells (human melanoma cells), MCF-7 cells (human breast cancer cells) and PC3 and DU145 (both human prostate cancer cells) were cultured under standard conditions. For example, Raji cells were grown in suspension culture in RPMI medium supplemented with 10% horse serum. Cell pellets were resuspended in cold (4° C.) buffer I containing 2 $\mu$g/ml leupeptin and sonicated for 10 seconds at 12 $\mu$m peak to peak distance. After cooling in ice, the cells were sonicated for a further 10 seconds at 18 $\mu$m. Immediately after sonification, 10 $\mu$l/ml of phenylmethanesulphonylfluoride (PMSF 8.7 mg/ml in 100% ethanol) was added and the sonicates centrifuged at 15000cpm for 10 minutes at 4° C. to pellet cell debris. The supernatant was transferred to a tube on ice and kept for determination of ATase activity (see above).

Stability of Inactivators at 37° C. by Spectrophotometry.

Inactivators (10mM in DMSO) were diluted to 0.1mM in prewarmed degassed PBS (pH 7–7.2). PBS (Phosphate buffered saline) is 0.8% NaCl, 0.02% KCl, 0.15% $Na_2H_2PO_4$, 0.02% $KH_2PO_4$. Samples were immediately transferred to a CARY13 spectrophotometer (cuvette block held at 37° C.) and scanned at an appropriate wavelength (according to the spectral properties of the compound) at 5–10 minute intervals for up to 80 hours. The results were expressed as percentage absorbance change versus time and T½ values (half life) extrapolated from this. In the tables the results of these tests are identified by "in PBS" or "by Spec".

Stability of Inactivators of ATase Assay

Inactivators (10 $\mu$M in DMSO) were diluted to the appropriate concentration ($I_{90}$ calculated from previous $I_{50}$ determination data) in buffer I without DTT and incubated for varying times at 37° C. Samples were then taken for use in the competition assay to assess the compound's ability to inactivate human ATase. The results were expressed as reduction in activating activity versus time and T ½ values extrapolated from this.

Inactivation of ATase Activity in Raji Cells.

Raji cells were diluted to between $5 \times 10^5$/ml and $10^6$/ml in medium containing either the appropriate concentration of inactivator or an equivalent volume of vehicle (DMSO). Following incubation at 37° C. for 2 hours the cells were harvested by centrifugation, washed twice with PBS and the resulting cell pellets (between $5 \times 10^6$ and $10^7$ cells per pellet) stored at −20° C. ATase activity was determined as described above, in duplicate cell extracts and expressed as the percentage activity remaining, based on that present in the untreated controls (350–450 fm/mg depending on the assay). $I_{50}$ (i.e concentration of inactivator required to reduce ATase activity by 50%) values were extrapolated from this data.

Sensitization of Mammalian Cells to Cytotoxic Agents.

Sensitization of mammalian cells to the cytotoxic effects of BCNU, temozolomide and other cytotoxic agents following a 2 hour pretreatment with inactivator was analysed using an XTT-based growth inhibition assay[22]. Cells were plated in 96 well plates (for example in the case of Raji cells at 500 cells/well) and incubated at 37° C. for 30 minutes prior to the addition of medium containing either the appropriate concentration of inactivator or an equivalent volume of vehicle. Following a 2 hour incubation at 37° C., medium containing either increasing doses of cytotoxic agent or equivalent vehicle was added and the cells allowed to grow for 6 days. At this time XTT solution was added and the cells incubated for a further 4 hours at 37° C. The resulting red/orange formazan reaction product was quantified by measuring adsorption at 450 nm on a microtitre platereader.

From this data the percentage growth of cells relative to that in control wells was determined for a range of BCNU, temozolomide or other cytotoxic agent doses in both the presence and absence of inactivator. Sensitization factor (SF) based on $D_{50}$ ($D_{50}.^C/D_{50}.^I$) was determined by dividing the $D_{50}$ (i.e. dose at which there was 50% growth versus the controls untreated with alkylating agent) calculated for the cytotoxic agent alone ($D_{50}.^C$) by that for the cytotoxic agent plus inactivator ($D_{50}.^I$). A value of one (1) thus indicates no sensitization by the inactivator. Comparable Sensitization factors were also determined in some cases based on $D_{60}$ and $D_{80}$, i.e. the dose at which there were respectively 60% or 80% growth compared to the untreated controls. In Table 3 the Sensitization Factor $D_{50}.^C/D_{50}.^I$ is shown as $D_{50}$ control/$D_{50}$ 'B', with the letter 'B' referring to the inactivator compound.

Xenograft Studies

Animals

Figure 11:
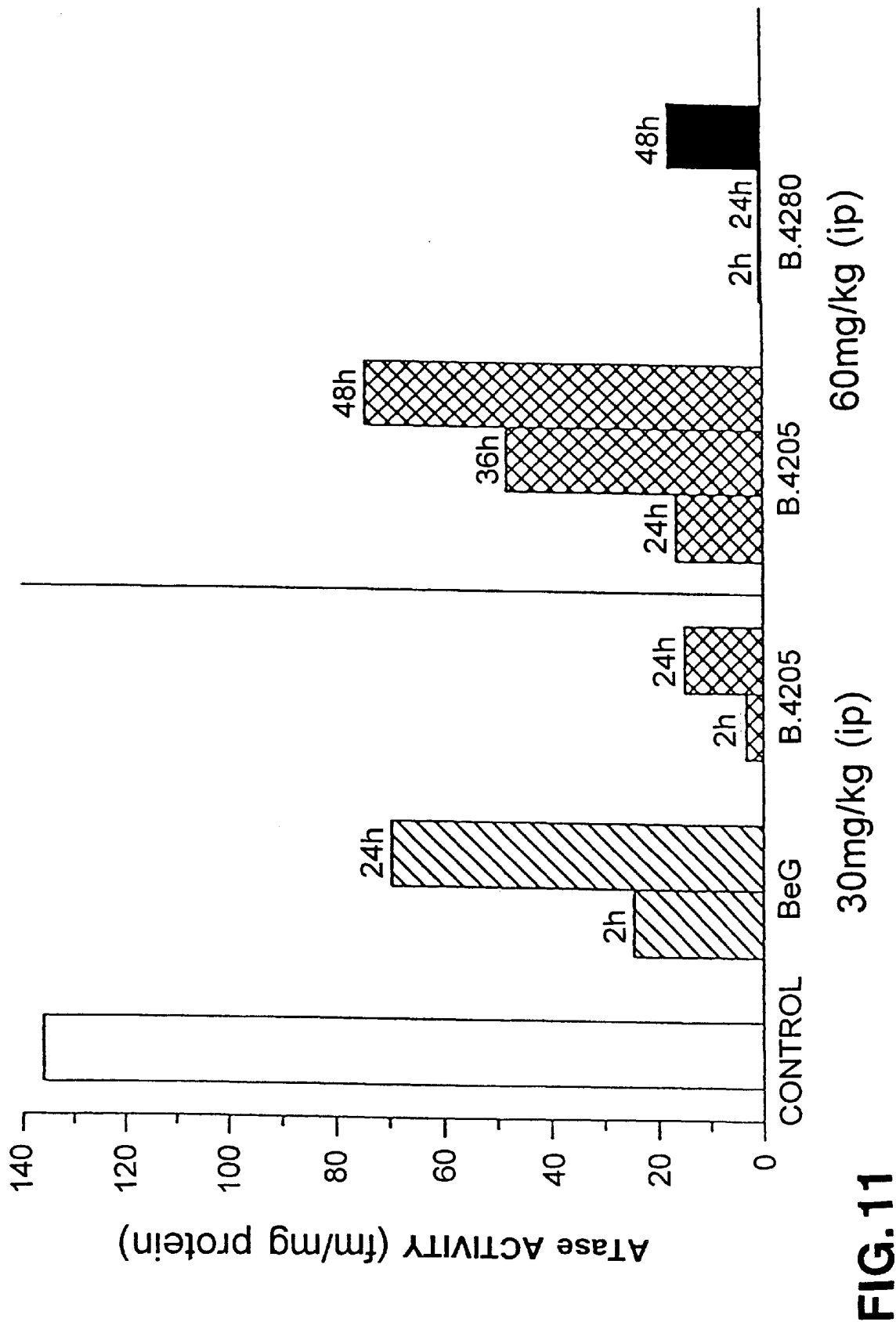
FIG. 11 is a histogram of ATase activity (fm/mg) against time (hours) showing the effect of ATase inactivators BeG, B. 4205 and B.4280 on ATase activity in human melanoma xenografts grown in nude mice. Animals were given a single dose of the inactivators intraperitoneally (i.p.) at 30 mg/kg or 50 mg/kg and sacrificed after the times shown.
Figure 17:
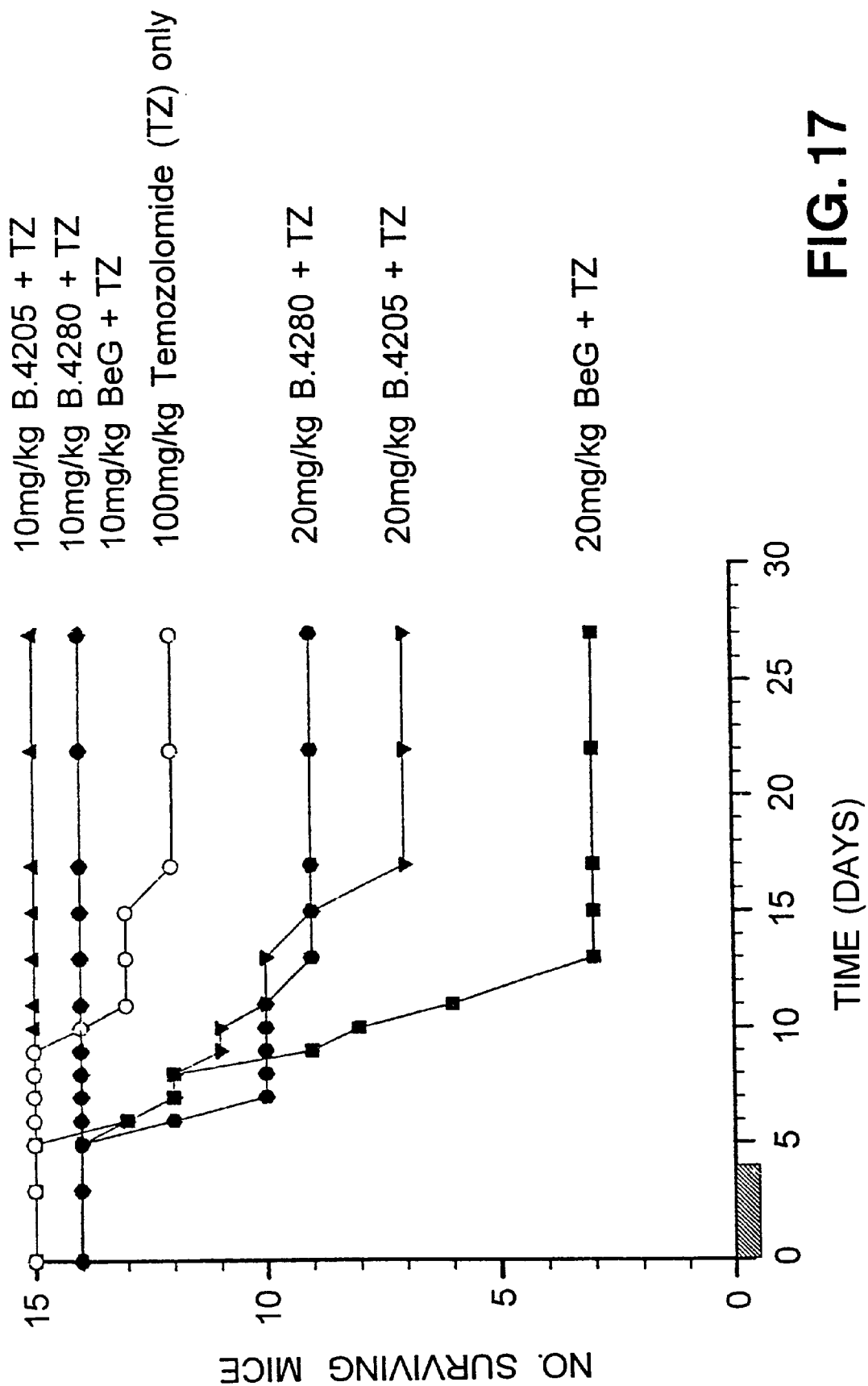
FIG. 17 is a graph showing the survival of animals in a comparative test of the effects of BeG, B.4205 and B.4280 in combination with temozolomide (TZ) in non-tumour-bearing $DBA_2$ mice. Animals were given temozolomide alone (100 mg/kg i.p) or BeG (10 or 20 mg/kg, i.p.), B.4205 (10 or 20 mg/kg i.p.) or B.4280 (10 or 20 mg/kg i.p.) followed one hour later by temozolomide (100 mg/kg i.p.) on five consecutive days.

Swiss mouse derived athymic male mice (o/nu) weighing between 20–30 g were obtained from ZENECA Pharmaceuticals, Alderley Park, Macclesfield, Cheshire, SK10 4T6, England. Animals were housed 4–5/cage in filter top cages and had access to food and water ad libitum. All animals were maintained under a controlled 12h-light-12h-dark cycle. These animals were used for all tests except those which are shown in FIGS. 11 and 17 and Table 8, as mentioned below.

Cells

A375M (human melanoma) and DU145 (human prostrate cancer) cells were grown in DMEM containing 10% foetal bovine serum (FBS), MCF-7 (human breast cancer cells) were grown in DMEM containing 10% FBS supplemented with 100iu insulin.

Tumours

A375M, DU145 and MCF-7 cells ($10^6$) in 100 μl PBS were injected subcutaneously into the right-hand flank of 8–10 week old o/nu athymic mice. These cells were allowed to develop into a tumour for 3–4 weeks (A375M and DU145 cells) and 4–6 weeks (MCF-7 cells). Once established, tumours were maintained by subcutaneous implantation of 2 mm$^3$ blocks into the right-hand flank of athymic o/nu mice. MCF-7 tumours are oestrogen positive and require oestrogen for growth. This was supplied as a subcutaneous implant (see below) at the tail base simultaneously to the tumour implant and monthly thereafter.

Preparation of Oestrogen Pellets 468 mg β-oestradiol was added to 9.7 g silastic and mixed until evenly distributed. 1.1 g of curing agent was added and the whole mixture spread into 3 (26 mm×12 mm×1 mm) glass fomers. These were then incubated at 42° C. overnight before being cut into 2 mm×2 mm×1 mm cubes, so that each pellet contained 2 mg estradiol.

ATase Depletion Experiments

Tumours were implanted as previously described and left 3–6 weeks to establish depending on tumour type. An inactivator was homogenized in corn oil at 5 mg/ml before administration by interperitoneal injection (i.p.) or oral gavage (p.o.). Mice were sacrificed at various times up to 72 h and tumours and murine tissues taken for ATase assay. Samples were snap frozen and stored at −20° C. until analysis.

Tumour Sensitization Experiments

O/nu mice were treated with the appropriate dose of the inactivator as indicated (4 mg/ml in corn oil) or the appropriate vehicle as a control 1 hour prior to administration of the appropriate dose of the cytotoxic agent (e.g. temozolomide 6 mg/ml in PBS+20% DMSO) or fotemustine or BCNU (2 mg/ml in PBS+3% ethanol) using the doses and schedules indicated.

Tumour Measurements

Animals were weighed twice weekly and xenograft tumour measurements taken using digital calipers. Tumour volume was calculated using the formula (h×w×l)π/6. Measurements continued until the tumour reached the maximum allowable volume (i.e. 1 cm$^3$). Results were expressed as percentage tumour growth using day 1 tumour volumes as controls.

In the tests on the compounds shown in Table 6 and in FIGS. 9 to 17, the Methods used were as described in WO 94/29312. The following items a) to c) are also to be noted:

a) Standard ATase assay

ATase substrate DNA was prepared by incubation of purified calf thymus DNA with N—[$^3$H]-methyl-N-nitrosourea (18.7 Ci/mmole, Amersham International). Cell or tissue extracts were incubated with [$^3$H]-methylated-DNA substrated (100 μl containing 6.7 μg of DNA and 100fmol of O$^6$-[$^3$H]methylguanine) at 37° C. for 60 mins. Following acid hydrolysis of the DNA as previously described[33] the [$^3$H]-methylated protein was recovered and quantitated by liquid scintillation counting.

b) Drug Treatment

Mice were treated with the inactivator as a suspension in corn oil by intraperitoneal injection (i.p.) or by oral gavage (p.o.) 60 mins prior to temozolomide (100 mg/kg in 20% DMSO in phosphate-buffered saline) which was always given in intraperitoneal injection: this schedule was repeated on days 1 to 5 inclusive. Controls received vehicle alone, inactivator alone or temozolomide alone.

c) Animals

The mice in the tests shown in FIG. 11 and Table 8 were BALB-C derived athymic male mice (nu/nu athymic) from the in-house breeding colony of the Paterson Institute for Cancer Research as described in WO 94/29312 (Animal Services-ASU Mice).

The mice in the tests shown in FIGS. 12–16 were Swiss mouse derived athymic male mice (o/nu athymic) as described above.

The mice in the tests shown in FIG. 17 were DBA$_2$ mice from the in-house breeding colony of the Paterson Institute for Cancer Research (Animal Services Unit), originally from the Jackson Laboratory in 1970.

Test Results

The results of the ATase depletion assay on the compounds of Table 1 are shown in Table 2 or Table 3. Many of the compounds tested were more efficient in inactivating ATase than O$^6$-benzylguanine. In accordance with the results in WO 94/29312 the parent application, compounds in which R is a heterocyclic group were more efficient than the comparable compounds having benzyloxy side chains. In general the compounds in which RCH$_2$ is substituted or unsubstituted thenyl were the most efficient, the most preferred being halo-substituted thenyl having its halo substituent in a 1,3-relationship with the methyleneoxy group attached to the pyrimidine residue.

Tables 3, 4 and 5 summarize data for a number of parameters. Table 3 includes depletion assay results for recombinant ATase of the following types:

```
hAT   = human
mAT   = mouse
rAT   = rat
chAT  = Chinese hamster
ogt   = E. Coli ogt gene
ada   = E. Coli ada gene
```

The combinations of properties for the various inactivators can be seen in the tables. The following surprising points are noted in particular:

B.4316 is a compound of surprisingly high water solubility.

B.4335 is a compound that is unexpectedly much more effective in the inactivation of ATase in Raji cells than of pure recombinant protein: generally, the $I_{50}$ for inactivation of recombinant ATase in vitro is lower or similar to that in cultured cells.

B.4343 is a compound that has a very low $I_{50}$ for ATase in vitro but is not as capable as agents with higher $I_{50}$s (e.g. B.4335) in the sensitization of Raji cells to the growth inhibitory effects of temozolomide. A similar example is B.4351 versus B.4349.

B.4316 was twice as effective as B.4280 but sensitization to temozolomide of Raji cells was almost identical. Thus different cell lines may respond surprisingly differently to these agents.

Figure 2:
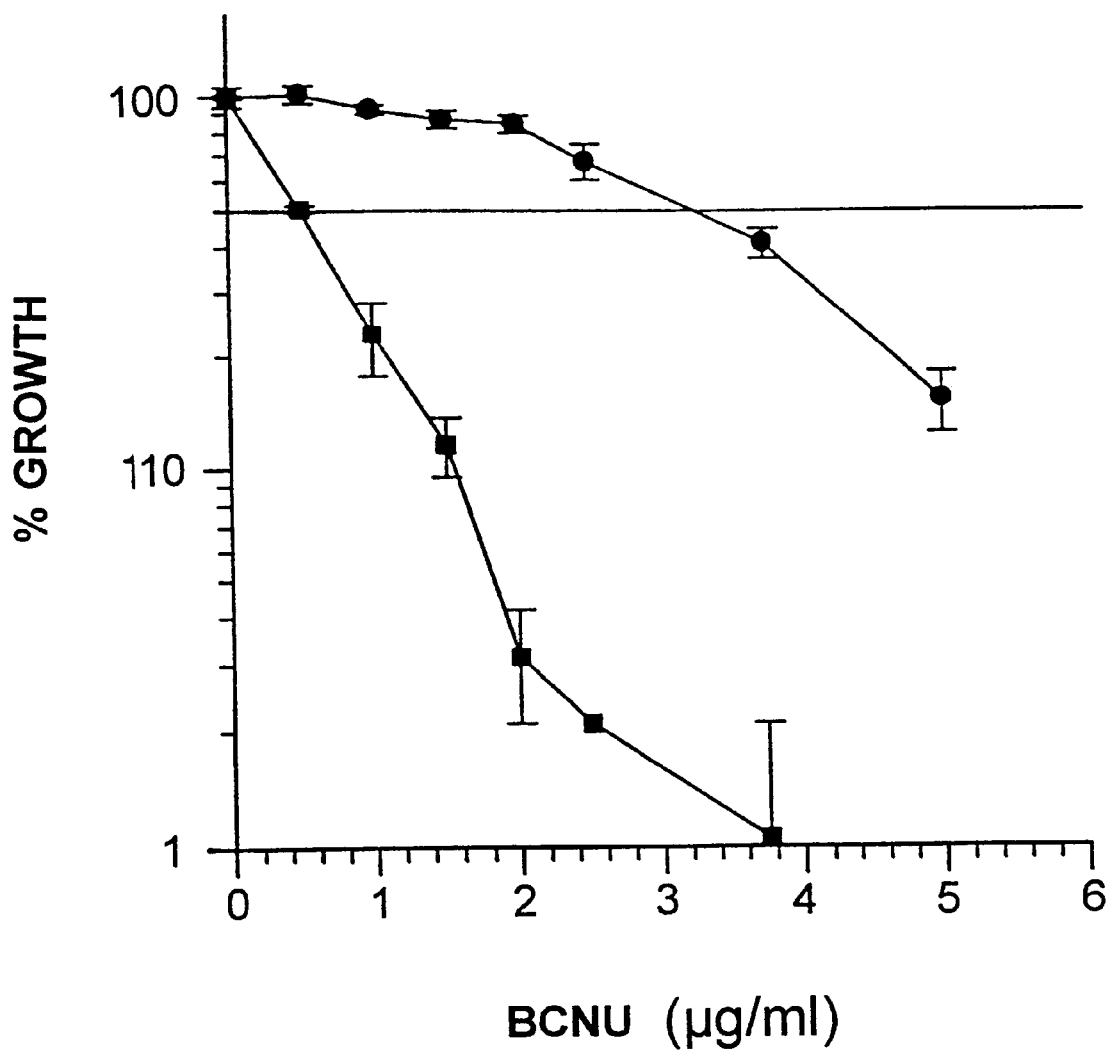
Figure 3:
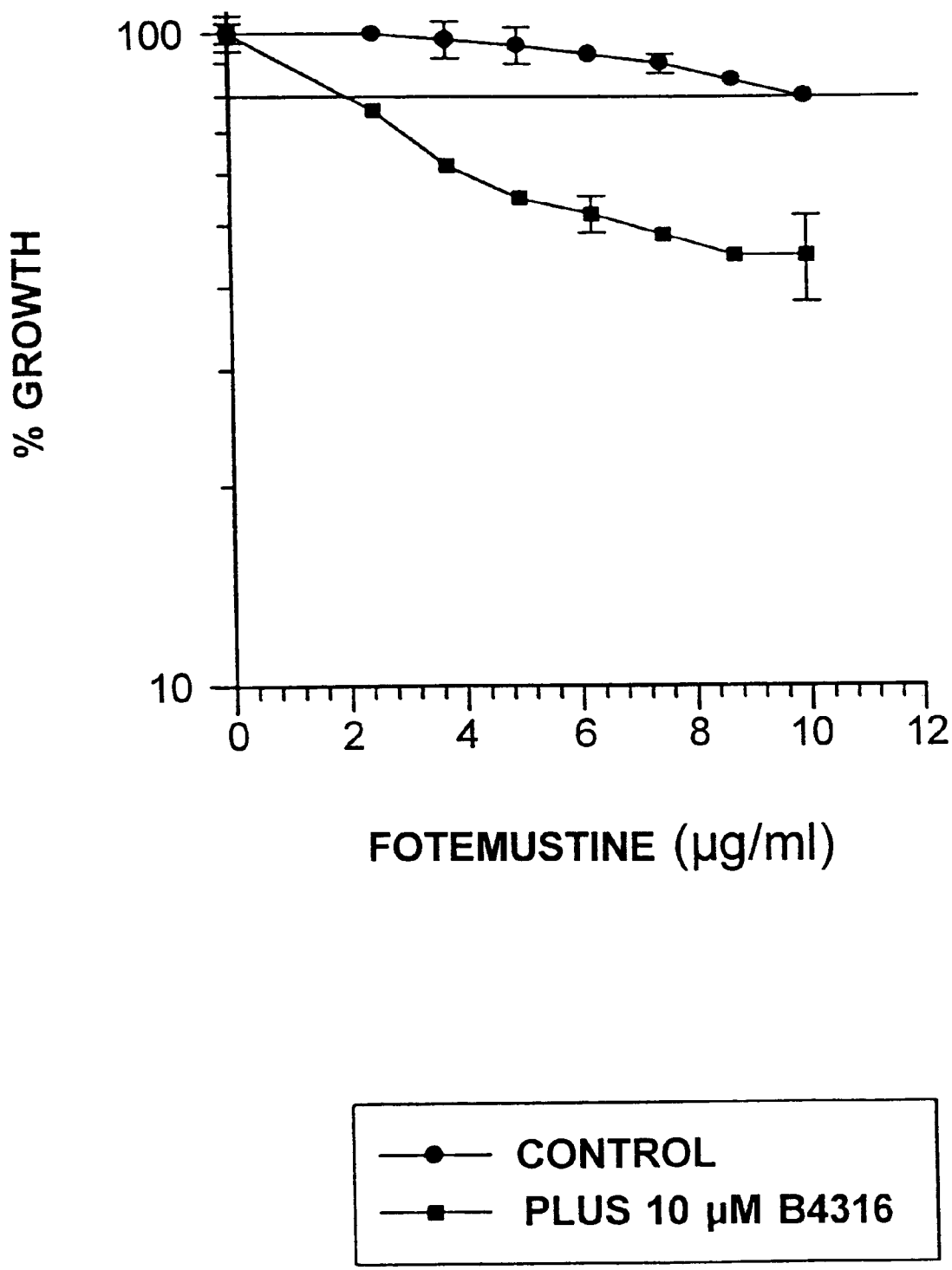
Figure 4:
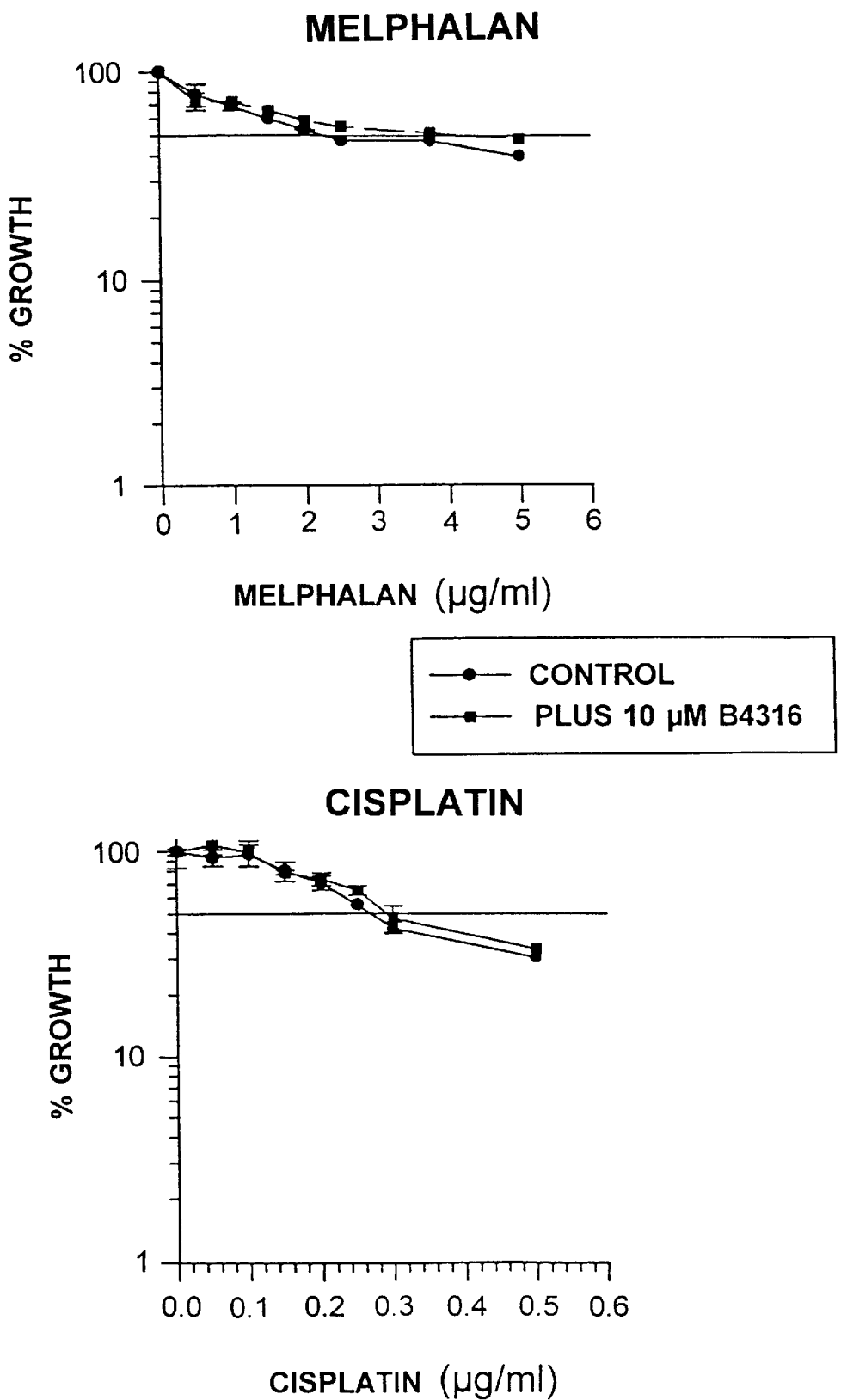

FIGS. 1 to 3 show that temozolomide, BCNU and fotemustine inhibit the growth of Raji cells in a dose-dependent manner but sensitivity is greatly increased by exposure to B.4316 at 0.1, 1.0 and 10 µM respectively. In contrast B.4316 had no measurable effect on growth inhibition of Raji cells by melphalan or cisplatin (FIG. 4). This indicates that the inactivators were specifically sensitizing cells to the $O^6$-alkylating agents and not other classes of alkylating compound.

Figure 5:
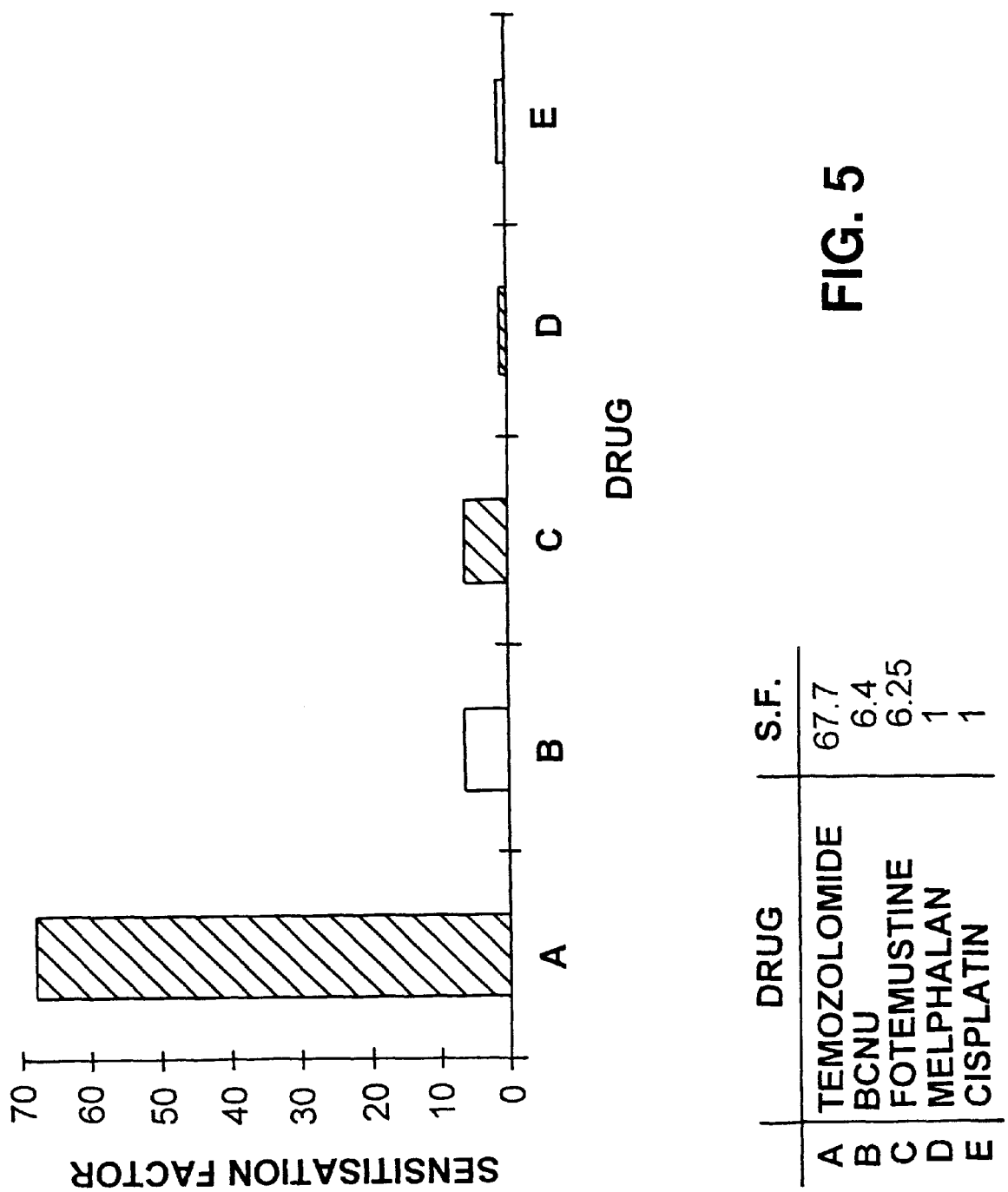
FIG. 5 is a histogram showing the effect of 10 μM B4316 pretreatment on Raji cell sensitization to different chemotherapeutic agents, measured as sensitization factor (SF, defined below) based on $D_{50}$ except for fotemustine where SF is based on $D_{80}$.
Figure 6:
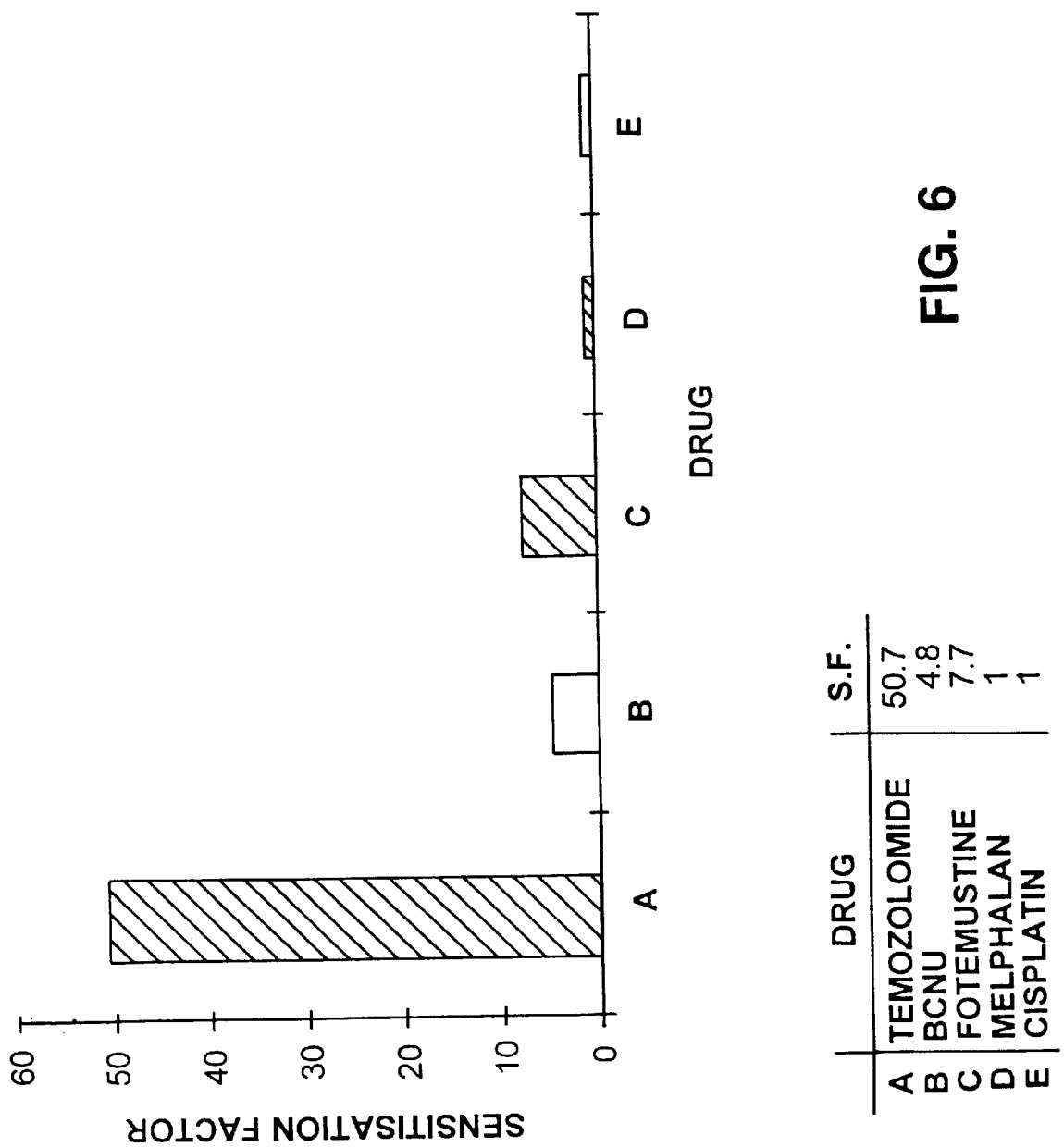
FIG. 6 is a similar histogram showing the effect of 10 μM B4349 pretreatment on Raji cell sensitization to different chemotherapeutic agents, with SF as for FIG. 5.

FIGS. 5 and 6 respectively show the B.4316 and B.4349 sensitization factors for the above therapeutic agents in Raji cells.

Figure 7A:
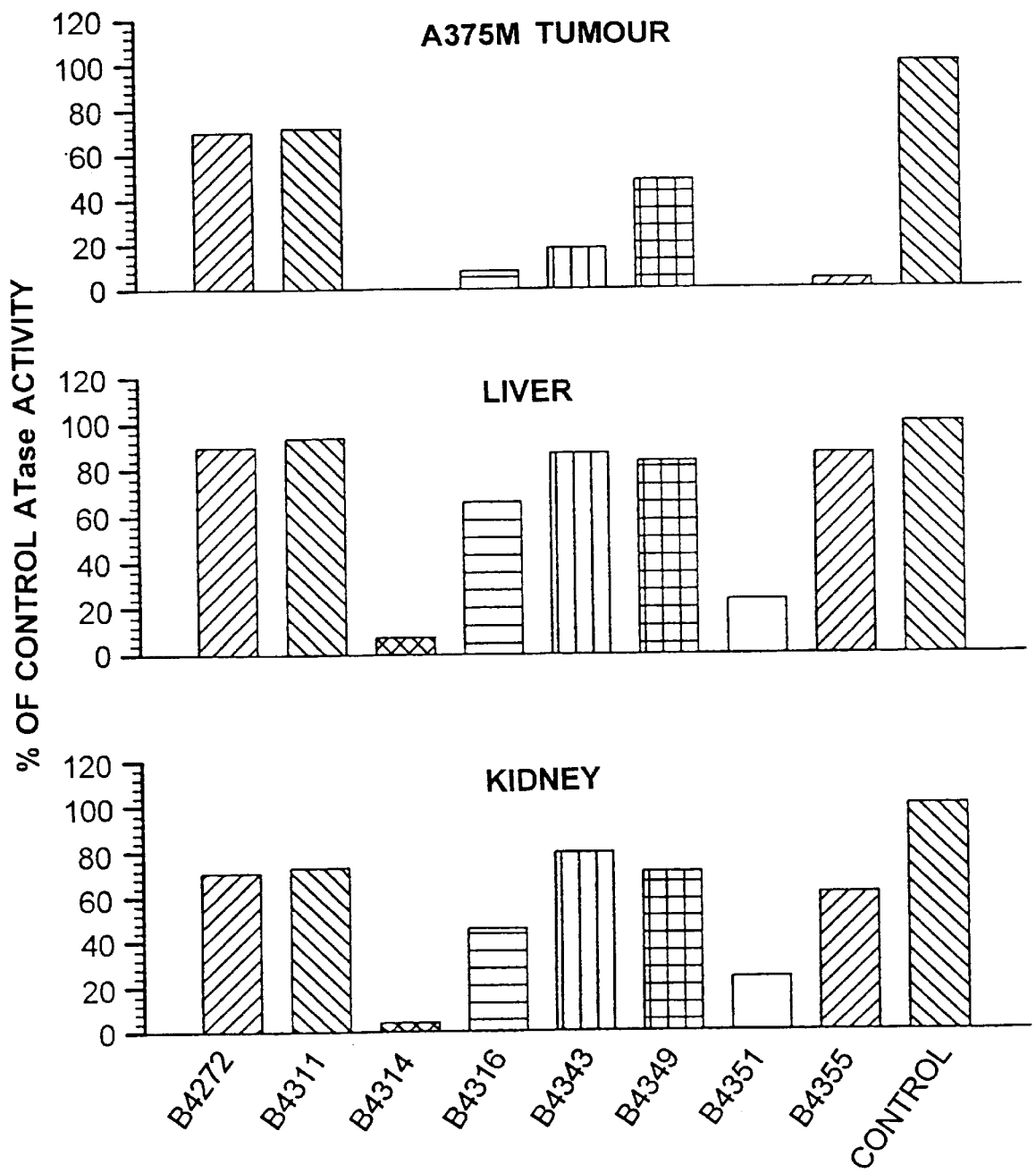
FIG. 7 is a series of histograms showing the inactivation of ATase in A375M tumours and murine host tissues two hours after interperitoneal (i.p.) administration of various inactivator compounds at 5 mg/kg. Inactivation was calculated as % of control ATase activity, measured as fm/mg protein.
Figure 7B:
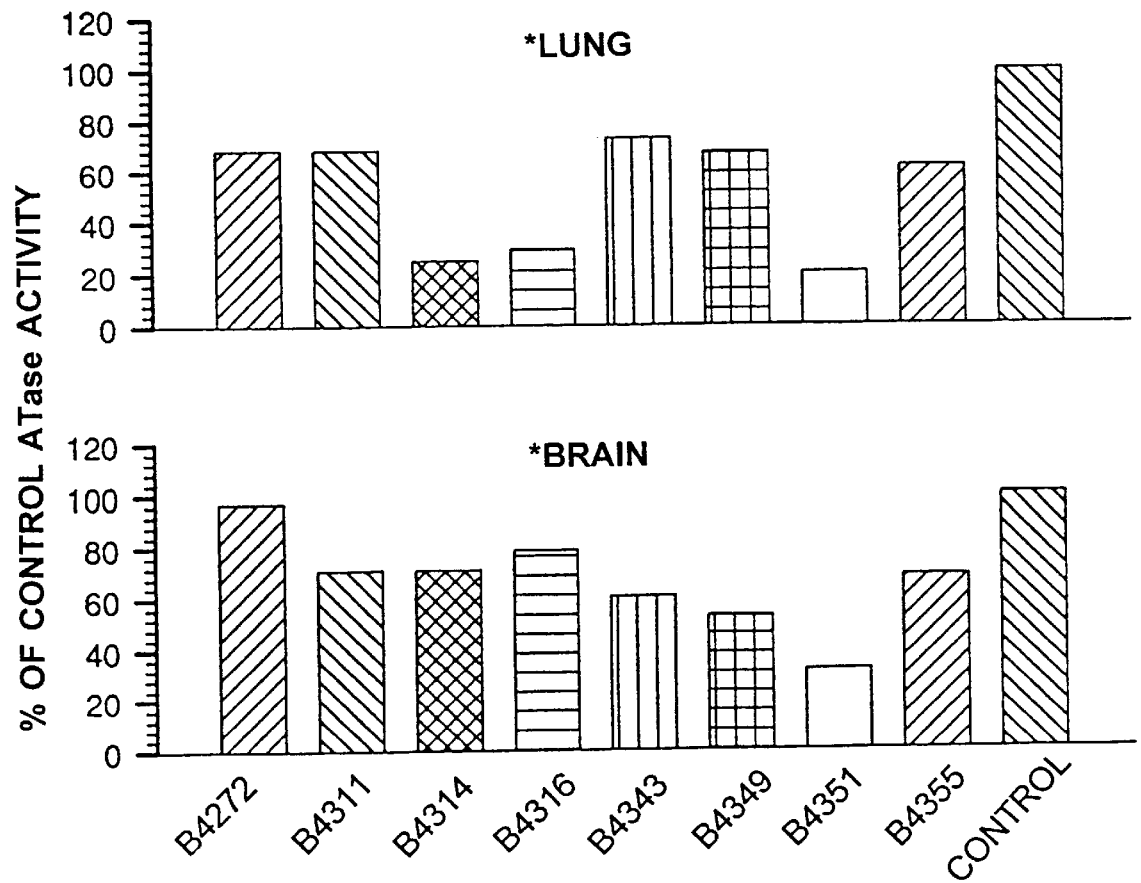

FIG. 7 shows that of the inactivators examined human melanoma xenograft ATase depletion was complete only after administration of B.4314 and B.4351 under the experimental conditions used. The former was more effective in ATase depletion in liver and kidney of host animals whilst the latter was more effective in the brain, suggesting its relative ease in passing the blood-brain barrier. Noteworthy is the fact that whilst B.4311 was one of the most effective agents in sensitizing Raji cells to the toxic effects of temozolomide, it was surprisingly one of the least effective agents in depleting mouse tissue or tumour xenograft ATase activity.

Figure 8:
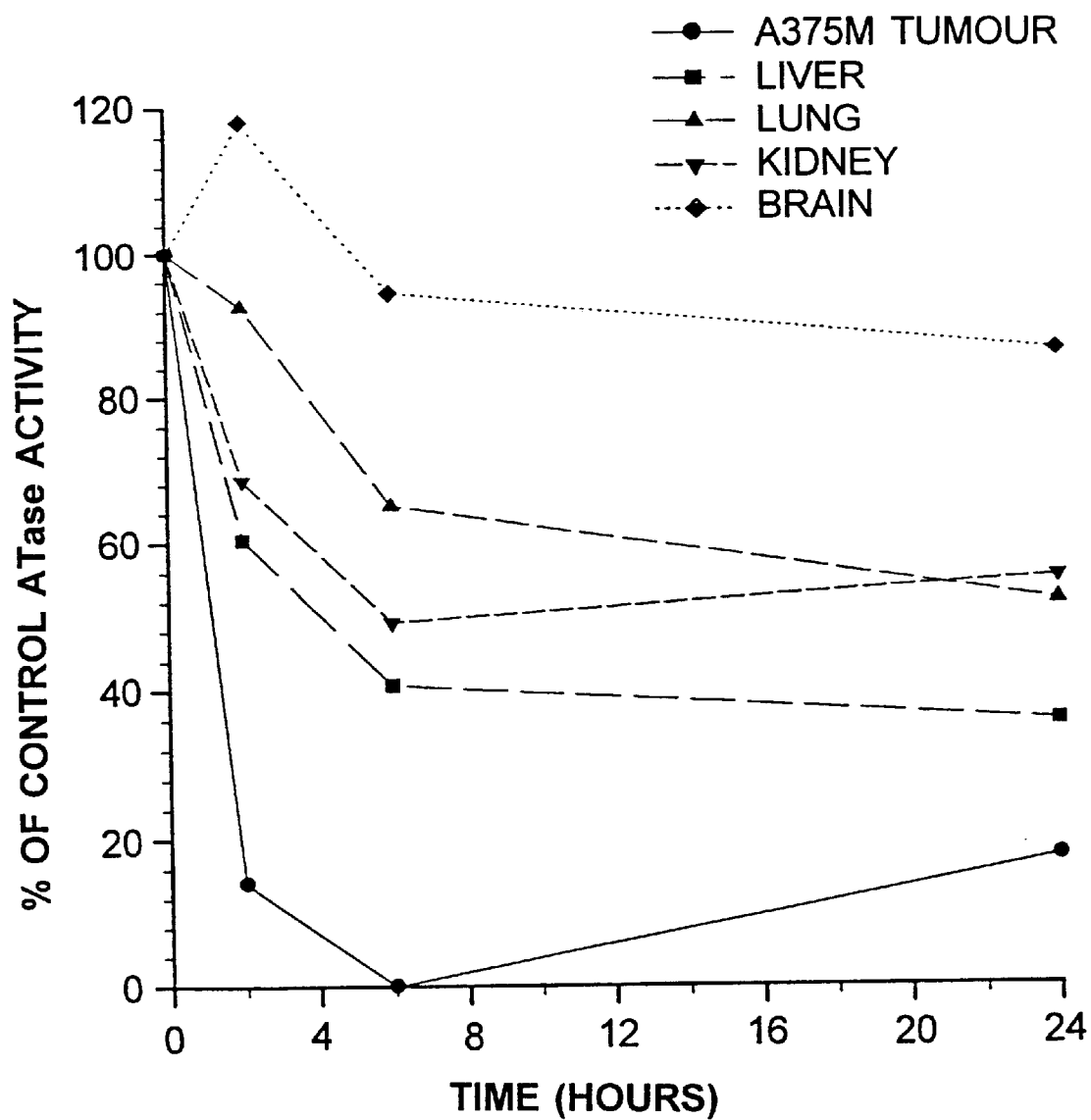
FIG. 8 is a graph showing the kinetics of ATase depletion and recovery in A375M tumours and murine host tissues after administration of B.4363 (20 mg/kg i.p.). The graph plots % of control ATase activity against time (hours).

FIG. 8 shows that B.4363 depletes ATase more effectively in human melanoma xenografts than in murine host tissues under the conditions used: relatively little effect was seen in brain tissue, suggesting its poor ability to cross the blood brain barrier.

The test results for the compounds of Table 6 (and some in Table 1) are shown in Table 7 and FIGS. 9 to 27.

B.4280, which is $O^6$-(4-bromothenyl)guanine and has its bromo substituent in a 1, 3-relationship with the methylene group attached to the guanine residue, was more efficient in inactivating ATase in vitro than its 5-bromo analogue B.4269, in which the bromo substituent is in a 1, 4-relationship with the methylene group. Both B.4280 and B.4269 were more efficient than the unsubstituted thenyl derivative B.4205 despite having considerably larger $O^6$ substituents.

Another preferred compound is B.4317 which is $O^6$-(4-cyanothenyl)guanine. B.4317 is a more efficient inactivator in vitro than its 5-cyano analogue B.4283 or the unsubstituted thenyl derivative B.4205.

Figure 9:
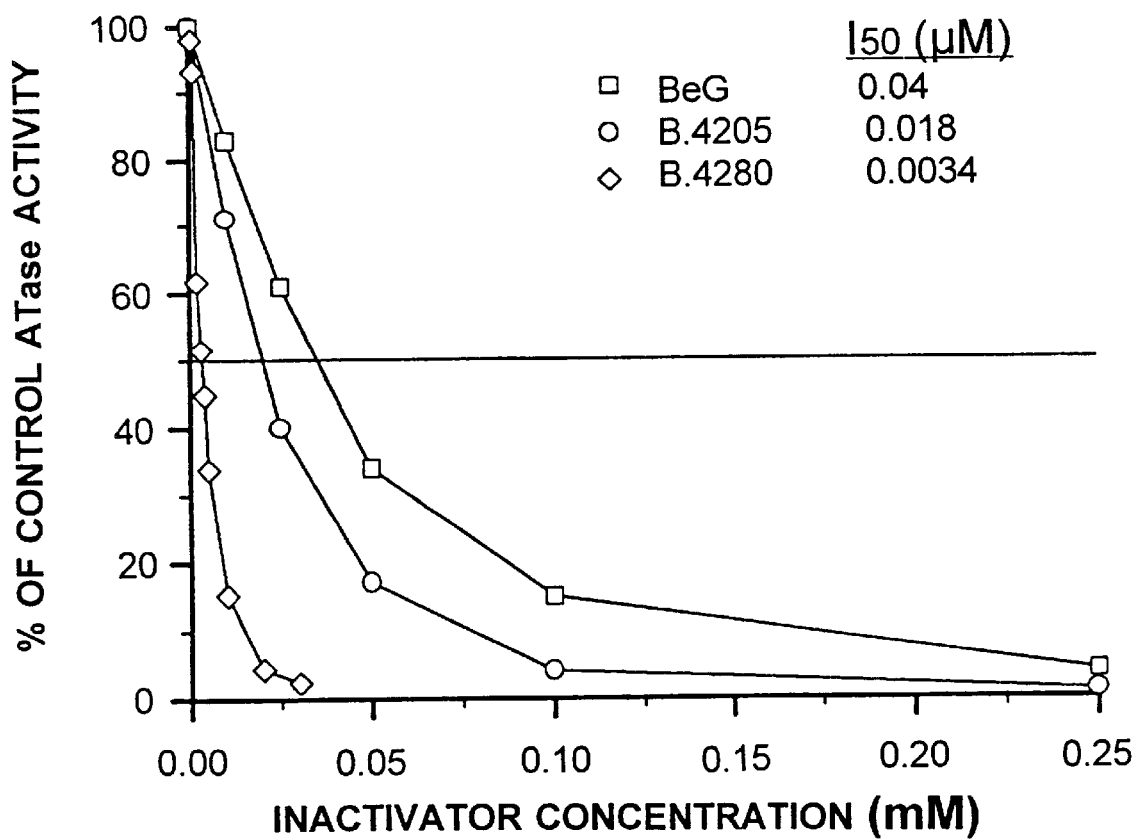
FIG. 9 is a graph of percentage residual activity of pure recombinant human ATase following incubation with increasing concentrations of inactivators $O^6$-benzylguanine (BeG), $O^6$-thenylguanine (B.4205) and $O^6$-(4-bromothenyl) guanine (B.4280). The line at 50% residual activity is used for calculating $I_{50}$ values i.e. the concentration of inactivator required to produce a 50% reduction in ATase activity. The $I_{50}$ values shown are extrapolated from the curves. Preincubation was for 1 hour after which [$^3$H]-methylated substrate was added to determine residual activity of ATase.

Typical ATase inactivation profiles for BeG and B.4205 and B.4280 are shown in FIG. 9.

Figure 10:
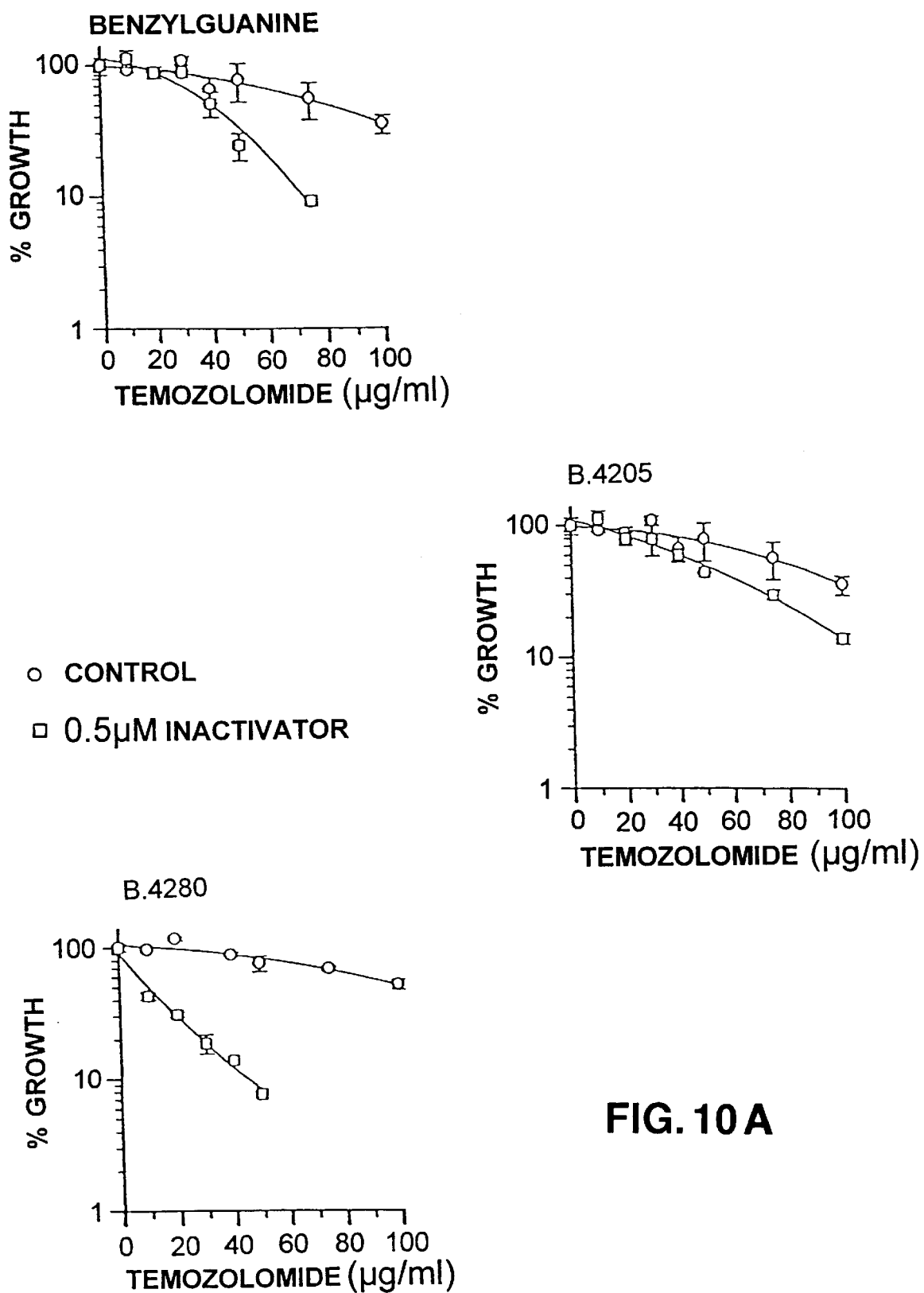
FIG. 10A is three graphs of percentage cell growth against temozolomide concentration (μg/ml) showing the effect of pretreatment with BeG, B.4205 and B.4280 (0.5 μM final concentration) on the sensitivity of Raji cells to the growth inhibitory effects of temozolomide. Inactivator or vehicle was given 2 hours prior to temozolomide.
FIG. 10B is a histogram for the inactivators of FIG. 10A showing the sensitization factor based on $D_{50}$ of Raji cells to growth inhibition by temozolomide.
Figure 10:
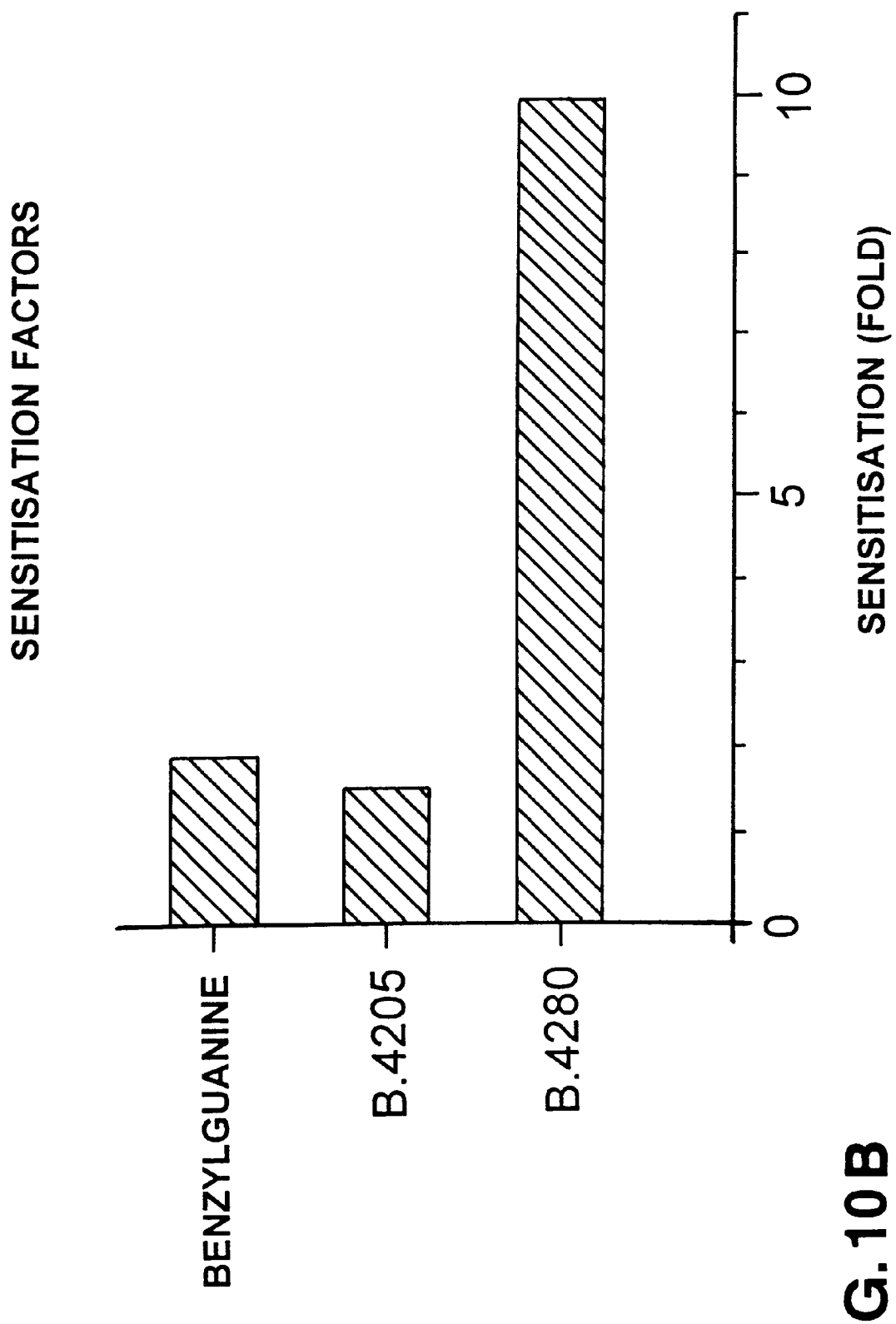

The inactivation of ATase resulted in the sensitization of Raji cells to the growth inhibitory effects of temozolomide (FIG. 10). B.4280 was considerably more effective than either B.4205 or BeG in this respect.

ATase in human melanoma xenografts was inactivated by BeG, B.4205 and B.4280 (FIG. 11) with some indication that the rates of recovery of ATase activity were different between the agents. B.4280 was the most effective in vivo inactivator at the doses examined.

B.4280 was able to inactivate ATase in most tissues as shown in Table 8. Thus, activity in brain, testis and bone marrow was near to control levels by 24 hours whereas lung and spleen activity had not completely recovered by 48 hours. Tumour activity was very low at 24 hours but had recovered completely by 48 hours. Differential recovery rates might be an important factor in the toxicity of ATase inactivators when used in combination with CNU or temozolomide.

Figure 12:
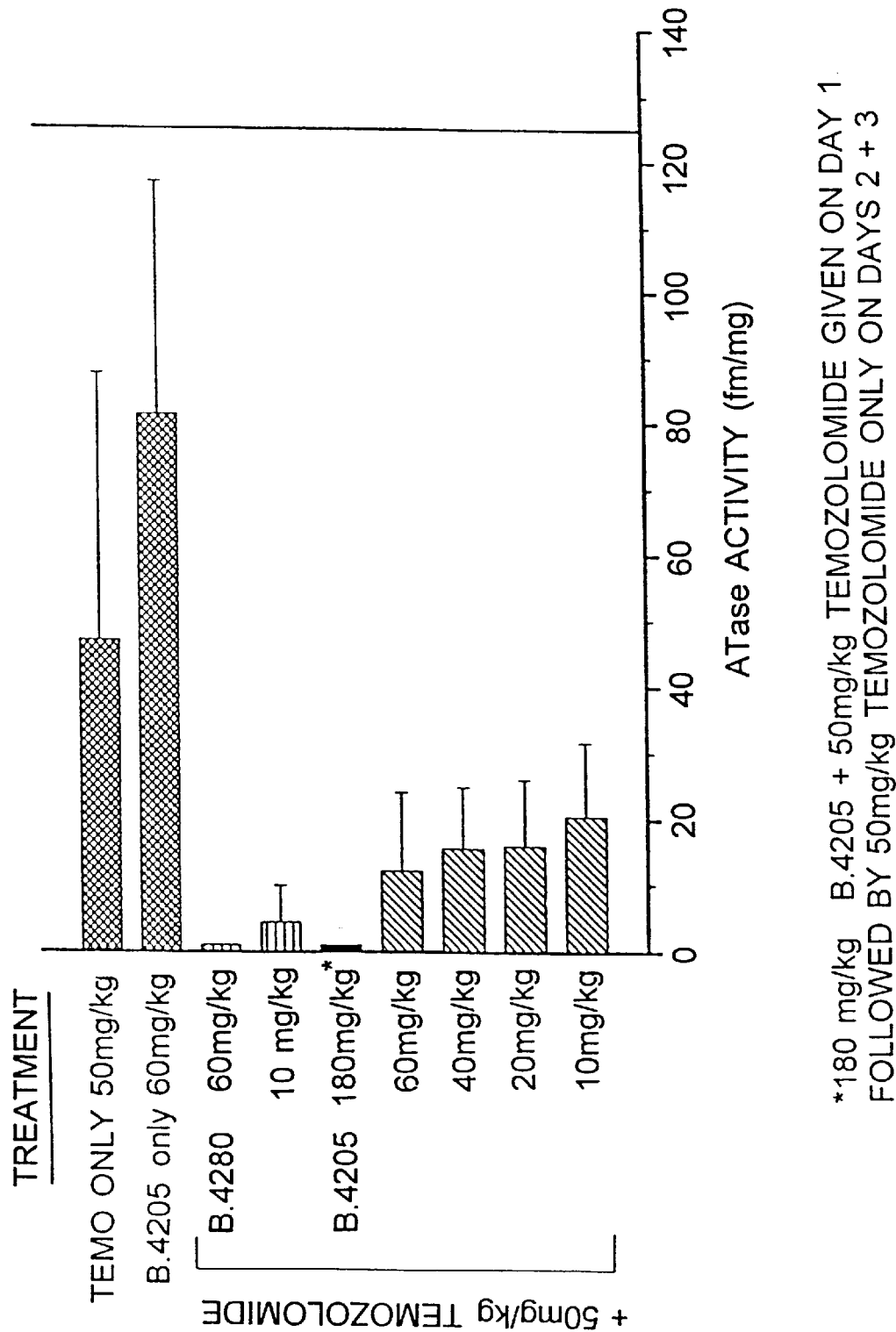
FIG. 12 is a histogram showing the effect of ATase inactivators on ATase activity (fm/mg) inhuman melanoma xenografts grown in nude mice. Animals were given B.4205 or temozolomide alone or B.4205 or B.4280 in combination with temozolomide (50 mg/kg) i.p. at the does shown on three consecutive days (except where indicated) and sacrificed 24 hours after the final dose. The vehicles were corn oil for the inactivators and PBS (20% DMSO) for temozolomide.
Figure 13:
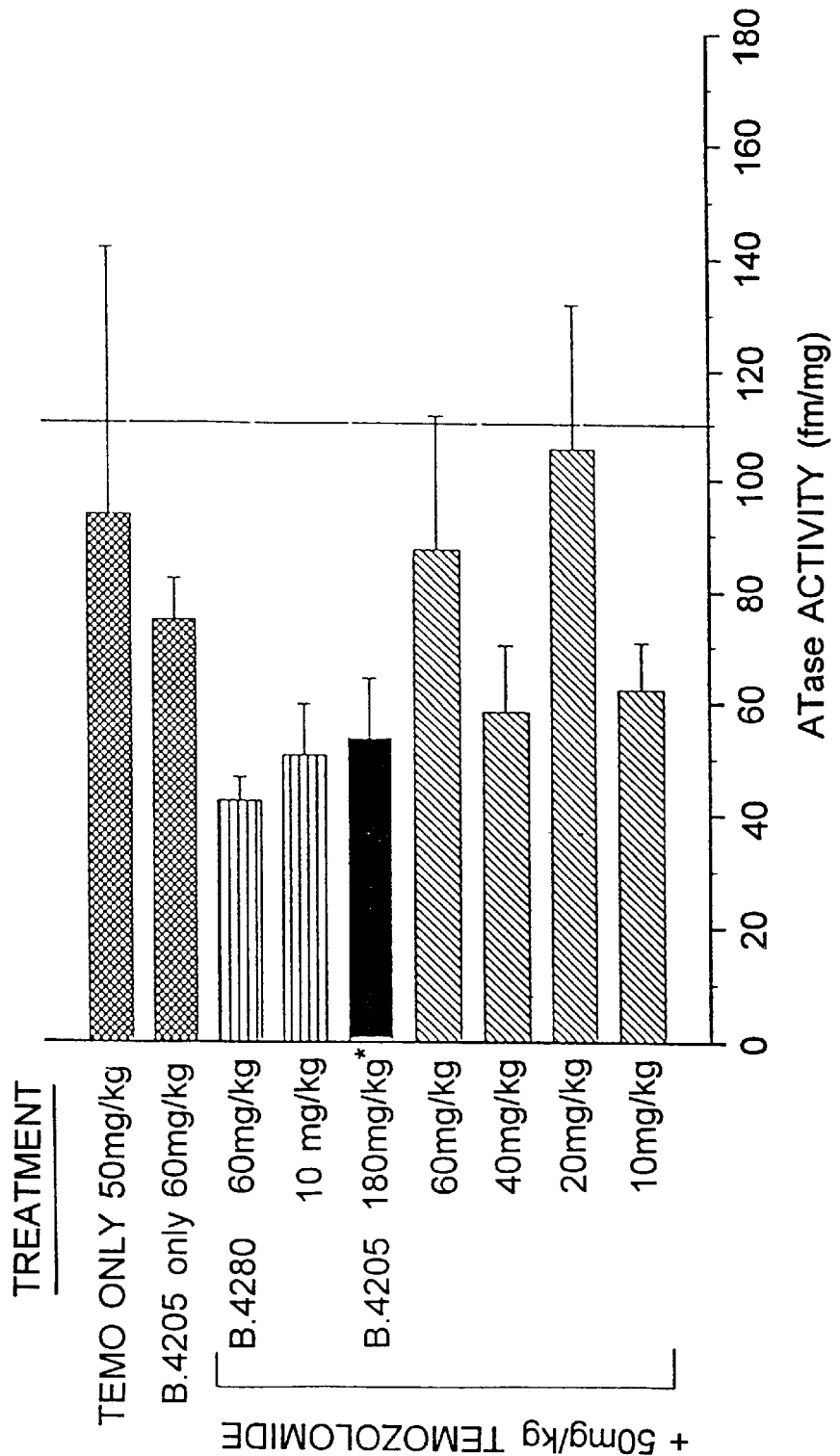
FIG. 13 is a histogram showing the effect of ATase inactivators on ATase activity in livers of nude mice. Animals were given the B.4205 or temozolomide alone or B.4205 or B.4280 in combination with temozolomide (50 mg/kg, i.p.) at the doses shown on three consecutive days (except where indicated) and sacrificed 24 hours after the final dose.

Combination of B.4205 or B.4280 and temozolomide given over three days were more effective in ATase inactivation in tumour xenografts than either agent alone (FIG. 12). Decreasing the dose of B.4205 had no major effect on the ability of the agent to inactivate ATase, 10 mg/kg being as effective as 60 mg/kg. B.4280 was more effective than B.4205 at equivalent doses. As before (FIG. 11) there was some indication that ATase recovery was less efficient in the tumour xenograft (FIG. 12) than in the liver (FIG. 13).

Figure 14A:
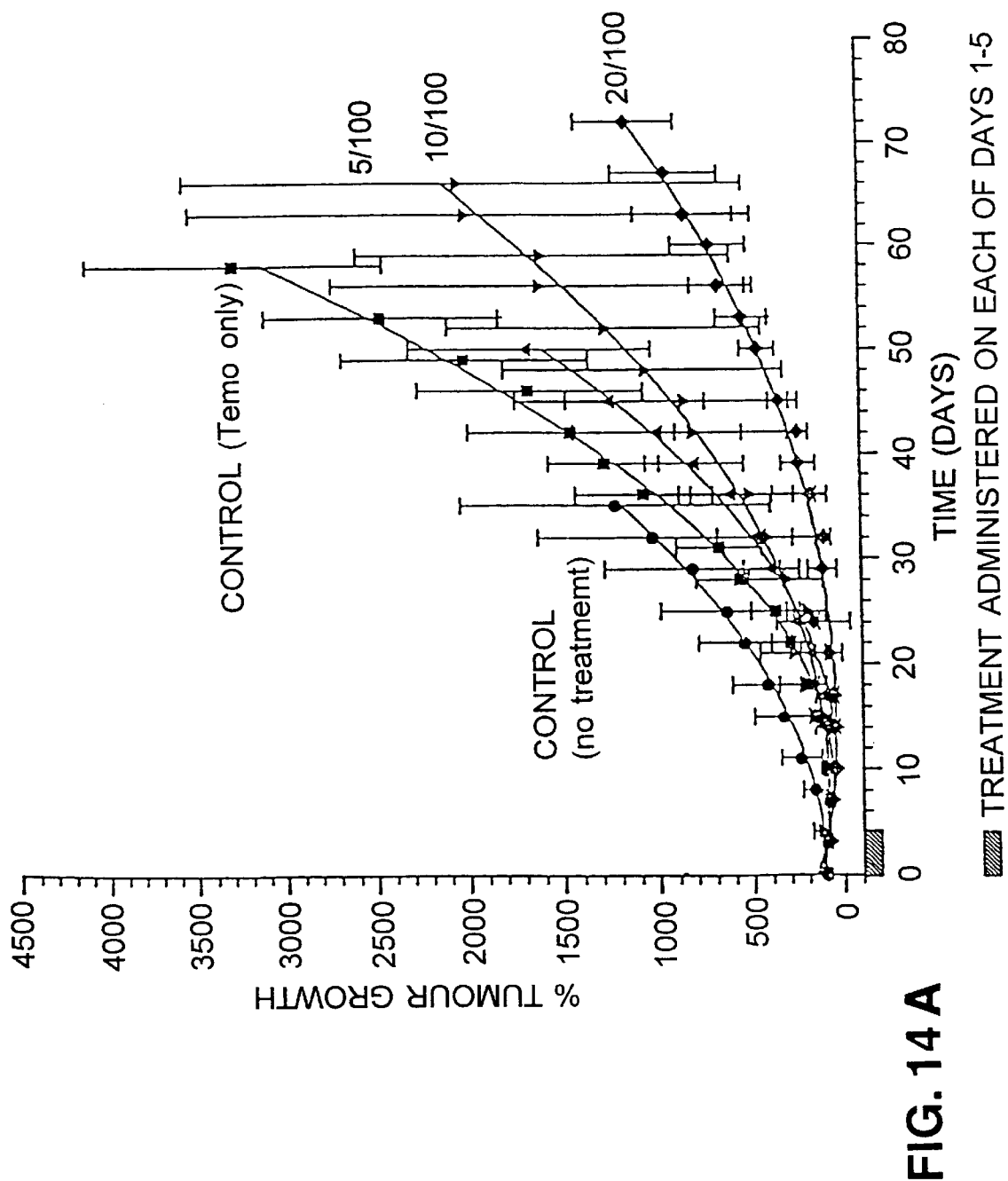
FIG. 14A is a graph of % tumor growth against time (days) showing the effect of B.4205 on the sensitivity of human melanoma xenografts to growth inhibition by temozolomide. Animals were untreated, given temozolomide alone (100 mg/kg, i.p.) or B.4205 (5, 10 or 20 mg/kg i.p.) followed 1 hour later by temozolomide (100 mg/kg, i.p.) on five consecutive days. Tumour growth was monitored as described. The data from a number of separate studies are presented.
Figure 14B:
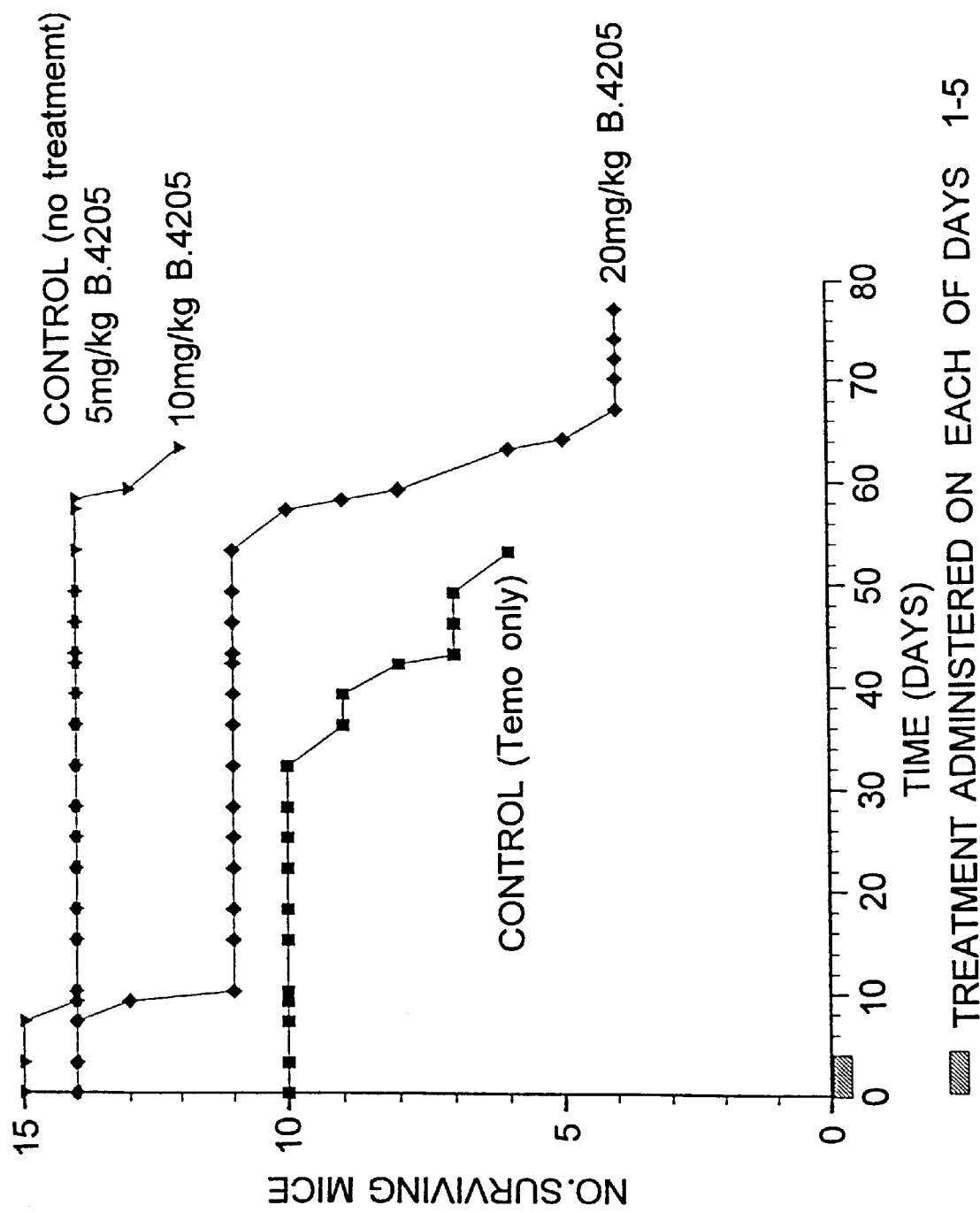
FIG. 14B is a graph of number of surviving mice against time (days) showing survival of animals (tumour-bearing nude mice) used in the study shown in FIG. 14A. Groups of animals in which the xenografts had reached the maximum size were terminated.
Figure 15A:
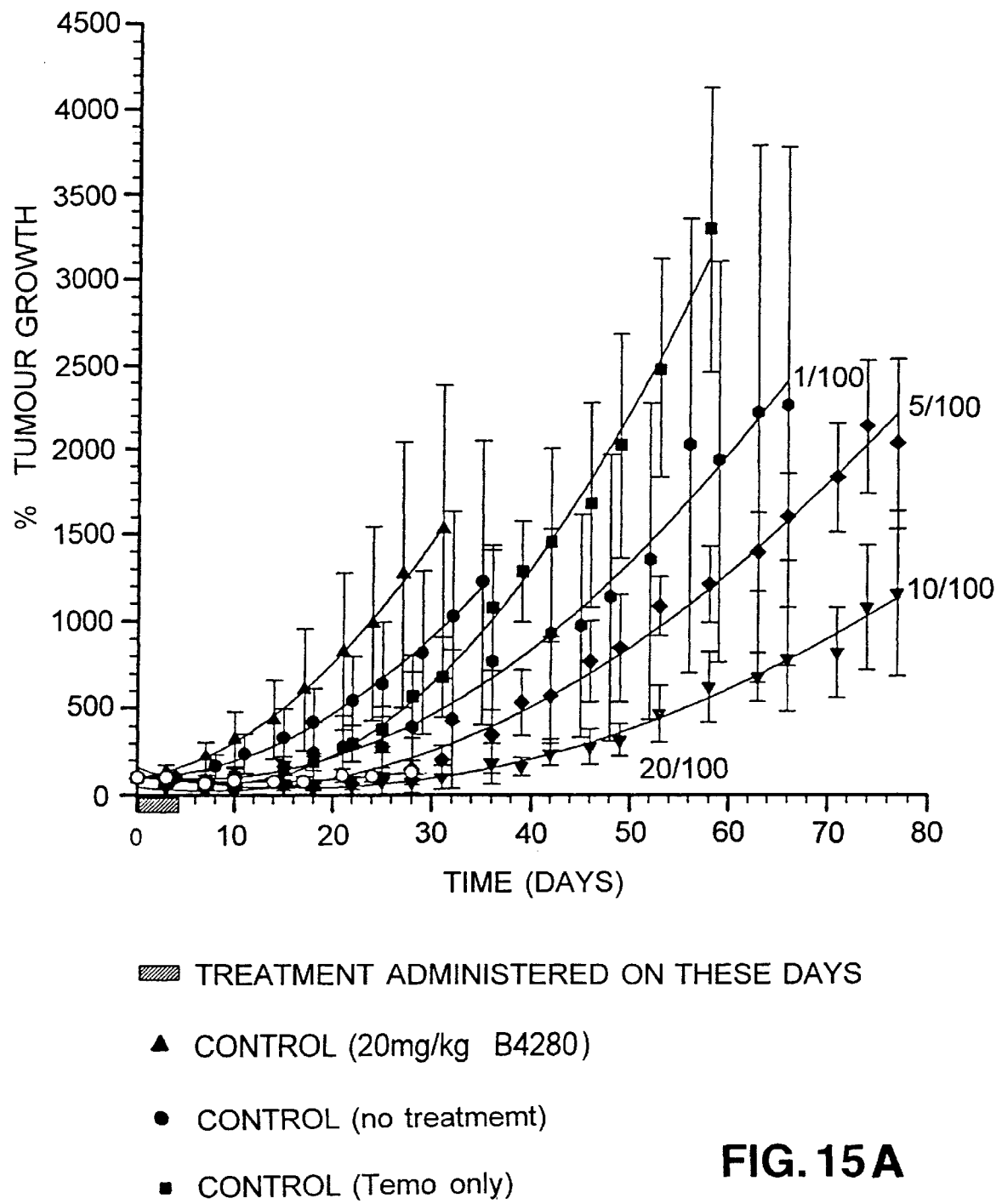
FIG. 15A is a graph showing the effect of B.4280 on the sensitivity of human melanoma xenografts to growth inhibition by temozolomide. Animals were untreated, given temozolomide alone (100 mg/kg. i.p.) or B.4280 alone (20 mg/kg, i.p.) or B.4280 (1, 5, 10 or 20 mg/kg, i.p.) followed 1 hour later by temozolomide (100 mg/kg, i.p.) on five consecutive days. Tumour growth was monitored as described. The data from a number of separate studies are presented.
Figure 15B:
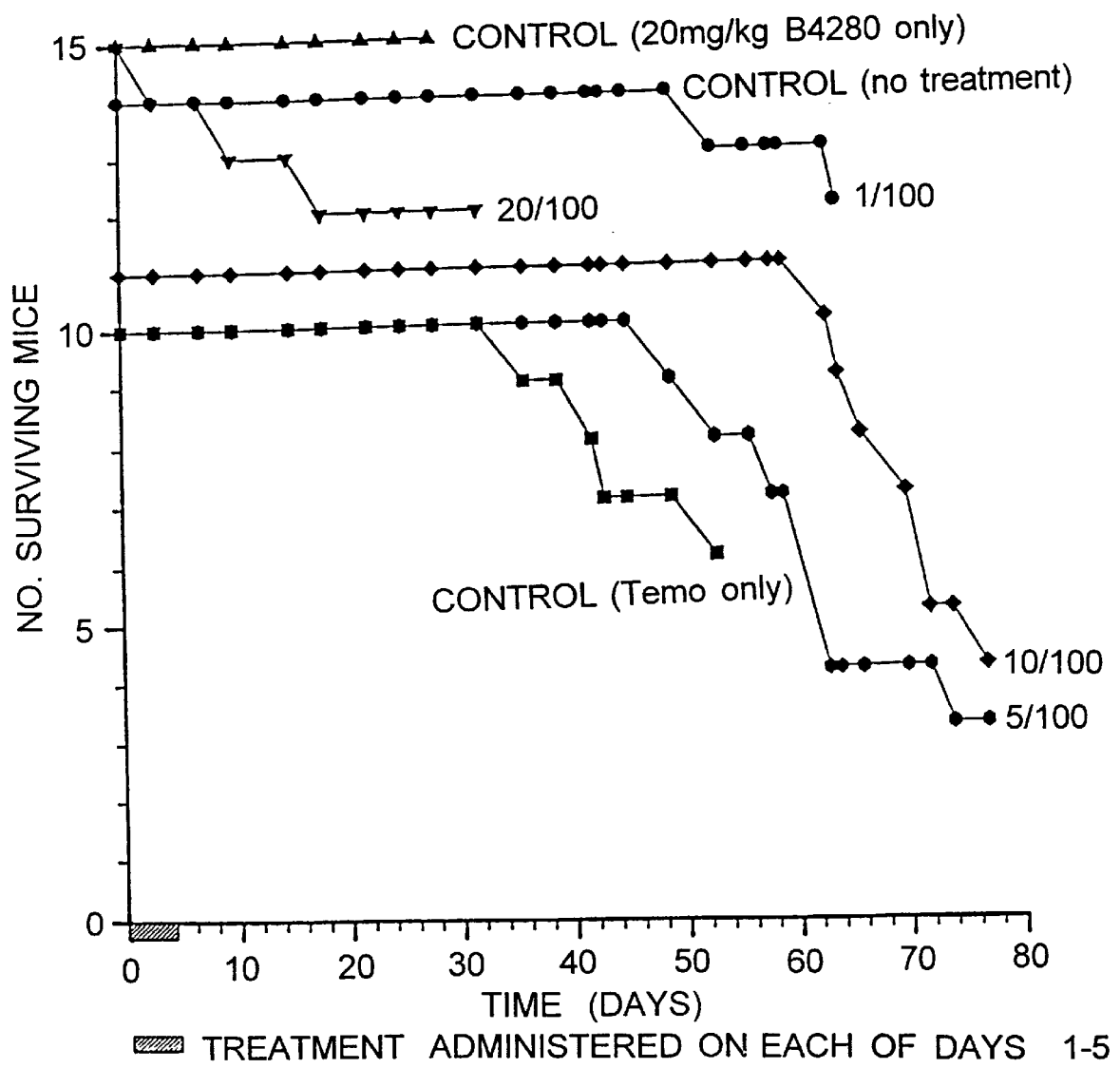
FIG. 15B is a graph showing the survival of the animals (tumour-bearing nude mice) used in the study shown in FIG. 15A. Groups of animals in which the xenografts had reached the maximum size were terminated.

B.4205 (FIG. 14A) and B.4280 (FIG. 15A) were effective in sensitizing human melanoma xenografts to the growth inhibitory effects of temozolomide. A comparison of the two sets of data indicates that B.4280 was about twice as effective as B.4205 in this respect. At equi-effective doses for tumour growth inhibition, B.4280 seems to be less toxic than B.4205 (FIGS. 14B and 15B).

Figure 16A:
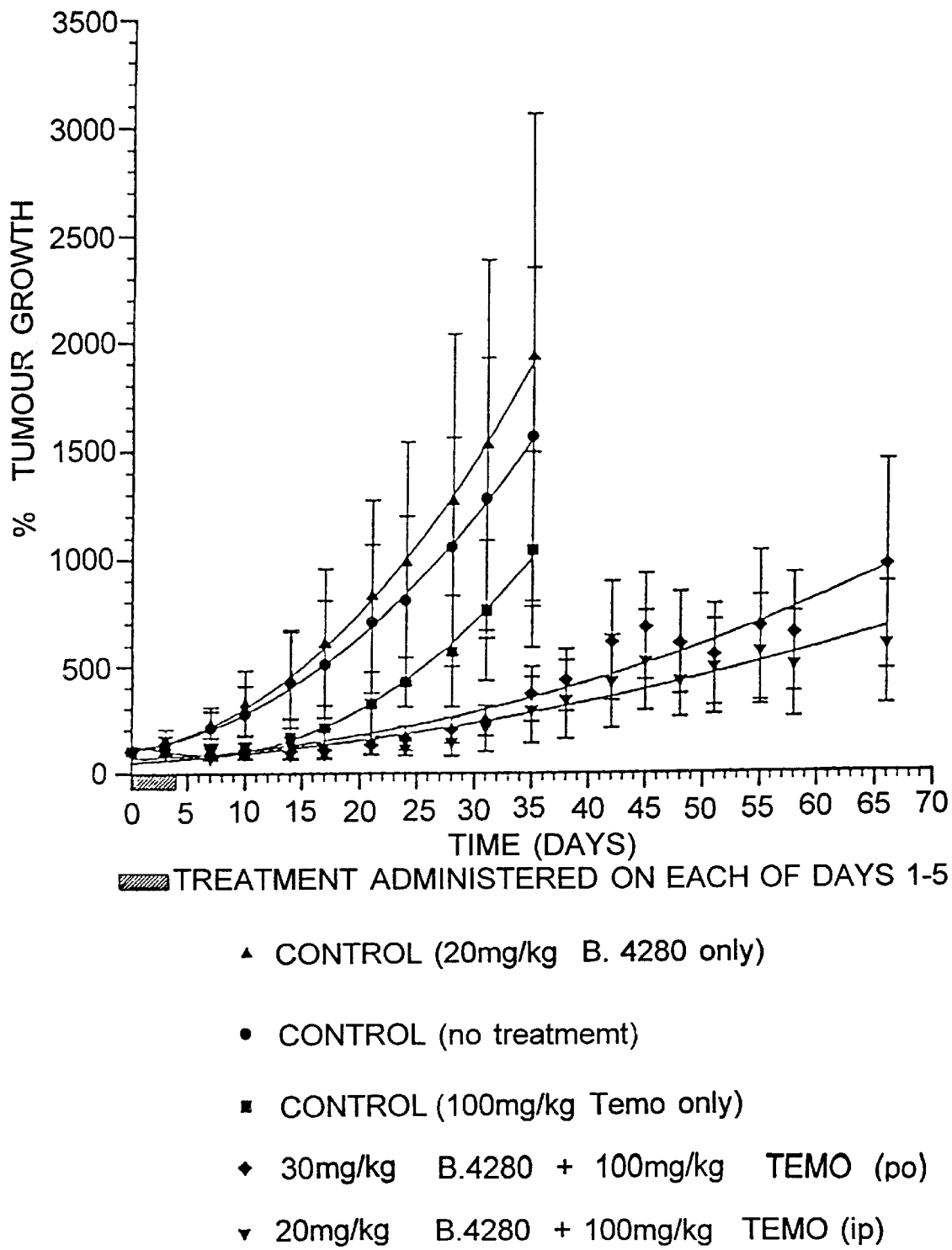
FIG. 16B is a graph showing the survival of the animals used in the study shown in FIG. 16A. Groups of animals in which the xenografts had reached the maximum size were terminated.
Figure 16:
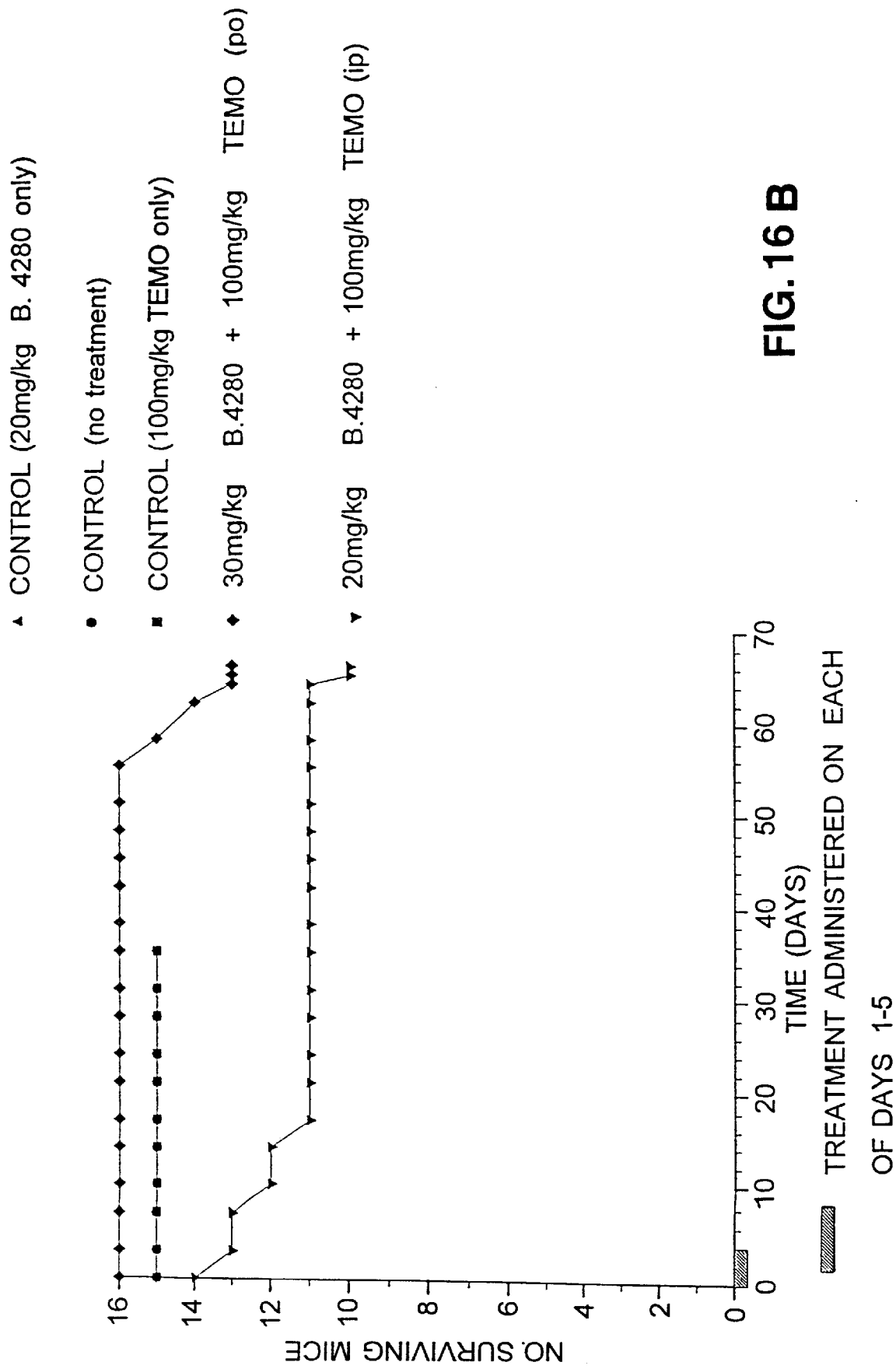

In experiments using $DBA_2$ mice in combination with BCNU, B.4280 was considerably less acutely toxic than B.4205 or BeG as shown in Table 9. Oral administration of B.4280 was shown to be almost as effective as i.p. administration in sensitizing human melanoma xenografts to the growth inhibitory effects of temozolomide (FIG. 16A). Furthermore the oral combination appeared to be marginally less toxic than the i.p. route (FIG. 16B).

At a dose of 20 mg/kg of inactivator in combination with temozolomide in $DBA_2$ mice, B.4205 and B.4280 were shown to be less acutely toxic than BeG, with B.4280 being less acutely toxic than B.4205 (FIG. 17).

Figure 18:
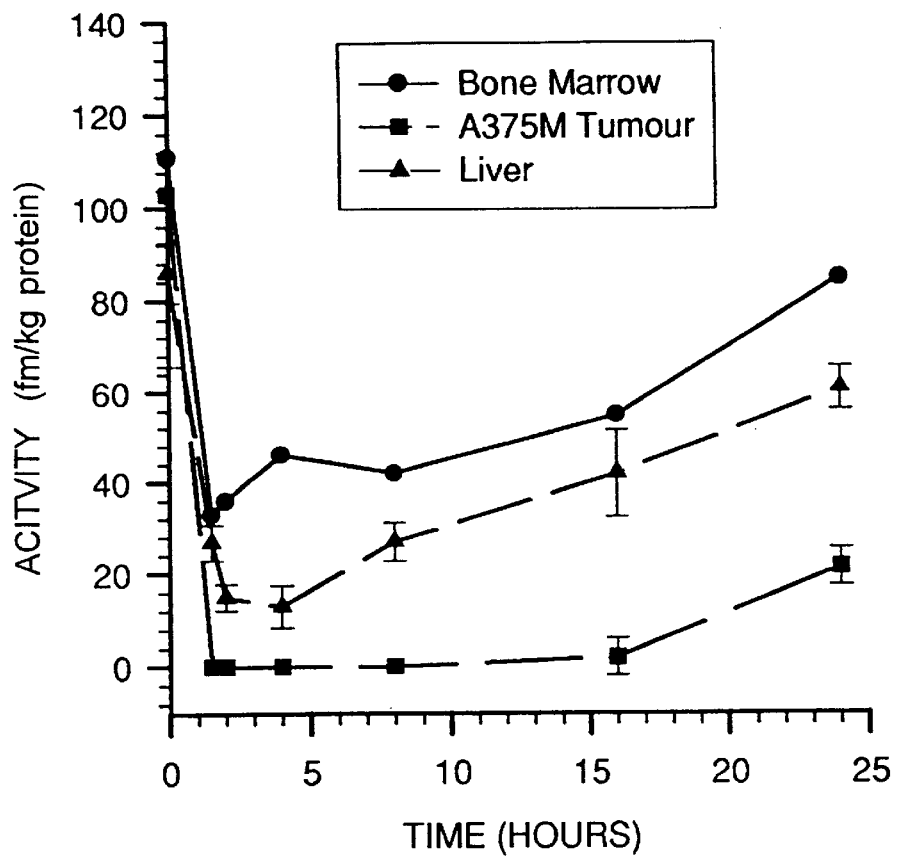
FIGS. 18 to 21 consist of pairs of graphs showing the kinetics of ATase depletion and recovery in various tumours and murine host tissues after administration of B.4280 at the doses indicated. The graphs plot ATase activity (fm/mg protein) and % of control ATase activity against time (hours)
Figure 18:
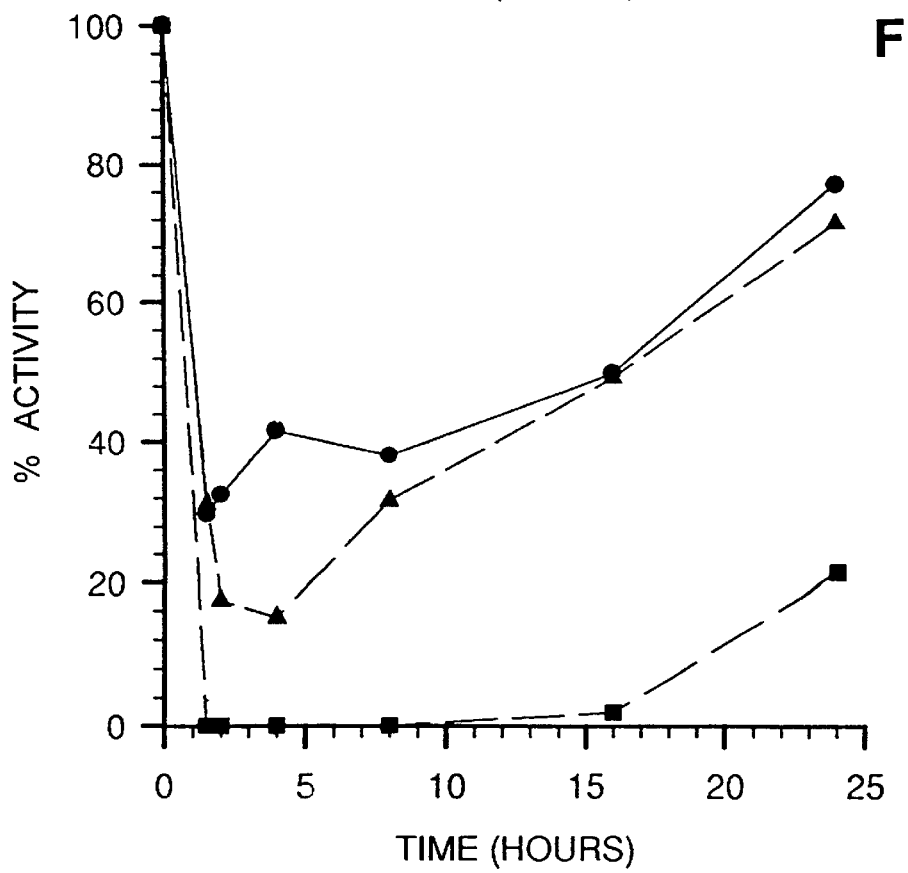
Figure 19:
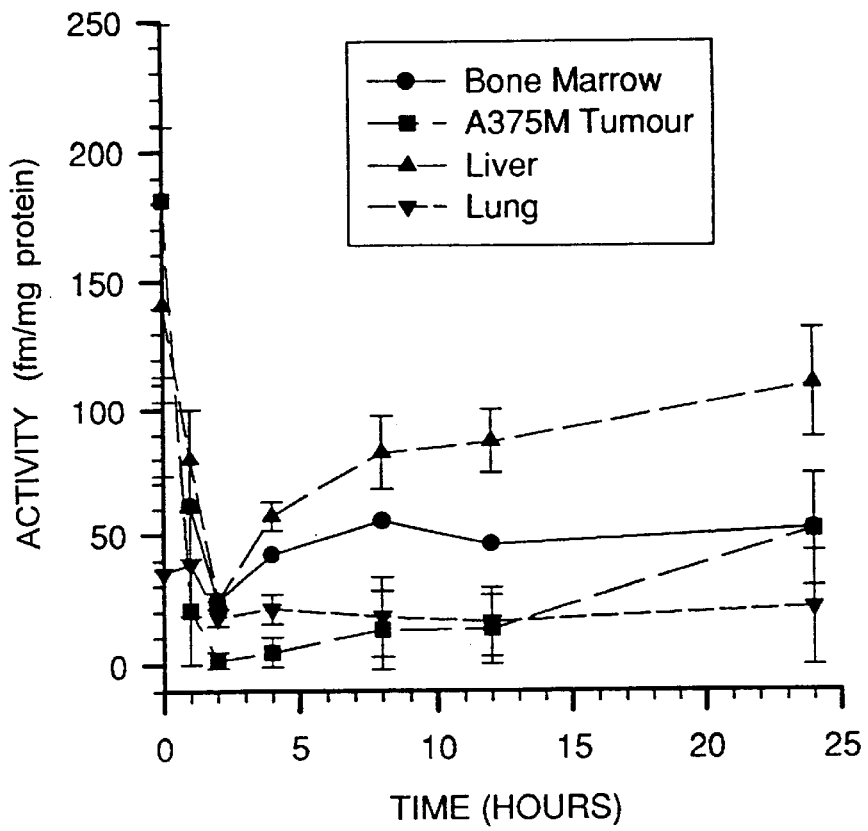
Figure 19:
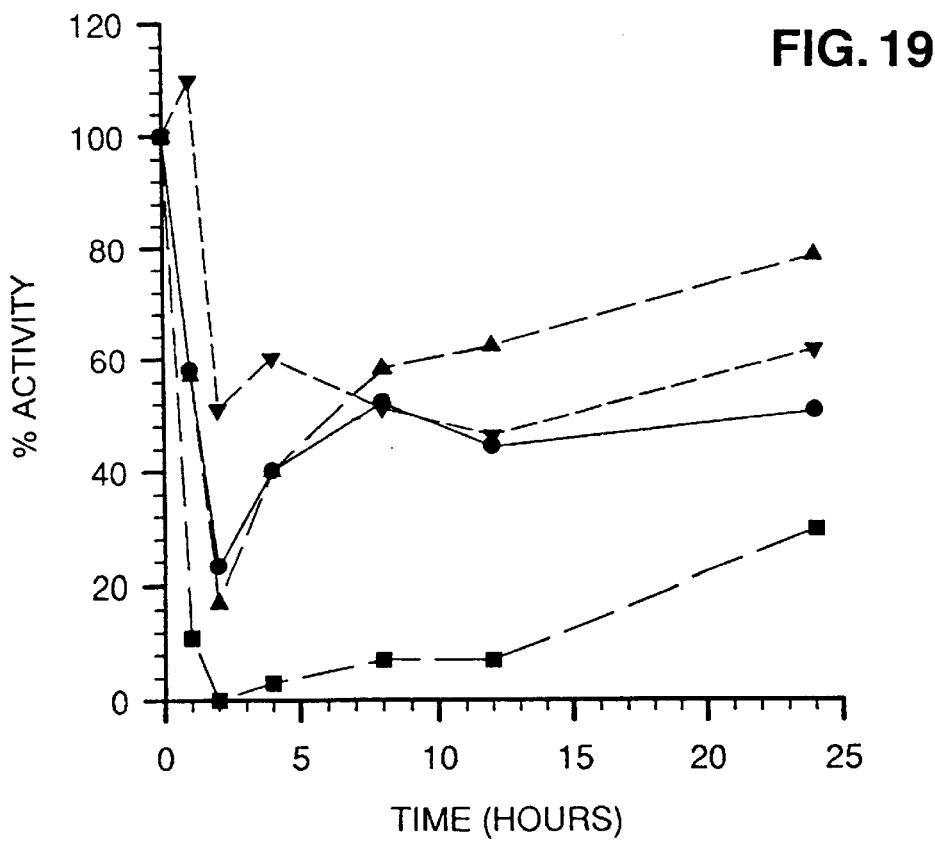

FIGS. 18 and 19 show that B.4280 (PaTrin-2) (i.p. at 20 mg/kg and p.o. at 30 mg/kg respectively) depletes ATase in human melanoma xenografts more completely and for a more extensive period than it does in host tissues.

Figure 20:
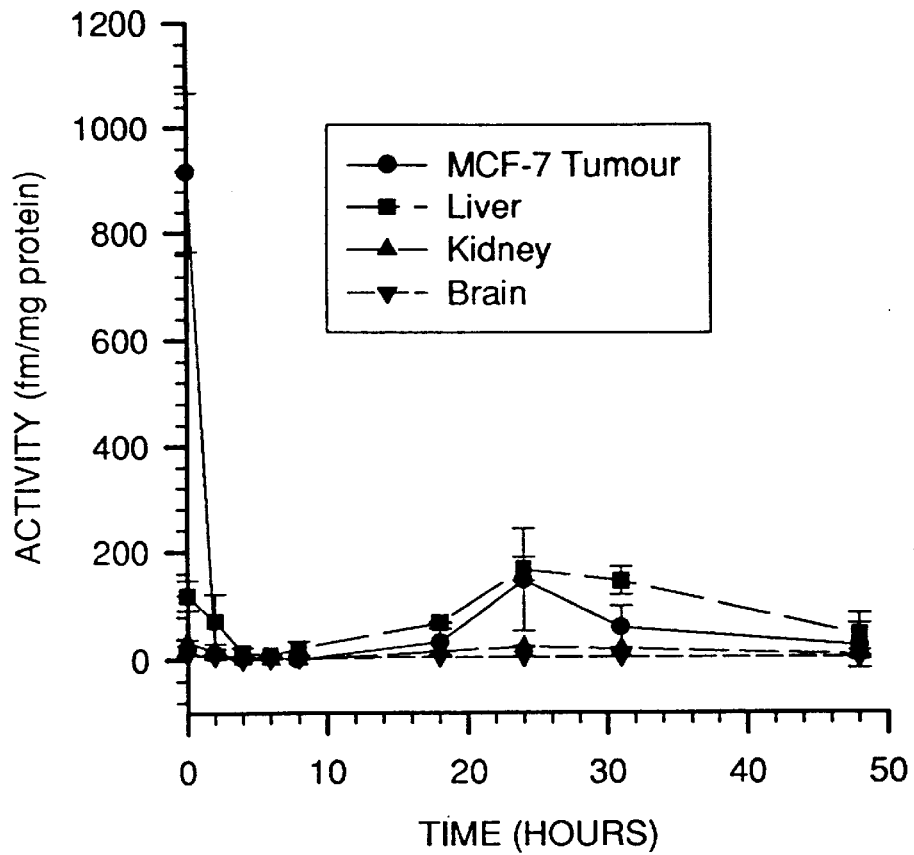
Figure 20:
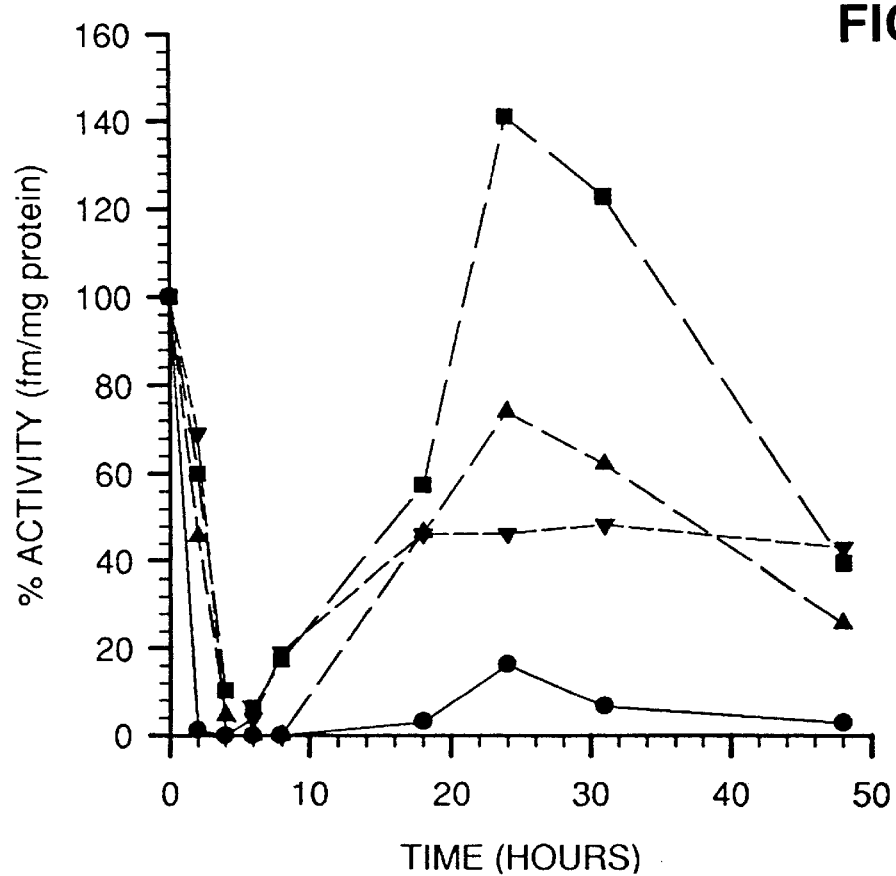

FIG. 20 show that despite the considerably higher initial level of ATase activity in the human breast tumour, B.4280 depletes ATase therein more completely and for a longer period of time than in murine host tissues. In this study using 30 mg/kg B.4280 i.p. extensive depletion was seen in brain tissue, indicating the ability to cross the blood-brain barrier.

Figure 21:
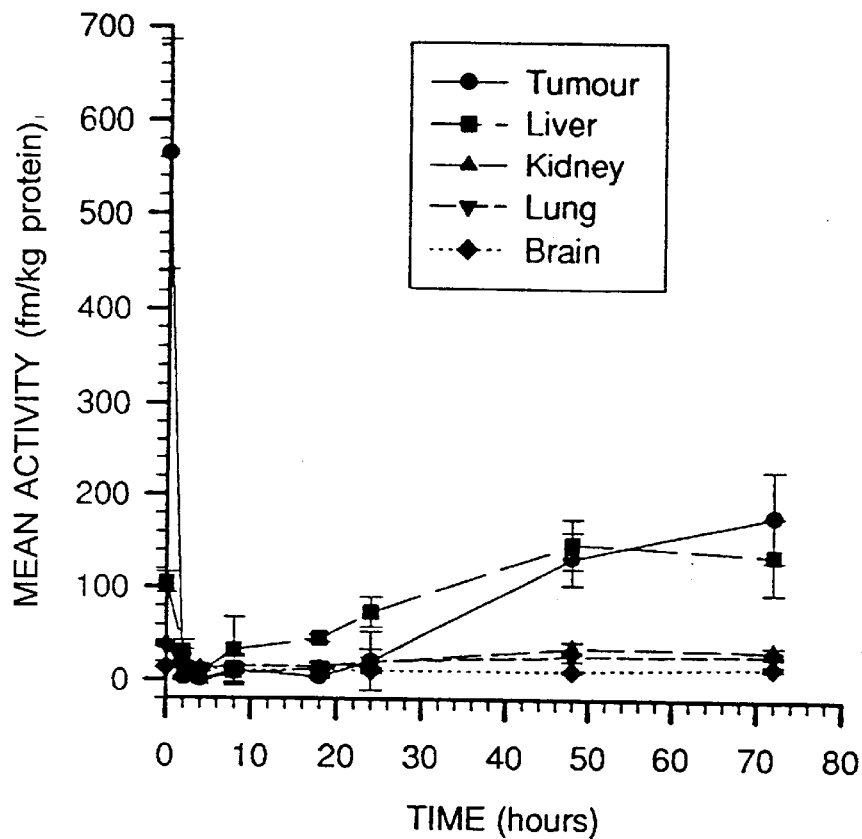
Figure 21:
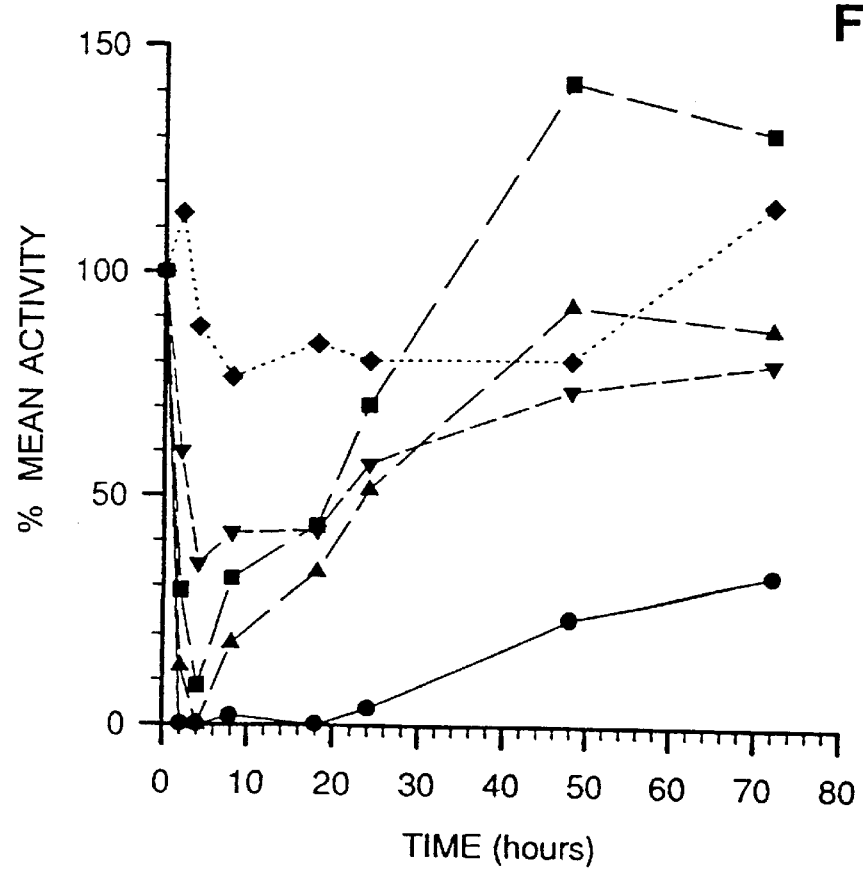

FIG. 21 likewise shows that despite the considerably higher initial level of ATase activity in the human prostate tumour, B.4280 depletes ATase therein more completely and for a longer period of time than in murine host tissues. In this study using 20 mg/kg B.4280 i.p. relatively little depletion was seen in brain tissue, indicating by reference to FIG. 20 that the ability of B.4280 to cross the blood-brain barrier may be dose-dependent.

Figure 22:
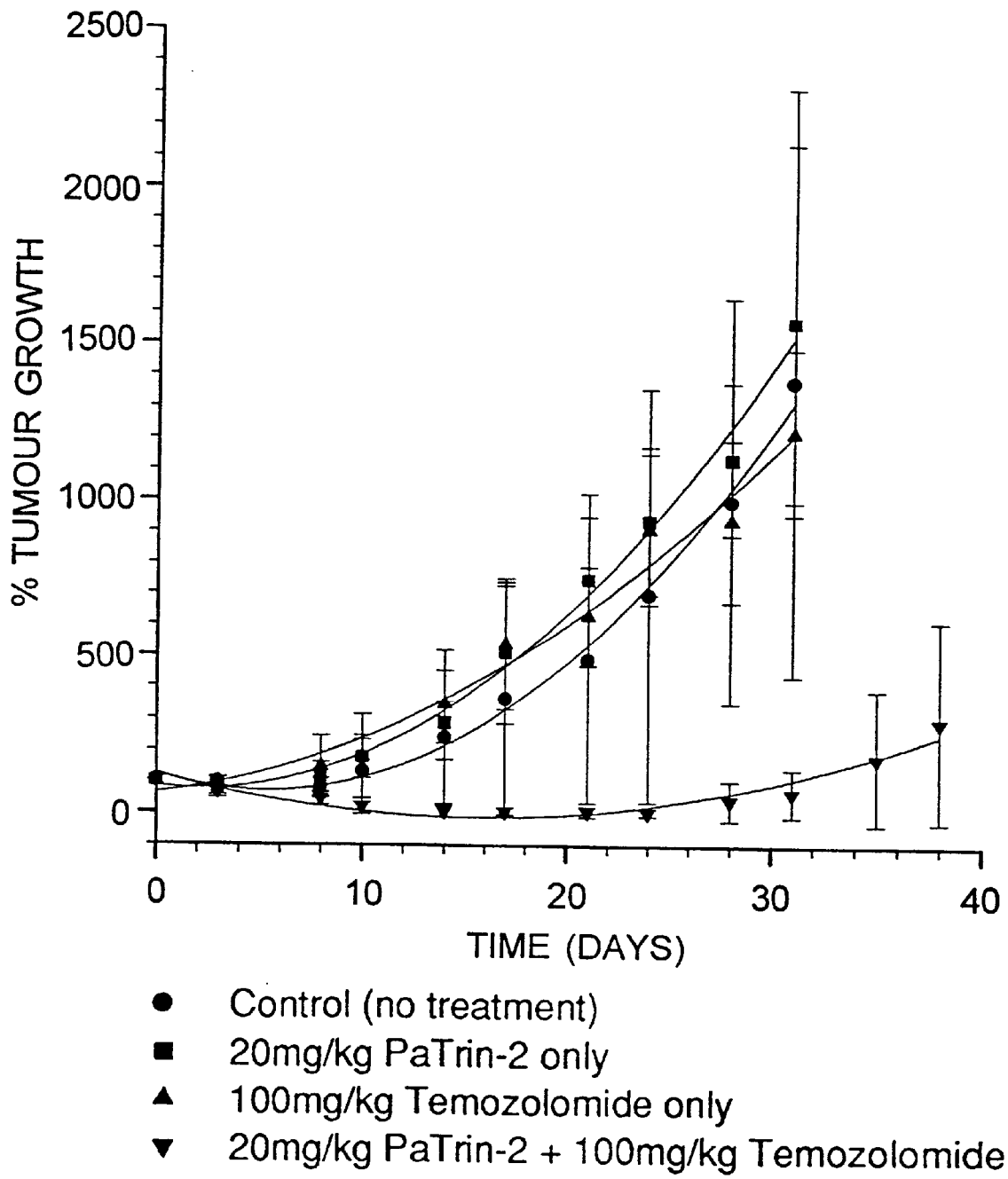
FIG. 22 is a graph of % tumour growth against time (days) showing the effect of B.4280 on the sensitivity of MCF-7 tumours to growth inhibition by temozolomide. Animals were untreated, were given temozolomide alone (100 mg/kg, i.p.) or B.4280 (PaTrin-2) (20 mg/kg i.p.) alone, or B.4280 (20 mg/kg i.p.) followed 1 hour later by temozolomide (100 mg/kg i.p.) on five consecutive days.

FIG. 22 shows that B.4280 (20 mg/kg i.p.) considerably increased the sensitivity of the human breast tumour xenograft to the growth inhibitory effects of temozolomide using a 5 day dosing schedule. This sensitization occurred despite the very high level of ATase in this tumour.

Figure 23:
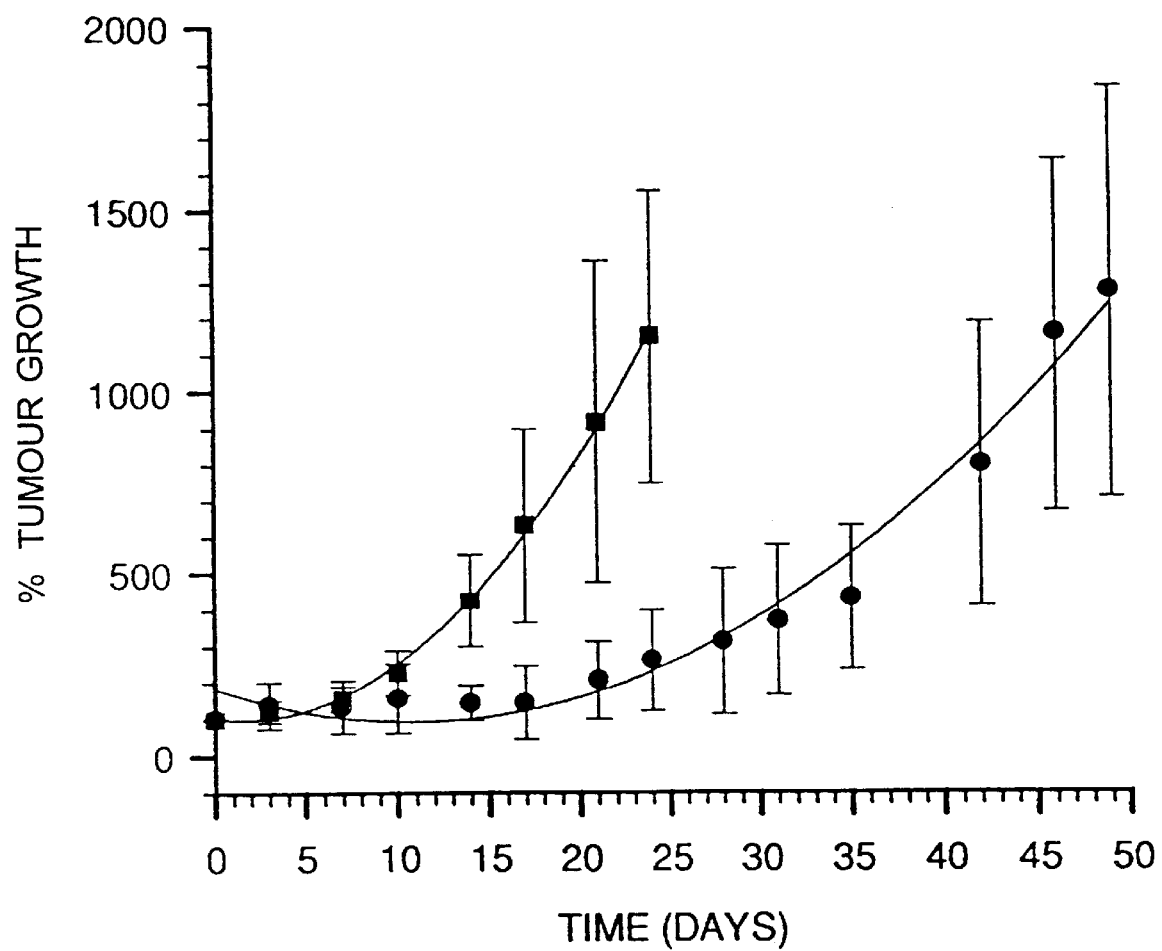
FIG. 23 consists of graphs of % tumor growth, number of surviving mice and mean weight (g) against time (days) showing the effect of a single dose of B.4280 (PaTrin-2) on the sensitivity of melanoma tumours to growth inhibition by a single dose of fotemustine. Animals were given fotemustine (20 mg/kg i.p.) alone, or B.4280 (30 mg/kg p.o) followed 1 hour later by fotemustine (20 mg/kg i.p.).
Figure 23B:
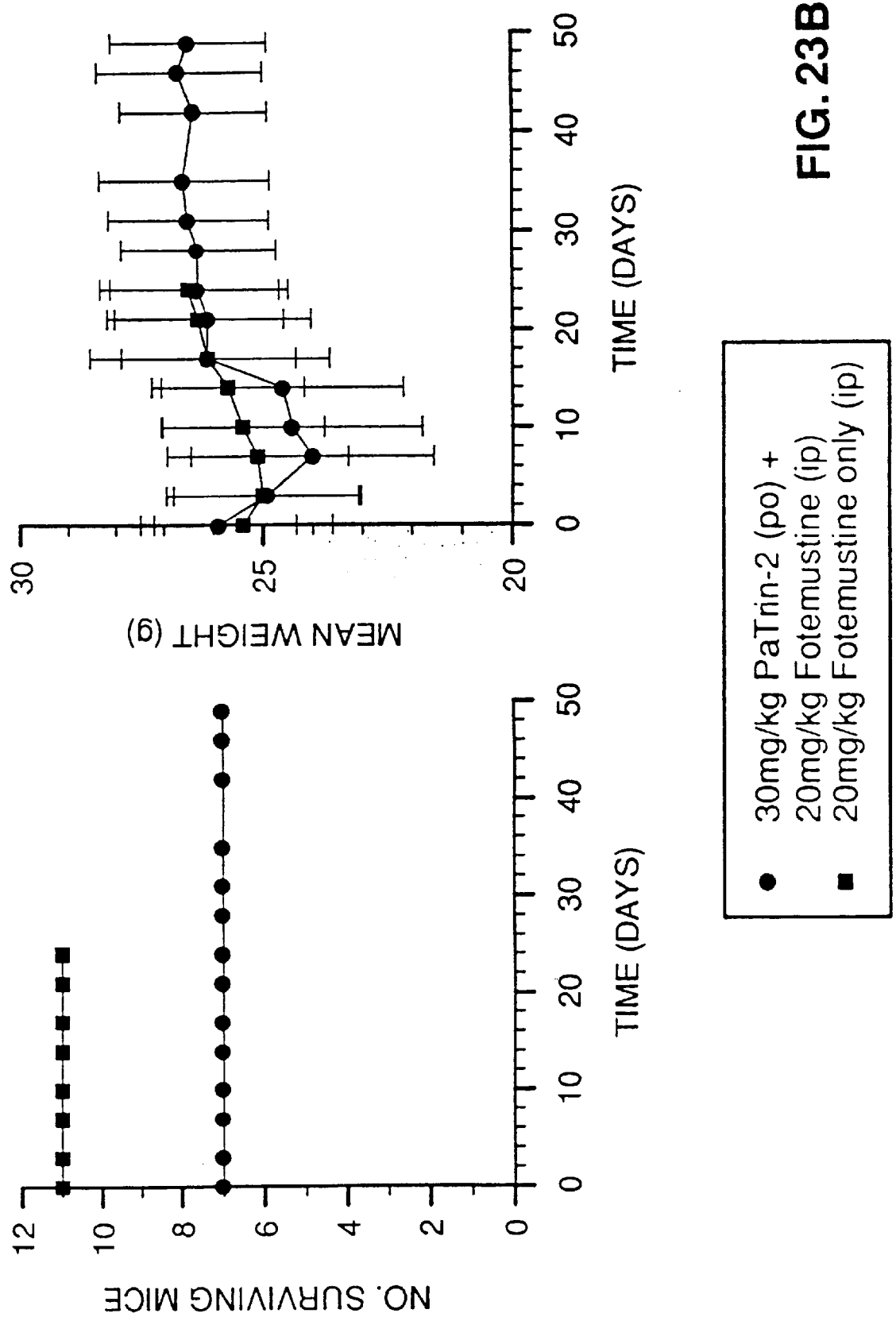
Figure 25:
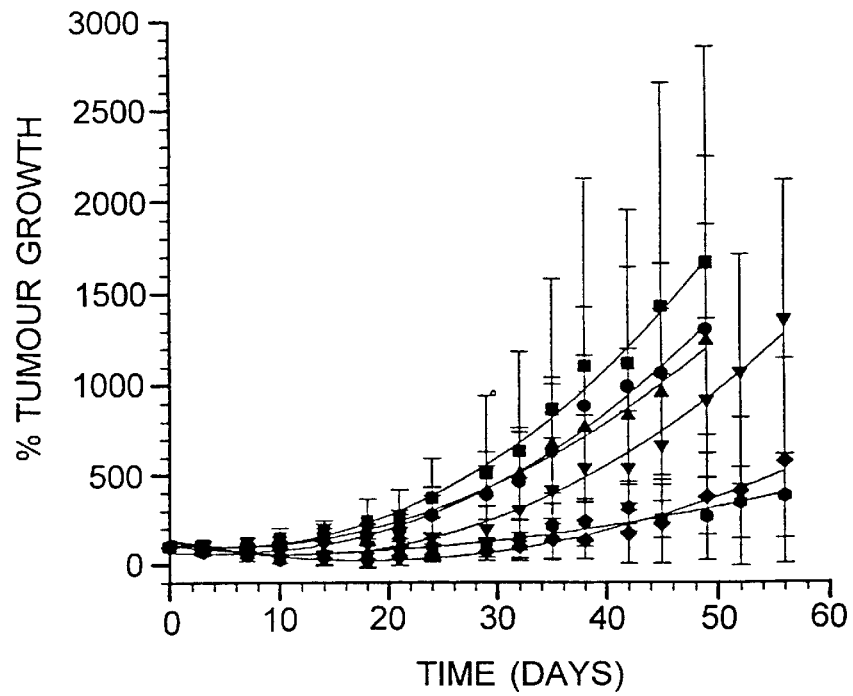
FIG. 25 consists of graphs of % tumour growth, number of surviving mice and mean weight (g) against time showing sensitization of A375M tumours to temozolomide (100 mg/kg i.p.) following administration of 20 mg/kg B.4349 or B.4351 (i.p.).
Figure 25:
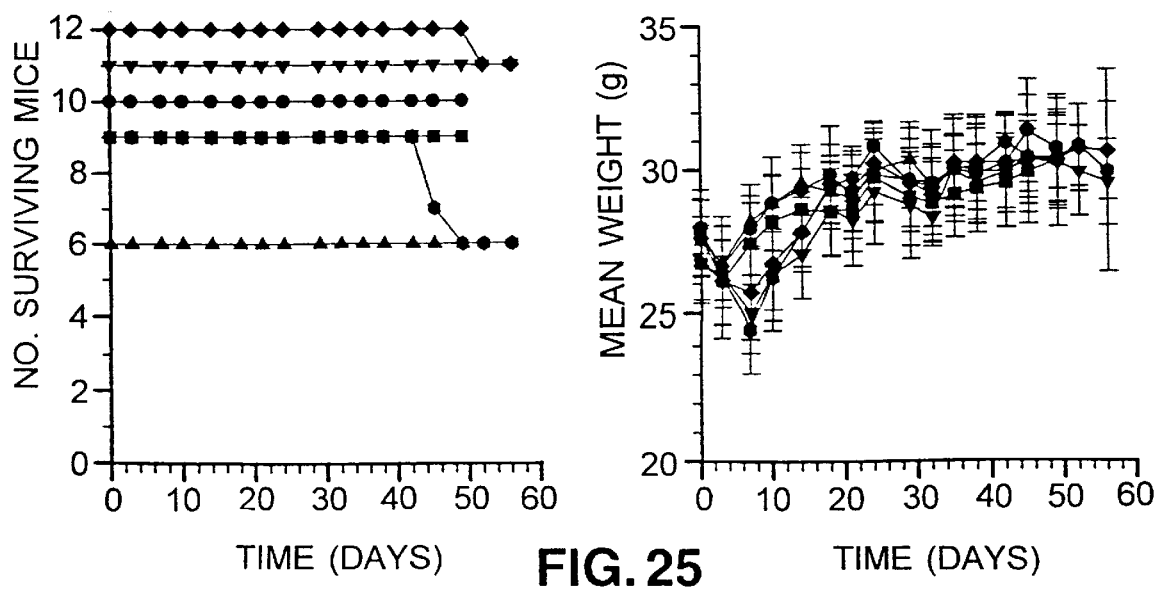
Figure 26:
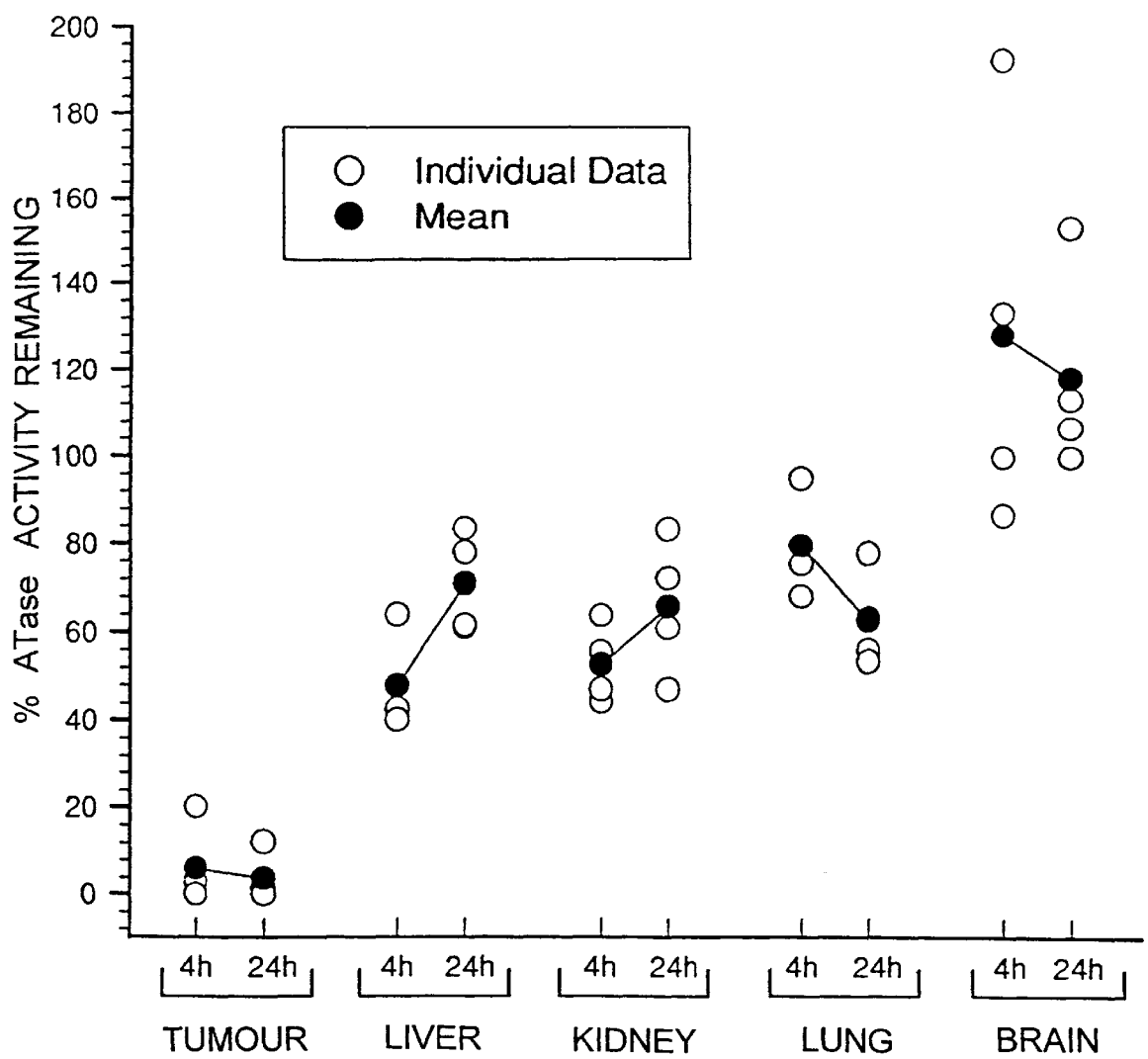
FIG. 26 is a figure showing ATase activities in A375M tumours and murine host tissues at 2 hours and 24 hours following i.p. administration of 90 mg/kg B.4335.

FIG. 23 shows that a single dose of B.4280 (30 mg/kg p.o.) considerably increased the sensitivity of the human melanoma tumour xenograft to the growth inhibitory effects of a single dose of the chloroethylating agent, fotemustine, without any substantial effect on toxicity.

Synthesis of $O^6$-(Methylene[$^3$H])-(4-Bromothenyl)Guanine

Bromothenylaldehyde (0.79 mg, 66.8 umoles was reacted with $NaB[^3H]_4$ (0.0167 mmoles, 60 Ci/mmole) in isopropanol (350 µl) for 1 h at room temperature. The resulting [$^3$H]-4-bromothenylalcohol was extracted into pentane, dried, weighed and reacted with NaH (5.44 mg), and the quaternary ammonium salt of guanine (15.55 mg) in DMSO (250 µl) for 1 hour at room temperature. The product was recovered by precipitation from acetic acid-ether (15 µl glacial acetic in 1.5 ml ether), washed with ether, dried and triturated with $H_2O$. After washing with water, the final product was dried to constant weight. FIG. 28 shows the scheme for synthesis of the radio-labelled B.4280.

High Performance Liquid Chromatography Analysis

An aliquot of the product was dissolved in buffer A (10mM $KH_2PO_4$ containing 7.5% acetonitrile) and subjected to high performance liquid chromatography on an ODS-5 column. Elution at 1 ml/min was with a linear gradient over 20 minutes from 100% A to 20% A:80% B (10mM $KH_2PO_4$ containing 80% acetonitrile). The effluent was monitored for UV absorption at 254 nm and fractions (1 min) were collected and assayed for radioactivity after addiition of 10 ml of Ecoscint A. It was shown that 96% of the radio activity co-chromatographed with authentic B.4280 (FIG. 29).

Incubation of an aliquot of the product with known amounts of pure recombinant human ATase resulted in the transfer of radioactivity to the protein (FIG. 30), strongly suggesting that the mechanism of ATase inactivation involves the transfer of the thenyl group to the active site cysteine residue in the ATase molecule. Measurement of the amount of radioactivity transferred to protein indicated that the $\underline{O}^6$-($[^3H]$-4-bromothenyl)guanine had a radiochemical purity of >96% and a specific activity of 16 Ci/mmole.

$\underline{O}^6$-($[^3H]$-4-bromothenyl)guanine can be used as an alternative to the standard method, which presently uses $[^3H]$-labelled substrate DNA, to determine the amounts of ATase, for example, in cell or tissue extracts. It may also be used to locate active ATase molecules in tumour and other tissue sections by incubation with such sections on microscope slides followed by washing, autoradiography and histological staining. It may also be used to monitor the formation of the $[^3H]$-labelled products of breakdown or metabolism of the agent after administration to mammals. It may also be used to determine the distribution of the B.4280 or its breakdown products in animal tissues and tumours by means of whole body autoradiography.

Typical Synthetic Procedures

Type 1A.

$O^6$-(4-Bromothenyl)hypoxanthine, B.4292

4-Bromothenyl alcohol (1.16 g, 6 mmol) was added to sodium hydride (60% in oil; 0.16 g, 2 mmol) and DMSO (1 ml). The solution was stirred for 30 min. The trimethylammonium salt (0.427 g, 2 mmol) was then added and stirring continued for 2.5 h at 20° C. The solution was cooled in an ice bath and poured into ether (60 ml) containing acetic acid (0.32 ml). A white precipitate was collected, triturated with water (4 ml) and collected again to give B.4292 (436 mg, 69%) recrystallised from methanol.

Type 1B.

$O^6$-Thenyl-2-Methylhypoxanthine, B.4350

DABCO Salt from 6-Chloro-2 -Methylpurine:

6-chloro-2 -methylpurine (0.5 g, 3 mmol) was dissolved in a mixture of DMF (5 ml) and diglyme (25 ml). DABCO (0.66 g, 6 mmol) was then added. The mixture was stirred for 1 h and the precipitate collected to give the quaternary salt (700 mg, 82%). NMR (300 MHz, DMSO-$d_6$): shift in ppm 2.65 (s), 3.27 (t, J=7.5 Hz), 3.78 (s), 4.14 (t, J=7.5 Hz), 8.21 (s).

Thenyl alcohol (684 mg, 6 mmol) was added to sodium hybride (60% in oil; 80 mg, 2 mmol) and DMSO (0.5 ml). The solution was stirred for 30 min. The DABCO salt was then added and stirring continued for 5 h. The solution was then poured into ether (30 ml) containing acetic acid (0.15 ml). A precipitate was collected, triturated with water (4 ml) and collected again to give $O^6$-Thenyl-2-methylhypoxanthine (96 mg, 35%) recrystallised from acetonitrile.

Type 1C.

$O^6$-(4-Bromothenyl)-2-Fluorohypoxanthine, B.4353

To 3.6 ml of 40% fluoroboric acid precooled to −25° C. in a bath was added $O^6$-(4-bromothenyl) guanine (326 mg, 1 mmol) with vigorous stirring. A solution of sodium nitrite (0.116 g, 1.7 mmol) in water (0.15 ml) was added dropwise over a period of 10 min. After 20 min, the solution was poured into ice. The mixture was then allowed to stand at 0° C. for 15 h, then collected and dried to afford almost pure (t.l.c.) B.4353 (180 mg, 55%). Flash chromatography (Hexane-Ethyl Acetate decreasing polarity little by little) afforded B.4353.

Typical Synthetic Procedures (Continued)

Type 3D $O^4$-Thenyl-5-Deazapterin, B.4376 a) $N^2$-Pivaloyl-5-deazapterin

A mixture of 5-deazapterin[33,34] (2.0 g, 13.36 mmol), 4-dimethylaminopyridine (0.22 g, 1.8 mmol) and pivalic anhydride (12 ml) was heated to 165° C. Excess pivalic anhydride was distilled off and the residue dissolved in dichloromethane and applied to a pad of silica gel, and eluted with 2% methanol in dichloromethane. Evaporation and recrystallisation of the product from ethanol gave shiny cream coloured crystals (2.25 g, 74%) of the pivaloyl derivative, m.p. 258–259° C.; $\lambda_{max}$(MeOH) 277 nm; NMR (300 MHz, DMSO-$d_6$)δ1.28(s), 7.44(q), 8.43(dd), 8.88(dd), 11.4(s), 12.31(s).

b) $N^2$-pivaloyl-$O^4$-thenyl-5-deazapterin:

A suspension of $N^2$-pivaloyl-5-deazapterin (0.492 g, 2 mmol) in tetrahydrofuran (8 ml) was stirred for 10 min, and tri-n-butylphosphine (0.606 g, 3 mmol), thenyl alcohol (0.432 g, 3 mmol) and diisopropylazodicarboxylate (0.606 g, 3 mmol) were added successively. The reaction was allowed to proceed for 2 h at room temperature and evaporation than gave an oil. Hexane was added to induce crystallisation. Filtration and recrystallisation from hexane gave bright yellow crystals of the thenyl derivative (0.32 g, 47%) m.p. 107–108° C.; $\lambda_{max}$(MeOH) 272, 311 nm; NMR (300 MHz, DMSO-$d_6$)δ1.28(s), 5.86(s), 6.98(q), 7.28(dd), 7.43(dd), 7.52(q), 8.46(dd), 8.89(dd).

c) B.4376

$N^2$-pivaloyl-$O^4$-thenyl-5-deazapterin (0.28 g, 0.82 mmol) was heated for 24 h under reflux with aqueous NaOH (3M, 2 ml) and ethanol (1 ml). The solvent was removed by evaporation and the residual solid dissolved in water. Acidification with acetic acid gave a white precipitate. Filtration and recrystallisation of the solid from ethanol gave white crystals of $O^4$-thenyl-5-deazapterin (B.4376), (0.107 g, 51%).

Type 4D $O^6$-(4-Bromothenyl)-5-Nitrocytosine, B.4380

Sodium hydride (60% in oil; 80 mg, 2 mmol) was added to a stirred solution of 4-bromothenyl alcohol (290 mg, 1.5 mmol) in dry DMSO (1 ml). After 30 min, 4-amino-2-chloro-5-nitropyrimidine[35] (174 mg, 1 mmol) was added and the mixture heated at 50° C. for 2 h. The DMSO was removed in vacuo and the pH adjusted to 7 with aqueous acetic acid. After extraction into ethyl acetate, the product B.4380 was crystallised from methanol (51 mg, 15%).

Type 5

$S^6$-(4-Bromothenyl)-6-Thioguanine, B.4352

Sodium hydride (60% in oil; 44 mg, 1.1 mmol) was added to a stirred solution of 4-bromothenyl mercaptan (418 mg, 2 mmol) in dry DMSO (0.5 ml). After 30 min, 2-amino-N,N, N-trimethyl-1H-purin-6-aminium chloride (228 mg, 1 mmol) was added and stirring continued for 1 h. Acetic acid (0.12 ml) and ether (30 ml) were added and after decantation and trituration with fresh ether, B.4352 (38 mg, 11%) was filtered off.

9-Substituted $O^6$-(4-Bromothenyl)Guanines:

$O^6$-(4-Bromothenyl)-9-(Ethoxymethyl)Guanine, B.4369

$O^6$-(4-Bromothenyl)guanine (652 mg, 2 mmol) was dissolved in sodium ethoxide (1M, 2 ml, 2 mmol). After 10 min, the ethanol was removed and the residue was dissolved in dry DMF. Chloromethyl ethyl ether (189 mg, 2 mmol) was added dropwise to the stirred solution under an atmosphere of argon. After 45 min, the solvent was removed. The oily product was crystallised from ethanol giving B.4369 (158 mg) as needles. A further 118 mg was obtained by flash chromatography of the mother liquor on silica gel with 5% ethanol in $CH_2Cl_2$. Total yield, 39%.

$O^6$-(4-Bromothenyl)-9-(2-Hydroxyethoxymethyl)Guanine, B.4335

A stirred mixture of $O^6$-(4-bromothenyl)guanine (294 mg, 1 mmol), $(NH_4)_2SO_4$ (47 mg) and hexamethyldisilazane (5 ml) was heated at reflux for 3 h. Volatile material was then evaporated under vacuum. The residue was stirred with benzene (15 ml) and $Hg(CN)_2$ (344 mg, 1.3 mmol) under reflux for 30 min. A solution of (2-acetoxyethoxy)methyl bromide {Ref 4 p33} (197 mg, 1 mmol) in benzene (10 ml) was added, reflux maintained for 2 h, and the cloudy diluted with chloroform (150 ml). The organic phase was washed with saturated aqueous $NaHCO_3$ (30 ml), followed by KI (1M; 30 ml), dried over $MgSO_4$ and evaporated to give an oil (313 mg). This oil was chromatographed on a silica gel column with $CHCl_3$—MeOH (12:1) as eluant, yielding almost pure (t.l.c.) O-acetate (141 mg) of B.4335.

Methanol (60 ml) was saturated with dry ammonia and poured onto this O-acetate in a flask which was tightly stoppered. After dissolution, stirring was stopped and the flask left closed overnight. Evaporation of methanol gave B.4335 (135 mg, 46%), recrystallised from isopropanol.

$O^6$-4-Bromothenyl-9-(β-D-Ribofuranosyl)Guanine, B.4363

A mixture of 2',3',5'-tri-(O-acetyl)guanosine[36] (409 mg, 1 mmol), tri-n-butylphosphine (303 mg, 1.5 mmol) and 4-bromothenyl alcohol (290 mg, 1.5 mmol) in dry tetrahydrofuran (16 ml) was stirred at room temperature for 45 min. Then diisopropyl azodicarboxylate (303 mg, 1.5 mmol) was added dropwise and the mixture stirred for 2 h. The solution was evaporated leaving an oil which was dissolved in THF/MeOH/25% aqueous ammonia (1:1:1; 5 ml) and kept for 48 h at 4° C.

Adsorption on silica gel and column chromatography with $CHCl_3$/MeOH (15:1 to 10:1) gave the riboside B.4363 (205 mg, 44%).

$O^6$-4-Bromothenyl-9-(β-D-2'-Deoxyribofuranosyl) Guanine, B.4379.

A mixture of 3',5'-di-(O-acetyl)-2'-deoxyguanosine[37] (554 mg, 1.5 mmol), tri-n-butylphosphine (666.6 mg, 3.3 mmol) and 4-bromothenyl alcohol (638 mg, 3.3 mmol) in dry tetrahydrofuran (40 ml) was stirred at 80° C. for 15 min. Then diisopropyl azodicarboxylate (666.6 mg, 3.3 mmol) was added dropwise and 15 min later, the reaction mixture was cooled and evaporated leaving an oil. This was dissolved in THF/MeOH/25% aqueous ammonia (1:1:1; 5 ml) and kept for 48 h at 4° C. Adsorption on silica gel and column chromatography with $CHCl_3$/MeOH (20:1) gave the 2'-deoxyriboside B.4379 (338 mg, 51%).

9-(β-D-Arabinofuranosyl)-$O^6$-(4-Bromothenyl)Guanine, B.4368.

An alkoxide solution was made from sodium hydride (60% in oil; 60 mg, 1.5 mmol) and 4-bromothenyl alcohol (344 mg, 1.8 mmol) in dry DMSO (0.5 ml) over 1 h. It was reacted with 2-amino-9-(β-D-arabinofuranosyl)-6-chloropurine[38] (151 mg, 0.5 mmol) and stirred for 5 min at room temperature, then 15 min at 60–65° C. Cooling and trituration with ether (50 ml) and filtration yielded a solid which was dissolved in water (5 ml), neutralised with acetic acid and treated with silica gel. Column chromatography with ethyl acetate/MeOH (19:1) gave the arabinoside B.4368 (87 mg, 38%), pure on t.l.c.

$O^6$-Substituted Guanines

These were made by the standard procedure from the quaternary salt 2-amino-N,N,N-trimethyl-1H-purin-6-aminium chloride and the appropriate alkoxide derived from the alcohol and sodium hybride in DMSO (cf.pp.16d, 17, 18, 47 of Jul. 12, 1995).

TABLE 1A

| Compound, Test No. | | $O^6$-Substituent RCH$_3$ | Yield % | Solvent for Recrystn. | M.p. (decomp.) (° C.) | Formula | Molecular Weight | | Analysis C | H | N |
|---|---|---|---|---|---|---|---|---|---|---|---|
| Type 1A. | Hypoxanthines | | | | | | | | | | |
| | B. 4293 | furfuryl | 60 | MeOH | 154 | $C_{18}H_8N_4O_2$ | 216 | | | | |
| | B. 4291 | thenyl | 66 | MeOH | 168 | $C_{10}H_8N_4OS$ | 232 | Found | 51.85 | 3.40 | 24.12 |
| | | | | | | | | Req. | 51.71 | 3.47 | 24.12 |
| | B. 4292 | 4-bromothenyl | 69 | MeOH | 170 | $C_{10}H_8BrN_4OS$ | 311 | Found | 38.33 | 2.18 | 17.66 |
| | | | | | | | | Req | 38.6 | 2.26 | 18.00 |
| 1B. | 2-Methylhypoxanthines | | | | | | | | | | |
| | B. 4347 | benzyl | 43 | MeCN | 191–193[a] | $C_{12}H_{11}N_4O$ | 240 | Found | 65.05 | 4.91 | 23.30 |
| | | | | | | | | Req | 64.99 | 5.03 | 23.32 |
| | B. 4350 | thenyl | 35 | MeCN | 176–178[a] | $C_{12}H_{11}N_4OS$ | 325 | Found | 53.63 | 3.90 | 22.67 |
| | | | | | | | | Req | 53.64 | 4.09 | 22.75 |
| 1C. | 2-Fluorohypoxanthines | | | | | | | | | | |
| | B. 4353 | 4-bromothenyl | 55 | Column | 142 | $C_{10}H_4BrFN_4OS$ | 329 | | | | |
| 1D. | 9-(2-Hydroxyethoxy-methylguanines | | | | | | | | | | |
| | B. 4334 | benzyl | 46 | i-PrOH | 150–152[a] | $C_{15}H_{12}N_5O_4$ | 315 | Found | 57.19 | 5.59 | 21.93 |
| | | | | | | | | Req | 57.13 | 5.43 | 22.21 |
| | B. 4335 | 4-bromothenyl | 42 | i-PrOH | 156–158[a] | $C_{13}H_{14}BrN_3O_2S$ | 400 | Found | 39.16 | 3.68 | 17.20 |
| | | | | | | | | Req | 39.01 | 3.53 | 17.53 |
| 1E. | 8-Hydroxyguanines | | | | | | | | | | |
| | B. 4349 | 4-bromothenyl | 56 | Aq. EtOH | >230 | $C_{10}H_8BrN_5O_2S$·½$H_2O$ | 351 | Found | 34.53 | 2.48 | 19.50 |
| | | | | | | | | Req. | 34.20 | 2.58 | 19.94 |
| Type 2A. | 8-Azaguanines | | | | | | | | | | |
| | B. 4270 | 4-fluorobenzyl | 40 | Aq. MeOH | >280 | $C_{10}H_9FN_4O$ | 260 | Found | 51.50 | 3.85 | 29.44 |

TABLE 1A-continued

| | | | | | | | | Req. | 50.77 | 3.49 | 32.30 |
|---|---|---|---|---|---|---|---|---|---|---|---|
| | B. 4314 | 4-chlorothenyl | 26 | Aq. MeOH | >200 | $C_2H_5ClN_4OS$ | 282.7 | Found | 28.86 | 2.61 | 28.61 |
| | | | | | | | | | 38.24 | 2.50 | 29.73 |
| | B. 4289 | 4-bromothenyl | 12 | MeCN | >190 | $C_8H_5BrN_6OS$ | 327 | Found | 35.91 | 2.78 | 24.60 |
| | | | | | | | | Req. | 33.04 | 2.16 | 25.69 |
| 2B. | 8-Aza-7-deazaguanines | | | | | | | | | | |
| | B. 4310 | benzyl | | MeOH | 160 | $C_{18}H_{11}N_5O_1H_2O$ | 259 | Found | 55.53 | 4.9 | 26.41 |
| | | | | | | | | Req. | 55.59 | 5.01 | 27.02 |
| | B. 4340 | 4-fluorobenzyl | 65 | EtOH | 188 | $C_{12}H_{12}FN_5O \cdot \frac{1}{4}H_2O$ | 263.7 | Found | 53.82 | 3.76 | 25.97 |
| | | | | | | | | Req. | 54.6 | 4.0 | 26.55 |
| | B. 4339 | 4-chlorobenzyl | 92 | EtOH | 242–244* | $C_{12}H_{10}ClN_5O \cdot \frac{1}{4}H_2O \frac{1}{4}EtOH$ | 296 | Found | 51.15 | 3.89 | 23.43 |
| | | | | | | | | Req. | 50.7 | 4.25 | 23.64 |
| | B. 4343 | piperonyl | 50 | EtOH | 186 | | | | | | |
| | B. 4348 | furfuryl | | EtOH | 150[c] | $C_{13}H_{11}N_5C_3$ | 28.5 | Found | 54.52 | 3.82 | 24.50 |
| | | | | | | | | Req. | 54.7 | 3.88 | 24.55 |
| | B. 4338 | thenyl | 68 | EtOH | 180 | $C_{10}H_6N_5O_2 \cdot \frac{1}{4}H_2O$ | 236.7 | Found | 50.96 | 3.87 | 29.54 |
| | | | | | | | | Req. | 50.96 | 4.06 | 29.71 |
| | B. 4337 | 4-bromothenyl | 79 | EtOH | 180 | $C_{10}H_6N_5OS$ | 247 | Found | 47.58 | 3.54 | 27.41 |
| | | | | | | | | Req. | 47.7 | 3.8 | 27.8 |
| | | | | | | $C_{10}H_2BrNiOS$ | 326 | Found | 37.08 | 2.52 | 21.31 |
| | | | | | | | | Req. | 36.8 | 2.5 | 21.5 |
| Type 3A. | 8-Ozaguanines | | | | | | | | | | |
| | B. 4272 | 4-fluorobenzyl | 41 | Acetone | 223–224 | $C_{11}H_5N_5O_2$ | 261 | Found | 50.39 | 3.08 | 26.65 |
| | | | | | | | | Req. | 50.58 | 3.09 | 26.81 |
| | B. 4285 | 4-chlorobenzyl | 63 | Acetone | 219–220 | $C_{11}H_8ClN_5O_2$ | 277.7 | Found | 47.59 | 2.88 | 25.25 |
| | | | | | | | | Req. | 47.58 | 2.90 | 25.22 |
| | B. 4299 | 4-chlorothenyl | 55 | Acetone | 164–165 | $C_{12}H_4ClN_5O_2S$ | 283.7 | Found | 37.68 | 2.15 | 24.43 |
| | | | | | | | | Req. | 38.10 | 2.13 | 24.69 |
| | B. 4287 | 4-bromothenyl | 61 | Acetone | 170–172 | $C_2H_6BrN_5O_2S$ | 328 | Found | 33.30 | 1.85 | 21.37 |
| | | | | | | | | Req. | 32.94 | 1.84 | 21.34 |
| 3B. | 8-Thioguanines | | | | | | | | | | |
| | B. 4296 | benzyl | 39 | EtOH | | $C_{11}H_8N_5OS$ | 259 | | | | |
| | B. 4286 | 4-fluorobenzyl | 11 | PLC | 182–184 | $C_{11}H_5FN_2OS$ | 277 | | | | |
| | B. 4315 | 4-chlorobenzyl | 13 | MeOH | | $C_5H_6ClN_5OS_2$ | 299.8 | Found | 36.27 | 2.04 | 23.07 |
| | | | | | | | | Req. | 36.06 | 2.02 | 23.36 |
| | B. 4351 | 4-bromothenyl | 41 | MeOH | 156–160 | $C_9H_6BrN_5OS_2$ | 144 | Found | 31.49 | 1.60 | 20.11 |
| | | | | | | | | Req. | 31.41 | 1.76 | 20.35 |
| 3C. | Pterins ($O^2$-substituent) | | | | | | | | | | |
| | B. 4290 | 4-fluorobenzyl | 55 | MeOH | >110 | $C_{13}H_{12}FN_5O$ | 271 | Found | 57.87 | 3.88 | 25.65 |
| | | | | | | | | Req. | 57.56 | 3.72 | 25.82 |
| | B. 4316 | 4-chlorobenzyl | 41 | MeOH | >170 | $C_{13}H_8ClN_5OS$ | 293.7 | Found | 44.93 | 2.84 | 23.72 |
| | | | | | | | | Req. | 44.98 | 2.75 | 23.84 |
| | B. 4288 | 4-bromothenyl | 63 | MeOH | 178–179 | $C_{11}H_8BrN_5OS$ | 338 | Found | 39.34 | 3.13 | 20.25 |
| | | | | | | | | Req. | 39.07 | 2.38 | 20.71 |
| Type 4A. | 2,4-diamino-6-hydroxypyrimidines | | | | | | | | | | |
| | B. 4305 | 4-fluorobenzyl | 98 | $C_6H_5$/Petrol | 133–134 | $C_{11}H_{10}FN_5O$ | 234 | Found | 56.20 | 4.79 | 23.66 |
| | | | | | | | | | 56.40 | 4.73 | 23.92 |
| | B. 4304 | 4-chlorobenzyl | 31 | $C_6H_5$ | 122–123 | $C_{12}H_{11}ClN_4O$ | 250.7 | Found | 52.43 | 4.56 | 22.47 |
| | | | | | | | | Req. | 52.70 | 4.42 | 22.35 |
| | B. 4303 | piperonyl | 79 | MeCN | 168–171 | $C_{17}H_{12}N_6O_5$ | 260 | Found | 55.31 | 4.64 | 21.38 |
| | | | | | | | | Req. | 55.38 | 4.65 | 21.52 |
| | B. 4307 | thenyl | 97 | MePh | 100 | $C_9H_{10}N_4OS$ | 222 | Found | 48.83 | 4.58 | 25.25 |
| | | | | | | | | Req. | 48.63 | 4.54 | 25.21 |
| | B. 4302 | 4-chlorothenyl | 45 | MePh | 129–130 | $C_9H_9ClN_4OS$ | 256.7 | Found | 42.40 | 3.68 | 22.00 |
| | | | | | | | | Req. | 42.11 | 3.53 | 21.83 |
| 4B. | 2,4-Diamino-6-hydroxy-5-autrosopyrimidines | | | | | | | | | | |
| | B. 4301 | 4-fluorobenzyl | 76 | MeOH | >250 | $CH_{10}FN_5O_2$ | 263 | Found | 49.60 | 3.90 | 26.29 |
| | | | | | | | | Req. | 50.19 | 3.83 | 26.61 |
| | B. 4311 | 4-chlorobenzyl | 84 | Acetone | >190 | $C_9H_8ClN_5O_2S$ | 285.7 | Found | 37.54 | 2.79 | 24.22 |
| | | | | | | | | Req. | 37.84 | 2.82 | 24.51 |
| | B. 4312 | 4-bromothenyl | 62 | Acetone | 200–201 | $C_9H_8BrN_5O_2S$ | 330 | Found | 32.87 | 2.38 | 20.96 |
| | | | | | | | | Req. | 32.74 | 2.44 | 21.21 |
| 4C. | 2,4-Diamino-6-hydroxy-5-nitropyrtnidines | | | | | | | | | | |
| | B. 4308 | piperonyl | 67 | DMF | >175 | $C_{12}H_{11}N_5O_5$ | 305 | Found | 47.44 | 4.07 | 22.83 |
| | | | | | | | | Req. | 47.22 | 3.63 | 22.94 |
| | B. 4306 | thenyl | 34 | MeOH | 159–160 | $C_9H_5N_6O_3S$ | 267 | Found | 40.99 | 3.71 | 25.99 |
| | | | | | | | | Req. | 40.44 | 3.39 | 26.21 |
| Type 3D. | 5-Deazapterins ($O^4$-substituent) | | | | | | | | | | |
| | B. 4276 | thenyl | 51 | EtOH | 215–216 | $C_{12}N_{10}N_4OS$ | 258 | | | | |
| 4D. | 5-Nitrocytosines ($O^2$-substituent) | | | | | | | | | | |
| | B. 4380 | 4-bromothenyl | 15 | MeOH | 143–144 | $C_9H_7BrN_4O_3S$ | 331 | | | | |
| 5. | 6-Thtoguanines ($S^6$-substituent) | | | | | | | | | | |
| | B. 4228 | piperonyl | 69 | $CH_2OH$ | 204–212 | $C_{13}H_{11}N_5O_2S$ | 301 | Found | 50.25 | 3.60 | 23.66 |

TABLE 1A-continued

| | | | | | | | Req. | 51.82 | 3.68 | 23.24 |
|---|---|---|---|---|---|---|---|---|---|---|
| B. 4352 | | 4-bromothenyl | 11 | $CH_2OH$ | 180–184 | $C_{14}H_8BrN_5O_1$ ½$CH_2OH$ | 342 | Found 35.07 35.16 | 2.42 2.66 | 19.49 19.84 |

| | | | | | M.p. | | Molecular | Analysis[a] | | |
|---|---|---|---|---|---|---|---|---|---|---|
| Compound, Test No. | | 9-Substituent | Yield % | Solvent for Recrystn. | (° C.) | Formula | Weight | C | H | N |
| B.4369 | | ethoxymethyl | 39 | EtOH | 134–5 | $C_{13}H_{14}BrN_5O_2S$ | 384 | 40.58 (40.64 | 3.71 3.67 | 17.97 18.23) |
| B. 4370 | | n-octyloxymethyl | 39 | EtOH | 90 | $C_{10}H_{20}BrN_5O_2S$ | 468 | 48.97 (48.72 | 5.67 5.60 | 14.82 14.95) |
| B. 4334[b] | | 2-hydroxy-ethoxymethyl | 46 | i-PrOH | 150–2 | $C_{15}H_{27}N_5O_3$ | 315 | 57.19 (57.13 | 5.59 5.43 | 21.93 22.21) |
| B. 4335 | | 2-hydroxy-ethoxymethyl | 42 | i-PrOH | 156–8 | $C_{13}H_{14}BrN_5O_3S$ | 400 | 39.16 (39.01 | 3.68 3.53 | 17.20 17.50) |
| B. 4363 | | β-D-ribo-furanosyl | 44 | | | $C_{15}H_{16}BrN_5O_5S$ | 458 | | | |
| B. 4368 | | β-D-arabino-furanosyl | 38 | | | $C_{15}H_{16}BrN_5O_5S$ | 458 | | | |
| B. 4379 | | β-D-2-deoxyribo-furanosyl | 51 | | | $C_{15}H_{16}BrN_5O_4S$ | 442 | | | |

[a]Found, with required values in parenthesis.
[b]$O^6$-benzyl

TABLE 1B

| Compound Type, Test No. | | $O^6$-Substituent $RCH_2$ | $\lambda_{max}$ (MeOH) (nm) | $\delta_H$ [ppm from TMS, $(CD_3)_2SO_1$]/(Hz) |
|---|---|---|---|---|
| Type 1A. | Hypoxanthines | | | |
| | B. 4293 | furfuryl | 252 | 5.60(s), 6.53(dd, 3.1, 1.9), 6.69(d, J), 7.76(dd, 19, 3.9) 8.39(s), 8.55(s) |
| | B. 4291 | thenyl | 240 | 5.83(s), 7.08(dd, 5.1, 3.4), 7.35(d, 3.4), 7.6(d, 5.1), 8.39(s), 8.51(s) |
| | B. 4292 | 4-bromothenyl | 251 | 5.80(s), 7.38(d, 13), 7.73(d, 13), 8.42(s), 8.58(s) |
| Type 1B. | 2-Methylhypoxanthines | | | |
| | B. 4347 | benzyl | 256 | 2.61(s), 5.60(s), 7.50(m), 8.32(s) |
| | B. 4350 | thenyl | 240 | 2.63(s), 5.77(s), 7.05(dd, 5.1, 2.6, 7.33(d), 2.4), 7.58(dd, 5.1, 1.0) 8.26(s), 13.22(s) |
| Type 1C. | 2-Phorohypoxanthines | | | |
| | B. 4353 | 4-bromothenyl | 233, 255 | 5.77(s), 7.4(d, 1.5), 7.77(d, 1.5), 8.45(s), 13.64(bs) |
| Type 1D. | 9-(2-Hydroxyethoxymethyl)guanines | | | |
| | B. 4334 | benzyl | 247, 283 | 3.48(m), 4.70(s), 5.45(s), 6.59(s), 7.45(m), 8.03(s), |
| | B. 4335 | 4-bromothenyl | 245, 284 | 3.49(m), 4.71(s), 5.45(s), 5.66(s), 6.65(s), 7.30(d, 1.5) 7.72(d, 1.5) 8.04(s) |
| Type 1E. | 8-Hydroxyguanines | | | |
| | B. 4349 | 4-bromothenyl | 239, 293 | 5.54(s), 6.24(s), 7.33(d, 1.4) 7.70(d, 1.4), 10.49(s) 11.12(s) |
| Type 2A. | δ-Azaguanines | | | |
| | B. 4270 | 4-fluorobenzyl | 288 | 5.57(s), 7.04(s), 7.28(m), 7.65(m), 15.38(s) |
| | B. 4314 | 4-chlorobenzyl | 288 | 5.71(s), 7.13(s), 7.41(d, 1.5), 7.66(d, 1.5), 15.42(s). |
| | B. 4289 | 4-bromobenzyl | 287 | 5.73(s), 7.12(s), 7.43(d, 1.5), 7.76(d, 1.5), 15.39(s). |
| Type 2B. | 8-Aza-7-diazaguanines | | | |
| | B. 4310 | benzyl | 217 | 5.50(s), 6.68(s), 7.74(m), 7.82(s), 12.87(bs) |
| | B. 4340 | 4-fluorobenzyl | 278 | 5.49 (s), 6.70(s), 7.20(m), 7.61(m), 7.83(s), 12.88(bs) |
| | B. 4339 | 4-chlorobenzyl | 276 | 5.50(s), 6.69(s), 7.49(d, 8.4), 7.56(d, 8.4), 7.83(s), 12.90(s) |
| | B. 4343 | piperonyl | 282 | 5.39(s), 6.95(s), 6.69(s), 6.94(d, 7.3), 7.04(dd, 7.9, 1.5), 7.1(dd, 1.5), 7.50(s) 12.86(bs). |
| | B. 4348 | furfuryl | 277 | 5.46(s), 6.52(s), 0.70(s), 6.71(s), 7.73(s), 7.79(s), 12.85(bs). |
| | B. 4338 | thenyl | 278 | 5.69(s), 6.73(s), 7.07(d, 3.5), 7.35(s), 7.60(d, 1.1), 7.79(s), 12.90(bs) |
| | B. 4337 | 4-bromothenyl | 278 | 5.65(s), 6.76(s), 7.38(s), 7.72(d, 1.3), 7.91(s), 2.91(bs) |
| Type 3A. | N-Oxaguanines | | | |
| | B. 4272 | 4-chlorobenzyl | 257, 341 | 5.62(s), 7.39(1, 9.1), 7.68(s), 7.91(s), 7.97(s). |
| | B. 4285 | 4-chlorobenzyl | 256, 340 | 5.63(s), 7.53(d, 8.3), 7.65(d, 8.3), 7.90(s), 7.97(s) |
| | B. 4299 | 4-chlorobenzyl | 252, 343 | 5.78(s), 7.46(d, 1.6), 7.72(d, 1.6), 7.95(s), 8.01(s). |
| | B. 4287 | 4-bromobenzyl | 253, 343 | 5.79(s), 7.49(d, 1.6), 7.8(d, 1.6), 7.95(s), 8.01(s) |
| Type 3B. | 8-Thiaguanines | | | |
| | B. 4296 | benzyl | 227, 361 | |
| | B. 4286 | 4-fluorobenzyl | 235, 362 | 5.59(s), 7.29(d, 8.9), 7.51(s), 7.67(m) |
| | B. 4315 | 4-chlorobenzyl | 228, 360 | 5.75(s), 7.44(d, 1.6), 7.55(bs), 7.69(d, 1.6) |
| | B. 4351 | 4-bromothenyl | 228, 361 | 5.78(s), 7.45(d, 1.6), 7.46(bs), 7.75(d, 1.6) |
| Type 3C. | Pterins ($O^6$-substituent) | | | |
| | B. 4290 | 4-fluorobenzyl | 232, 264(sb, 162 | 5.56(s), 7.29(1.6, s), 7.4(bs), 7.66(s), 8.45(d, 1.8), 8.82(d, 1.8) |
| | B. 4316 | 4-chlorothenyl | 232, 364 | 5.71(s), 7.41(d, 1.6), 7.47(bs), 7.67(d, 1.6), 8.40(d, 2.0), 8.83(d, 2.0) |

TABLE 1B-continued

| | Compound Type, Test No. | Substituent RCH₂ | $\lambda_{max}$ (MeOH) (nm) | $\delta_H$ [ppm from TMS, (CD$_3$)$_2$SO$_1$]/(Hz) |
|---|---|---|---|---|
| Type 4A. | B. 4288<br>2,4-diamino-6-hydroxy-pyrimidines | 4-bromothenyl | 231, 364 | 5.73(s, 7.44(d, 1.6), 7.50(bs), 7.77(d, 1.6)8.46(d, 2), 8.83(d, 2) |
| | B. 4305 | 4-fluorobenzyl | 238, 267 | 5.18(s), 5.19(s), 5.96(s), 6.10(s), 7.19(t, 8.8), 7.44(dd, 8.8, 5.8) |
| | B. 4304 | 4-chlorobenzyl | 238, 268 | 5.11(s), 5.22(s), 5.96(s), 6.10(s), 7.44(s) |
| | B. 4303 | piperonyl | 236, 267 | 5.09(s), 5.11(s), 5.97(s), 6.01(s), 6.07(s), 6.91(d, 1.1), 7.00(s). |
| | B. 4307 | thenyl | 235, 267 | 5.08(s), 5.40(s), 6.00(s), 6.10(s), 7.03(dd, 8.1, 3.5) 7.20(dd, 8.1, 1.1), 7.54 (dd, 3.5, 1.1) |
| Type 4B. | B. 4302<br>2,4-Diamino-6-hydroxy-3-nitroxopyrimidines | 4-chlorothenyl | 236, 265 | 5.08(s), 5.35(s), 6.03(s), 6.13(s), 7.19(s), 7.55(d, 1.6). |
| | B. 4301 | 4-fluorobenzyl | 336 | 5.59(s), 7.26(m), 7.65(m), 7.80(bs), 7.85(bs), 8.00(bs), 10.05(bs). |
| | B. 4311 | 4-chlorothenyl | 335 | 5.73(s), 7.40(d, 1.6), 7.66(d, 1.6), 7.94(s), 7.98(d, 2.7), 8.11(d, 4.2), 10.03 (d, 4.2). |
| | B. 4312 | 4-bromothenyl | 335 | 5.75(s), 7.42(d, 1.4), 7.75(d, 1.4), 7.93(s), 7.98(s), 8.12(d, 4.0), 10.04 (d, 4.0) |
| Type 4C. | 2,4-diamino-6-hydroxy-5-nitropyrimidines | | | |
| | B. 4308 | piperonyl | 288, 330 | 5.33(s), 6.05(s), 6.95(d, 8.0), 7.00(dd, 8.0, 1.4), 7.10(d, 1.4); 7.26(bs), 7.3 7.96(bs). |
| | B. 4306 | thenyl | 234, 329 | 5.59(s), 7.03(dd, 5.1, 3.5), 7.28(d, 3.5), 7.32(bs), 7.56(d, 5.1), 7.94(bs) |

| Compound Type, Test No. | Substituent RCH₂ | $\lambda_{max}$ (MeOH) (nm) | $\delta_H$ [ppm from TMS, (CD$_3$)$_2$SO$_1$]/(Hz) |
|---|---|---|---|
| Type 3D 5-Deazapterins (O⁴-substituent) | | | |
| B. 4376 | thenyl | 248, 309 | 5.54(s), 6.96(q), 7.716(dd), 7.38(dd), 7.41(q), 8.39(dd), 8.79(dd). |
| Type 4D 5-Nitrocytosines (O²-substituent) | | | |
| B. 4380 | 4-bromothenyl | 255 sh, 334 | 5.19(s), 7.20(d), 7.56(d), 8.24(s), 8.70(s), 8.90(s). |
| Type 5 6-Thioguanines (S⁶-substituent) | | | |
| B. 4228 | piperonyl | 245, 311 | 4.56(s), 6.06(s), 6.55(s), 7.03(d), 7.06(d), 7.14(s), 8.08(s), 12.67(bs). |
| B. 4352 | 4-bromothenyl | 241, 314 | 4.77(s), 6.52(s), 7.18(d), 7.51(d), 7.93(s), 12.61(bs) |

| Compound Type, Test No. | 9-Substituent | Yield % | $\lambda_{max}$ (MeOH) (nm) | $\delta_H$ [ppm from TMS, (CD$_3$)$_2$SO$_1$]/(Hz) |
|---|---|---|---|---|
| B. 4369 | ethoxymethyl | | 245, 284 | 3.35(s), 5.41(s), 5.66(s), 6.66(s), 7.38(d), 7.73(d), 8.04(s). |
| B. 4370 | n-octyloxymethyl | | 245, 284 | 0.09(t), 1.17(m), 3.36(t), 5.41(s), 5.66(s), 6.66(s), 7.38(d), 7.72(d), 8.03(s). |
| B. 4334[a] | 2-hydroxy-ethoxymethyl | | 245, 283 | 3.48(m), 4.70(s), 5.45(s), 6.59(s), 7.45(s), 8.03(s). |
| B. 4335 | 2-hydroxy-ethoxymethyl | | 245, 284 | 3.49(m), 4.71(s), 5.45(s), 5.66(s), 6.65(s), 7.30(d, 1.5), 7.72(d, 1.5), 8.40(s). |
| B. 4363 | β-D-ribo-furanosyl | | — | 3.54(m), 3.63(m), 3.91(dd), 4.12(dd), 4.48(ddd), 5.12(dd), 5.18(d), 5.45(d), 5.66(s), 5.80(dd), 6.61(s), 7.38(d), 7.71(d), 8.15(s). |
| B. 4368 | β-D-arabino-furanosyl | | 245, 284 | 3.64(m), 3.76(dd), 4.07(m), 5.09(dd), 5.51(d), 5.53(m), 6.13(d), 6.60(d), 7.37(d), 7.71(d), 7.95(s) |
| B. 4379 | β-D-2-deoxyribo-furanosyl | | | 2.39(ddd), 2.72(ddd), 3.65(ddd), 3.98(dd), 4.40(dd), 5.11(s) 5.41(d), 5.80(s), 6.38(dd), 6.67(s), 7.49(d), 7.83(d), 8.25(s). |

[a]O⁶-benzyl

TABLE 2

| INACTIVATOR TYPE | I$_{50}$ ($\mu$M) hAT | T ½ (h) in PBS |
|---|---|---|
| 1A | | |
| B.4291 | | |
| O⁶-(thenyl)-hypoxanthine | 1.9 | >20 |
| B.4293 | | |
| O⁶-(furfuryl)-hypoxanthine | 28 | >16 |
| B.4292 | | |
| O⁶-(4-bromothenyl)-hypoxanthine | 0.3 | >16 |
| O⁶-(benzyl)-hypoxanthine[b] | 85 | |
| 1B | | |
| B.4347 | | |
| O⁶-(benzyl)-2-methylhypoxanthine | 75 | |
| B.4350 | | |
| O⁶-(thenyl)-2-methylhypoxanthine | 14 | |
| 1C | | |
| B.4353 | | |
| O⁶-(4-bromothenyl)-2-fluorohypoxanthine | 1.4 | |
| O⁶-(benzyl)-2-fluorohypoxanthine[a] | 48 | |
| 1D | | |
| B.4334 | | |
| O⁶-(benzyl)-9-(2-hydroxyethoxymethyl) guanine | 8 | >20 |
| B.4335 | | |

TABLE 2-continued

| INACTIVATOR TYPE | I$_{50}$ ($\mu$M) hAT | T ½ (h) in PBS |
|---|---|---|
| O$^6$-(4-bromothenyl)-9-(2-hydroxy ethoxymethyl)guanine | See Table 3 | |
| 1E | | |
| B.4349 | | |
| O$^6$-(4-bromothenyl)-8-hydroxyguanine | See Table 3 | |
| O$^6$-(benzyl)-8-hydroxyguanine$^a$ | 0.3 | |
| 2A | | |
| B.4270 | | |
| O$^6$-(4-fluorobenzyl)-8-azaguanine | 0.08 | |
| B.4314 | | |
| O$^6$-(4-chlorothenyl)-8-azaguanine | See Table 3 | |
| B.4289 | | |
| O$^6$-(4-bromothenyl)-8-azaguanine | 0.045 | >10 |
| O$^6$-(benzyl)-8-azaguanine$^a$ | 0.07 | |
| 2B | | |
| B.4310 | | |
| O$^6$-(benzyl)-7-deaza-8-azaguanine | 0.01 | >16 |
| B.4340 | | |
| O$^6$-(4-fluorobenzyl)-8-aza-7-deazaguanine | 0.018 | >16 |
| B.4339 | | |
| O$^6$-(4-chlorobenzyl)-8-aza-7-deazaguanine | 0.02 | 1.5 |
| B.4343 | | |
| O$^6$-(piperonyl)-8-aza-7-deazaguanine | See Table 3 | |
| B.4348 | | |
| O$^6$-(furfuryl)-8-aza-7-deazaguanine | 0.036 | 0.27 |
| B.4338 | | |
| O$^6$-(thenyl)-8-aza-7-deazaguanine | 0.01 | |
| B.4337 | | |
| O$^6$-(4-bromothenyl)-8-aza-7-deazaguanine | 0.007 | >20 |
| 3A | | |
| B.4272 | | |
| O$^6$-(4-fluorobenzyl)-8-oxaguanine | See Table 3 | |
| B.4285 | | |
| O$^6$-(4-chlorobenzyl)-8-oxaguanine | 0.225 | 4.6 |
| B.4299 | | |
| O$^6$(4-chlorothenyl)-8-oxaguanine | 0.243 | 9.2 |
| B.4287 | | |
| O$^6$-(-4-bromothenyl)-8-oxaguanine | 0.24 | 2.6 |
| B.4232 | | |
| O$^6$-(benzyl)-8-oxaguanine | 0.25 | |
| 3B | | |
| B.4296 | | |
| O$^6$-(benzyl)-8-thiaguanine | 0.02 | >17 |
| B.4286 | | |
| O$^6$-(4-fluorobenzyl)-8-thiaguanine | 0.03 | >17 |
| B.4315 | | |
| O$^6$-(4-chlorothenyl)-8-thiaguanine$^c$ | 0.006 | |
| B.4351 | | |
| O$^6$-(4-bromothenyl)-8-thiaguanine | See Table 3 | |
| 3C | | |
| B.4290 | | |
| O$^4$-(4-fluorobenzyl)-pterin | 0.088 | >10 |
| B.4316 | | |
| O$^4$-(4-chlorothenyl)-pterin | See Table 3 | |
| B.4288 | | |
| O$^4$-(4-bromothenyl)-pterin | 0.025 | >10 |
| 4A | | |
| B.4305 | | |
| 2,4-diamino-6-(4-fluorobenzyloxy)pyrimidine | 4.0 | >16 |
| B.4304 | | |
| 2,4-diamino-6-(4-chlorobenzyloxy)pyrimidine | 5.0 | >16 |
| B.4303 | | |
| 2,4-diamino-6-(3,4-piperonyloxy)pyrimidine | 0.8 | 12.5 |
| B.4307 | | |
| 2,4-diamino-6-(thenyloxy)pyrimidine | 0.4 | 4.2 |
| B.4302 | | |
| 2,4-diamino-6-(4-chlorothenyloxy)pyrimidine | 0.17 | >16 |
| 2,4-diamino-6-(benzyloxy)pyrimidine$^a$ | 15 | |
| 4B | | |
| B.4301 | | |
| 2,4-diamino-6-(4-fluorobenzyloxy)-5-nitrosopyrimidine | 0.0175 | >16 |
| B.4311 | | |
| 2,4-diamino-(4-chlorothenyloxy)-5-nitrosopyrimidine | See Table 3 | |
| B.4312 | | |
| 2,4-diamino-6-(4-bromothenyloxy)-5-nitrosopyrimidine | 0.045 | 4 |
| 2,4-diamino-6-(benzyloxy)-5-nitrosopyrimidine$^a$ | 0.06 | |
| 4C | | |
| B.4306 | | |
| 2,4-diamino-6-(thenyloxy)-5-nitropyrimidine | 2.3 | >16 |
| B.4308 | | |
| 2,4-diamino-6-piperonyloxy-5-nitropyrimidine | 0.5 | 9.2 |
| 2,4-diamino-6-benzyloxy-5-nitropyrimidine$^a$ | 0.06 | |
| 4D | | |
| B.4380 | | |
| O$^2$(4-bromothenyl)-5-nitrocytosine | 50 | |
| 5 | | |
| B.4228 | | |
| S$^6$-(piperonyl)-6-thioguanine | 50 | |
| B.4352 | | |
| S$^6$-(4-bromothenyl)-6-thioguanine | 8 | |
| Comparative | | |
| B.4376 | | |
| O$^6$-thenyl-5-deazapterin | 1,600 | |

Results for some 9-substituted O$^6$(4-bromothenyl)guanines are included in Table 7.

$^a$Data taken from Chae et al, J. Med. Chem. 1995, 38, 359–365

$^b$Data taken from Moschel et al., J. Med. Chem. 1992, 35, 4486–4491.

$^c$B.4315 Raji I$_{50}$ (uM) 0.002

Blank Space = not done.

TABLE 3

| Inactivator | Mol Wgt | $I_{50}$ hAT ($\mu$M) | $I_{50}$ Raji ($\mu$M) | $I_{50}$ mAT ($\mu$M) | $I_{50}$ rAT ($\mu$M) | $I_{50}$ chAT ($\mu$M) | $I_{50}$ ogt ($\mu$M) | $I_{50}$ ada ($\mu$M) | $T_{1/2}$ (h) PBS | $T_{1/2}$ (h) by Assay | Raji cell sensitisation factor ($D_{50}$ control/$D_{50}$ 'B') BCNU Inactivator concentration ($\mu$M) 10 | TEMOZOLOMIDE 10 | 1.0 | 0.5 | 0.1 | Solubility in Water (mg/ml) | Raji cell toxicity at 10 $\mu$M 'B' alone (% Growth) |
|---|---|---|---|---|---|---|---|---|---|---|---|---|---|---|---|---|---|
| B4272 | 261 | 0.05 | 0.023 | 0.125 | 0.075 | 0.04 | >1000 | >1000 | 5.7 | 2.6 | 1.88 | 1.41 | — | — | — | 0.002 | 111.21 + 23.3 |
| B4311 | 286 | 0.009 | 0.009 | 0.008 | 0.016 | 0.02 | 1.8 | >1000 | 10 | 12.5 | 8.0 | 73.3 | 8.25 | — | 1.4 | 0 | 113.0 + 31.0 |
| B4314 | 283 | 0.011 | 0.012 | 0.073 | 0.037 | 0.03 | 2 | >1000 | >19 | >48 | 7.62 | 84 | 4.61 | — | 3.46 | Not done | 55.5 + 7.3 ($D_{50}$ 16 $\mu$M) |
| B4316 | 294 | 0.025 | 0.011 | 0.068 | 0.03 | 0.04 | 3.8 | >1000 | >19 | 32 | 6.4 | 66 | 13.2 | — | 1.4 | 0.3 | 85.5 + 20.0 |
| B4335 | 400 | 0.33 | 0.07 | 15.63 | 6.5 | 1.8 | 156 | >1000 | >19 | >48 | 5.33 | 38 | 3.5 | — | 1.0 | 0.009 | 98.4 + 12.2 |
| B4343 | 285 | 0.007 | 0.0085 | 0.31 | 0.045 | 0.02 | 30 | >1000 | 7.5 | 3 | 3.81 | 9.5 | 2.12 | — | 1.6 | 0.01 | 97.0 + 10.0 |
| B4349 | 342 | 0.018 | 0.007 | 0.043 | 0.074 | 0.02 | 0.08 | >1000 | 7.3 | >48 | 4.8 | 50.8 | 33 | — | 2.4 | 0.002 | 90.0 + 13.0 |
| B4351 | 344 | 0.003 | 0.005 | 0.071 | 0.027 | 0.03 | 5.8 | >1000 | >16 | 12 | 4.8 | 18.1 | 1.32 | — | 1.2 | Not done | 117.5 + 29.1 |
| BeG | 241 | 0.04 | 0.1 | 0.2 | 0.076 | 0.01 | 17 | >1000 | >64 | >75 | 4.33 | 27.5 | 1.89 | — | 1.03 | 0.023 | 82.2 + 11.0 |
| PaTrin-2 | 326 | 0.003 | 0.003 | 0.05 | 0.019 | 0.03 | 0.85 | >1000 | >16 | >48 | 6.0 | 60 | 33 | 8 | 5.5 | Not done | 69.8 + 10.3 |
| B.4280 | | | | | | | | | | | | | | | | | ($D50$ 44 $\mu$M) |

— = Not Done

TABLE 4

EFFECT OF INACTIVATOR PRETREATMENT ON SENSITISATION OF VAROUS HUMAN CANCER CELL LINES TO TEMOZOLOMIDE

| | SENSITISATION FACTOR ($D_{50}$ control/$L_{50}$ 'B') | | | | | | |
|---|---|---|---|---|---|---|---|
| | MCF-7 | PC3 | DU145** | RAJI | | | |
| INACTIVATOR | Inactivator dose (10 $\mu$M) | | | Inactivator dose ($\mu$M) | | | |
| | | | | 10 | 1.0 | 0.5 | 0.1 |
| B4311 | — | 5.56 | 3.75 | 73.3 | 8.25 | — | 1.4 |
| B4314* | — | 2.0 | 1.71 | 84.0 | 4.61 | — | 3.46 |
| B4316 | 8.0 | 7.6 | 3.53 | 66 | 13.2 | — | 1.4 |
| B4349 | 4.8 | 3.6 | 4.0 | 50.8 | 33.0 | — | 2.4 |
| BcG | 2.94 | 2.88 | 5.45 | 27.5 | 1.89 | — | 1.03 |
| PaTrin-2 | 3.13 | 4.6 | 4.14 | 60 | 33.0 | 8.0 | 5.5 |

*Toxic to Raji cells at 10 $\mu$M
**Sensitisation factor = $D_{60}$ control/$D_{60}$ 'B'
— Not done

TABLE 5

EFFECT OF INACTIVATOR PRETREATMENT ON SENSITISATION OF VARIOUS HUMAN CANCER CELL LINES TO BCNU

| | SENSITISATION FACTOR ($D_{50}$ control/$D_{50}$ 'B') | | | | | |
|---|---|---|---|---|---|---|
| INACTIVATOR (10 $\mu$M) | MCF-7 | PC3 | DU145** | RAJI | | |
| | | | | Inactivator dose ($\mu$M) | | |
| | | | | 10 | 1.0 | 0.1 |
| B4311 | — | 1.47 | 1.56 | 8.0 | — | — |
| B4314* | — | 1.46 | 1.25 | 7.62 | 7.6 | 3.45 |
| B4316 | 1.37 | 1.35 | 3.57 | 6.4 | — | — |
| B4349 | 1.85 | 1.63 | 2.78 | 4.8 | — | — |
| BcG | 1.94 | 1.41 | 1.79 | 4.33 | — | — |
| PaTrin-2 | 1.61 | 2.11 | 2.08 | 6.0 | — | — |

*Toxic to Raji cells at 10 $\mu$M
**Sensitisation factor = $D_{60}$ control/$D_{60}$ 'B'
— Not done

TABLE 6A

| Test No. | O⁶-Substiutent | Yield % (based on solvate) | Solvent for recrystn. | M.p. (decomp.) (° C.) | Formula | | C | H | N |
|---|---|---|---|---|---|---|---|---|---|
| B.4280 | 4-bromothenyl | 73 | MeOH | 204–205 | $C_{10}H_8BrN_5OS$ | Found | 36.7 | 2.45 | 21.46 |
| | | | | | | Req. | 36.82 | 2.47 | 21.47 |
| B 4281 | 5-chlorothenyl[a] | 39 | MeCN | 155–158 | $C_{10}H_8ClN_5OS$ | Found | 41.81 | 2.86 | 24.10 |
| | | | | | | Req. | 42.63 | 2.86 | 24.86 |
| B.4283 | 5-cyanothenyl[b] | 10 | MeOH | 200 upwards | $C_{11}H_8N_6OS$ 0.5 $H_2O$ | Found | 47.01 | 2.94 | 28.24 |
| | | | | | | Req. | 46.97 | 3.23 | 29.88 |
| B.4294 | 5-methylsulph-inylthenyl | 32 | MeOH | 200 upwards | $C_{11}H_{11}N_5O_2S_2$ | Found | 42.58 | 3.62 | 22.27 |
| | | | | | | Req | 42.71 | 3.58 | 22.64 |
| B.4298 | 4-chlorothenyl | 34 | MeCN | 194–198 | $C_{12}H_8ClN_5OS$ | Found | 42.70 | 2.94 | 24.84 |
| | | | | | | Req | 42.63 | 2.86 | 24.86 |
| B.4300 | 4-methoxythenyl | 44 | MeOH | 189–190 | $C_{11}H_{11}N_5O_2S$ | Found | 47.73 | 4.15 | 25.05 |
| | | | | | | Req | 47.64 | 4.00 | 25.26 |
| B.4313 | 5-bromo-3-thienylmethyl | 7.6 | MeCN | 190 upwards | $C_{10}H_2BrN_5OS$ | Found | 37.02 | 2.43 | 20.95 |
| | | | | | | Req | 36.82 | 2.47 | 21.47 |
| B.4317 | 4-cyanothenyl | 32 | MeOH | 213–216 | $C_{11}H_8N_6OS$ | Found | 48.50 | 2.84 | 30.66 |
| | | | | | | Req | 48.52 | 2.96 | 30.87 |
| B.4318 | 4,5-dichlorothenyl | 38 | MeOH | 210 upwards | $C_{10}H_7Cl_2N_5OS$. $1H_2O$ | Found | 35.94 | 2.67 | 20.96 |
| | | | | | | Req | 35.94 | 2.71 | 20.96 |
| B.4321 | 2-chloro-4-picolyl | 10 | MeOH | 234 upwards | $C_{11}H_9ClN_6O$ | Found | 47.15 | 3.52 | 29.32 |
| | | | | | | Req | 47.75 | 3.29 | 30.37 |
| B.4336 | 5-bromofurfuryl | 39 | MeOH | 180 upwards | $C_{10}H_8BrN_5O_2$. 0.25 $H_2O$ | Found | 38.22 | 2.71 | 21.93 |
| | | | | | | Req | 38.18 | 2.72 | 22.26 |

O⁶-Substituted guanines

| Compound, Test No. | O⁶-Substituted $RCH_2$ | Yield % | Solvent for Recrystn. | M.p. (decomp) (C.*) | Formula | Molecular Weight | | C | H | N |
|---|---|---|---|---|---|---|---|---|---|---|
| B.4282 | 3-picolyl N-oxide | 54 | MeOH | 244–254 | $C_{11}H_{10}N_6O_2$ | 258 | | | | |
| B.4309 | 5-methylsulphonyl-thenyl | 12 | EtOH | 206–209 | $C_{11}H_{11}N_5O_3S_2$. ½$C_2H_5OH$ | 348 | Found | 41.46 | 3.83 | 20.13 |
| | | | | | | | Req. | 41.37 | 4.05 | 20.10 |
| B.4319 | 6-chloro-3-picolyl | 58 | MeOH | >215 | $C_{11}H_9ClN_6O$. ½$H_2O$ | 285.7 | Found | 46.01 | 3.49 | 29.05 |
| | | | | | | | Req. | 46.25 | 3.53 | 29.42 |
| B.4320 | 5-bromo-3-picolyl | 56 | MeOH | >220 | $C_{11}H_9BrN_6O$. ½$H_2O$ | 330 | Found | 40.02 | 3.05 | 25.28 |
| | | | | | | | Req. | 39.87 | 3.01 | 25.28 |
| B.4354 | 4-isothiazolyl | 28 | MeOH | >200 | $C_9H_8N_6OS$. ¾$H_2O$ | 261.8 | Found | 41.59 | 3.64 | 31.53 |
| | | | | | | | Req. | 41.32 | 3.59 | 32.16 |
| B.4356 | 4-methylthiothenyl | 30 | MeOH | | $C_{11}H_{11}N_5OS_2$ | 293.4 | | | | |
| B.4357 | 5-iodo-3-thienyl-methyl | 23 | MeOH | >200 | $C_{10}H_8IN_5OS$ | 373 | | | | |
| B.4361 | 4-methyl-sulphonylthenyl | 95 | MeOH | 170–172 | $C_{11}H_{11}N_5O_3S_2$ | 325 | Found | 40.2 | 3.39 | 21.01 |
| | | | | | | | Req. | 40.61 | 3.41 | 21.53 |
| B.4366 | naphtho[2,1-b]-thiophen-2-yl-methyl | 81 | MeOH | >150 | $C_{18}H_{13}N_5OS$ | 347 | | | | |
| B.4373 | 4-azidothenyl | 37 | MeOH | >195[a] | $C_{10}H_8N_8SO$ | 288 | | | | |
| B.4377 | 4-methyl-sulphinylthenyl | 55 | MeOH | 204–206 | $C_{11}H_{11}N_5O_2S_2$ | 309 | | | | |
| B.4378 | 5-phenylthenyl | 54 | $CH_3CN$ | >170 | $C_{16}H_{13}N_5OS$ | 323 | | | | |

[a]5 6 mmol alcohol per mmol quaternary salt used in synthesis.
[b]Dimethylformamide reaction solvent.

TABLE 6B

| Test No. | O^c-Substituent | $\lambda_{max}$ (nm)(MeOH) | $\delta_H$ [ppm from TMS; $(CD_3)_2SO_1$] J (Hz) |
|---|---|---|---|
| B. 4280 | 4-bromothenyl | 238, 284 ($RCH_2OH$:233). | 5.65(s), 6.40(s), 7.37(d), 7.71(d), 7.85(s), 12.49(s). |
| B. 4281 | 5-chlorothenyl | 247, 284 ($RCH_2OH$:245). | 5.59(s), 6.40(s), 7.06(d), 7.22(d), 7.87(s), 12.47(bs). |
| B. 4283 | 5-cyanothenyl | 247, 272 | 5.73(s), 6.46(s), 7.49(d), 7.87(s), 7.92(d), 12.54(bs). |
| B. 4294 | 5-methylsulphinylthenyl | 243, 284(sh) [$RCH_2OH$:240, 274(sh)]. | 2.93(s), 5.73(s), 6.41(s), 7.40(d), 7.52(d), 7.88(s), 12.52(bs). |
| B. 4298 | 4-chlorothenyl | 238, 284 ($RCH_2OH$:240). | 5.64(s), 6.42(s), 7.34(d), 7.62(d), 7.86(s), 12.51(s) |
| B. 4300 | 4-methoxythenyl | 245(sh), 282 ($RCH_2OH$:258). | 3.75(s), 5.57(s), 6.37(s), 6.60(d), 7.01(d), 7.85(s), 12.48(s). |
| B. 4313 | 5-bromo-3-thienylmethyl | 240, 284 ($RCH_2OH$:236). | 5.42(s), 6.38(s), 7.40(d), 7.72(d), 7.85(s), 12.47(s). |

TABLE 6B-continued

| Compound Type, Test No. | RCH₂ | | |
|---|---|---|---|
| B. 4317 | 4-cyanothenyl | 244, 284 (RCH₂OH:244). | 5.68(s), 6.44(s), 7.74(d), 7.86(s), 8.60(d), 12.50(s). |
| B. 4318 | 4,5-dichlorothenyl | 243, 285 (RCH₂OH:243). | 5.58(s), 6.45(s), 7.41(s), 7.87(s), 12.52(s) |
| B. 4321 | 2-chloro-4-picolyl | 241, 272(sh), 285 [RCH₂OH:262, 268(sh)]. | 5.58(s), 6.36(s), 7.51(bs), 7.61(bs), 7.91(bs), 8.44(bs), 12.56(bs). |
| B. 4336 | 5-bromofurfuryl | 220, 284 (RCH₂OH: 223) | 5.42(s), 6.39(s), 6.64(d), 6.78(d), 7.85(s), 12.49(s). |

$O^6$-Substituted guanines

| Compound Type, Test No. | $O^6$-Substituent RCH₂ | $\lambda_{max}$ (MeOH) (nm) | $\delta_H$ [ppm from TMS, (CD₃)₂SO,]J (Hz) |
|---|---|---|---|
| B. 4282 | 3-picolyl N-oxide | 271 | 5.48(s), 6.41(s), 7.47(m), 7.87(s), 8.22(m), 8.42(s), 12.52(s) |
| B. 4309 | 5-methylsulphonyl-thenyl | 242, 284 | 5.75(s), 6.43(s), 7.47(d), 7.74(d), 7.87(s), 12.52(s). |
| B. 4319 | 6-chloro-3-picolyl | 242, 276 | 5.53(s), 6.38(s), 7.59(d), 7.87(s), 8.05(dd), 8.64(d), 12.48(s) |
| B. 4320 | 5-bromo-3-picolyl | 242, 281 | 5.53(s), 6.41(s), 7.86(s), 7.86(s), 8.26(dd), 8.73(d), 8.78(d), 12.50(s). |
| B. 4354 | 4-isothiazolyl | 244, 284 | 5.58(s), 6.41(s), 7.84(s), 8.81(s), 9.22(s), 12.47(s) |
| B. 4356 | 4-methylthio-thenyl | 236, 283 | 2.48(s), 5.62(s), 6.40(s), 7.26(m), 7.85(s), 12.48(s). |
| B. 4357 | 5-iodo-3-thienylmethyl | 240, 283 | 5.43(s), 6.38(s), 7.48(s), 7.77(s), 7.84(s), 12.47(s). |
| B. 4361 | 4-methylsulphonyl-thenyl | 240, 285 | 3.26(s), 5.70(s), 6.40(s), 7.72(s), 7.85(s), 8.38(d), 12.49(s). |
| B. 4366 | naphtho[2,1-b]-thiophen-2-ylmethyl | 244, 286 sh 295, 306 sh | 5.90(s), 6.47(s), 7.60(t), 7.69(t), 7.86(t), 8.04(dd), 8.44(s), 8.51(d), 12.51(s). |
| B. 4373 | 4-azidothenyl | 227, 280 | 5.64(s), 6.36(s), 7.20(s), 7.28(s), 7.84(s), 12.47(s). |
| B. 4377 | 4-methylsulphinyl-thenyl | 241, 285 | 2.82(s), 5.68(s), 6.33(s), 7.60(s), 7.82(s), 8.01(s), 12.45(s). |
| B. 4378 | 5-phenylthenyl | 244 sh, 289 | 5.57(s), 6.32(s), 7.31(m), 7.41(m), 7.41(m), 7.63(d), 7.82(s), 12.43(s). |

TABLE 7

| INACTIVATOR | M.Wt | $I_{50}$ (μM) hAT | Raji $I_{50}$ (μM) | Stability T ½(h) By Spec |
|---|---|---|---|---|
| B.4280 | | | | |
| $O^6$-(4-bromothenyl)guanine | 326 | 0.0034 | | |
| B.4281 | | | | |
| $O^6$-(5-chlorothenyl)guanine | 281.7 | 0.004 | | >10 |
| B.4282 | | | | |
| $O^6$-(oxido-3-picolyl)guanine | 276 | 1.4 | | >20 |
| B.4283 | | | | |
| $O^6$-(5-cyanothenyl)guanine | 272 | 0.005 | | >20 |
| B.4294 | | | | |
| $O^6$-(5-methylsulphinylthenyl)guanine | 309 | 0.03 | | >10 |
| B.4298 | | | | |
| $O^6$-(4-chlorothenyl)guanine | 282 | 0.008 | 0.005 | >16 |
| B.4300 | | | | |
| $O^6$-(4-methoxythenyl)guanine | 277 | 0.0165 | | 0.83 |
| B.4309 | | | | |
| $O^6$-(5-methylsulphonylthenyl)guanine | 325 | 0.072 | | >16 |
| B.4313 | | | | |
| $O^6$-(5-bromo-3-thienylmethyl)guanine | 326 | 0.0065 | 0.035 | |
| B.4317 | | | | |
| $O^6$-(4-cyanothenyl)guanine | 272 | 0.0028 | | >19 |
| B.4318 | | | | |
| $O^6$-(4,5-dichlorothenyl)guanine | 348 | 0.015 | | 2.5 |

TABLE 7-continued

| INACTIVATOR | M.Wt | I$_{50}$ (μM) hAT | Raji I$_{50}$ (μM) | Stability T ½(h) By Spec |
|---|---|---|---|---|
| B.4319 | | | | |
| O$^6$-(6-chloro-3-picolyl)guanine | 277 | 0.2 | | >13 |
| B.4320 | | | | |
| O$^6$-(5-bromo-3-picolyl)guanine | 321 | 0.25 | | >13 |
| B.4321 | | | | |
| O$^6$-(2-chloro-4-picolyl)guanine | 277 | 0.04 | | >16 |
| B.4336 | | | | |
| O$^6$-(5-bromofurfuryl)guanine | 310 | 0.02 | | 0.32 |
| B.4354 | | | | |
| O$^6$-(4-isothiazolylmethyl)guanine | 248 | 0.07 | | |
| B.4356 | | | | |
| O$^6$-(4-methylthiothenyl)guanine | 293 | 0.0095 | | |
| B.4357 | | | | |
| O$^6$-(5-iodo-3-thienylmethyl)guanine | 447 | 0.009 | | >16 |
| B.4361 | | | | |
| O$^6$-(4-methylsulphonylthenyl)guanine | 325 | 0.2 | | >16 |
| B.4366 | | | | |
| O$^6$-(naphtho[2,1-b]thiophen-2-ylmethyl)guanine | 347 | 0.05 | | |
| B.4368 | | | | |
| 9-(B-D-arabinofuranosyl)-O$^6$-(4-bromothenyl)guanine | 458 | 0.115 | | |
| B.4369 | | | | |
| O$^6$-(4-bromothenyl)-9-(ethoxymethyl)guanine | 384 | 0.28 | | |
| B.4370 | | | | |
| O$^6$-(4-bromothenyl)-9(octyloxymethyl)guanine | 468 | 1.2 | | |
| B.4373 | | | | |
| O$^6$-(4-azidothenyl)guanine | 288 | 0.0063 | | |
| B.4377 | | | | |
| O$^6$-(4-methylsulphinylthenyl)guanine | 309 | 0.15 | | |
| B.4378 | | | | |
| O$^6$(5-phenylthenyl)guanine | 323 | 0.75 | | |
| B.4379 | | | | |
| O$^6$-(4-bromothenyl)-2-deoxyguanosine | 442 | 0.095 | | |

TABLE 7B

| INACTIVATOR | M.Wt | In vitro I$_{50}$ (μM) | | | | | Raji I$_{50}$ | Stability T ½(h) (μM) | |
| | | hAT | mAT | rAT | chAT | agt | | By Spec | By Assay |
|---|---|---|---|---|---|---|---|---|---|
| B.4363 | | | | | | | | | |
| O$^6$-(4-bromothenyl)guanosine | 458 | 0.08 | | 0.24 | 0.95 | 30 | >16 | >48 | |

Blank space = not done

TABLE 8

ATASE ACTIVITY IN VARIOUS TISSUES OF NU/NU MICE AFTER TREATMENT WITH 10 mg/kg (IP) B.4280
MEAN ACTIVITY (fm/mg)

| Tissue | 24 h | 48 h | Control* |
|---|---|---|---|
| Tumour | 36 ± 7.79 | 140 ± 43.87 | 125 |
| Liver | 89.7 ± 10.14 | 100.7 ± 8.73 | 110** |
| Lung | 15.3 ± 2.05 | 24 ± 2.83 | 43 |
| Kidney | 24.3 ± 4.03 | 28.7 ± 4.11 | 33 |
| Spleen | 41 ± 5.35 | 68.3 ± 9.53 | 81 |
| Brain | 13.7 ± 2.05 | 16.3 ± 1.25 | 14 |
| Testis | 45 ± 7.48 | 44 ± 1.41 | 45 |
| Bone Marrow (pooled) | 42 | 61 | 30 |

*control values taken from a separate experiment
**mean of 2 control liver values
Table 8.
Effect of B.4280 on ATase activity in several tissues of nude mice. Animals were given a single dose of B.4280 (10 mg/kg i.p.) and sacrificed 24 or 48 hours later.

TABLE 9

TOXICITY OF INACTIVATORS IN COMBINATION WITH BCNU IN DBA$_2$ MICE

| | % SURVIVAL AFTER 14 DAYS | | |
|---|---|---|---|
| INACTIVATOR (60 mg/kg) | 20 mg/kg BCNU | 16 mg/kg BCNU | 12 mg/kg BCNU |
| O$^6$-benzylguanine | 33 (2/6) | 0 (0/6)* | 50 (3/6)** |
| B.4205 | 0 (0/6) | 50 (3/6)* | 100 (6/6)** |
| B.4280 | 93 (14/15) | 100 (15/15) | 100 (15/15) |

*15 mg/kg BCNU
**10 mg/kg BCNU
All agents were given as a single i.p. dose
Table 9
Effect of ATase inactivators on the acute toxicity of bis-chloroethylnitrosourea (BCNU) in DBA$_2$ mice.

REFERENCES

1. Kiburis J. and Lister, J. H. *J. Chem. Soc.* (C), 1971, 3942.
2. Robins R. K., Jones, J. W. and Lin, H. H., *J. Org. Chem.* 21 1956, 695.
3. Robins R. K., and Robins, M. J. *J. Org. Chem.,* 34 1969, 2163.
4. Robins, M. J. and Hatfield, P. W., *Canad J. Chem.,* 60, 1982, 547.
5. Dolan, M. E., Chac, M. -Y., Pegg, A. E., Mullen, J. H., Friedman, H. S. and Moschel, R. C. *Cancer Res.,* 54, 1994, 5123.
6. Shealy, Y. F., Clayton, J. D., O'Dell, G. A. and Montgomery, J. A., *J. Org. Chem.,* 27, 1962, 4518.
7. Seela, F., Steker, H., Driller, H. and Bindig, U., *Liebigs Ann. Chem.,* 1987, 15.
8. Boyle, P. H. and Lockhart, R. J., *Tetrahedron,* 40, 1984, 879.
9. Kresze, G. and Wucherplennig, W., *Newer Methods of Preparative Organic Chemistry* (W. Foerst, ed.), Academic Press, New York, 1968, vol. 5, p.115; Shealy, Y. F., Clayton, J. D. and Montgomery, J. A., *J. Org. Chem.,* 27, 1962, 2154.
10. Baudy, R. B., Greenblatt, L. P. et al., *J. Med. Chem.,* 36, 1993, 331.
11. O'Brien, D. E. Cheng, C. C. and Pfleiderer, W., *J. Med. Chem.,* 9 1966, 573; Rokos, H. and Pfleiderer, W., *Chem. Ber.,* 104, 1971, 739.
12. M. D. Dowle, R. Hayes, D. B. Judd and C. N. Williams, *Synthesis,* 1983, 73.
13. E. Campaigne and W. L. Archer, *J. Amer. Chem. Soc.,* 75, 1953, 989.
14. J. Cymerman-Craig and J. W. Loder, *J. Chem. Soc.,* 1954, 327.
15. C. R. Johnson and J. E. Keiser, *Org. Synth. Coll.* Vol. 5. 1973, 791.
16. I. L. Cairns and B. C. McKusick, *J. Org. Chem.,* 15, 1950, 790.
17. Z. N. Nazarova, *Zhur. Obshch. Khim.,* 24, 1954, 575 (*Chem. Abs.,* 49, 6214, 10262; 53, 15047).
18. W. J. Chute, W. M. Orchard and G. F. Wright, *J. Org. Chem.,* 6, 1941, 157.
19. J. Iriarte, E. Martinez and J. M. Muchowski, *J. Heterocycl. Chem.,* 13, 1976, 393.
20. P. Fournari, R. Guilard and M. Person, *Bull. Soc. Chim. France,* 1967, 4115.
21. S. Conde, R. Madronero, M. P. Fernandez-Tome and J. del Rio, *J. Med. Chem.,* 21, 1978, 978.
22. E. Profft and D. Gerber, *J. Prakt. Chem.,* 16, 1962, 18.
23. Farbwerke Hoechst A. -G., Brit. Pat.1127,064 1968 (*Chem. Abs.,* 70, 47284f).
24. P. Dubus, B. Decroix, J. Morel and P. Pastour, *Bull. Soc. Chim. France,* 1976, 628.
25. P. J. Newcombe and R. K. Norris, Austral. *J. Chem.,* 34, 1981, 1879.
26. P. R. Huddleston, J. M. Barker, B. Stickland, M. L. Wood and L. H. M. Guindi, *J. Chem. Research,* 1988(S) 240, (M) 1871.
27. M. Hamana and M. Yamazaki, *J. Pharm. Soc.* Japan, 81, 1961. 574 (*Chem. Abs.* 55, 24743).
28. F. E. Ziegler and J. G. Sweeny, *J. Org. Chem.,* 34, 1969, 3545.
29. C. R. de Wet and P. A. de Villiers, *Tydskr. Natuurwet.,* 14, 1974, 70 (*Chem. Abs.* 84, 30822w).
30. Fan, C. -Y., Potter, P. M., Rafferty, J. A., Watson, A. J., Cawkwell, I., Searle, P. F., O'Connor, P. J. and Margison, G. P. (1991) *Nucleic Acids Res.* 18, 5723–5727
31. Wilkinson, M. D., Potter, P. M., Cawkwell, L., Georgiadis, P., Patel, D., Swann, P. F. and Margison, G. P. (1989) *Nucleic Acids Res.* 17, 8475–8484.
32. Wilkinson, M. C., Cooper, D. P., Southan, C., Potter, P. M. & Margison, G. P. (1990) *Nucleic Acids Res.,* 18, 13–16.
33. R. Bernetti, F. Mancini and C. C. Price, *J. Org. Chem.* 27, 1962, 2863.
34. M. T. G. Ivery and J. E. Gready, *J. Heterocycl. Chem.,* 31, 1994, 1385.
35. A. Albert, D. J. Brown and G. Cheesman, *J. Chem. Soc.,* 1951, 474.
36. M. J. Robins and B. Uznanski, Can. *J. Chem.,* 59, 1981, 2601.
37. B. Zajc, M. K. Lakshman, J. M. Sayer and D. M. Jerina, *Tetrahedron Lett.,* 33, 1992, 3409.
38. N. B. Hanna, K. Ramasamy, R. K. Robsins and G. R. Revankar, *J. Heterocycl. Chem.,* 25, 1988, 1899.

What is claimed is:

1. A pyrimidine derivative selected from

A) 6-hetarylalkyloxy pyrimidine derivatives of formula II

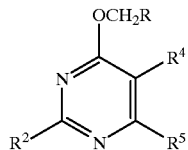

wherein
R is a cyclic group having at least one 5- or 6-membered hetercyclic ring, or a substituted 5- or 6-membered heterocyclic ring, optionally with a carbocyclic, substituted carbocyclic, heterocyclic or substituted heterocyclic ring fused thereto, the or each heterocyclic ring or substituted heterocyclic ring having at least one hetero atom chosen from O, N or S;
$R^2$ is selected from H, $C_1$–$C_5$ alkyl, halogen or $NH_2$,
$R^4$ and $R^5$ which are the same or different are selected from H, NH—Y' or $NO_n$ wherein
Y' is H, ribosyl, deoxyribosyl, arabinosyl,

wherein X is O or S, R" is alkyl or substituted alkyl and R''' is H, alkyl, or substituted alkyl,
n–1 or 2, or
$R^4$ and $R^5$ together form a ring structure $III^a$

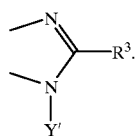

wherein
Y' is as defined above,
$R^3$ is H or OH, or
$R^4$ and $R^5$ together with the pyrimidine ring form a 5- or 6-membered ring structure containing one or more hetero atoms other than that of formula $III^a$ above; and pharmaceutically acceptable salts thereof,
with the proviso that $R^2$ is not $NH_2$ if $R^4$ and $R^5$ form a ring structure IX

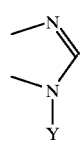

wherein Y is H, ribosyl, deoxyribosyl, or

wherein X is O or S, R" and R''' are alkyl or substituted alkyl;
and with the further proviso that R is not a cyclic group having a heterocyclic ring with more than one S atom in the ring; and B) 6-arylalkyloxy pyrimidine derivatives selected from those of formulae $III^b$, $III^c$, $IV^b$, $V^b$, $VI^b$, $VII^b$, and $VIII^b$ as defined below:

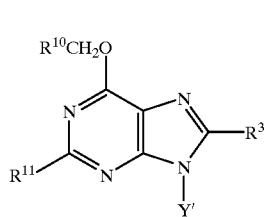

wherein
$R^{10}$ is phenyl or substituted phenyl;
$R^{11}$ is $C_1$–$C_5$ alkyl;
Y' is as defined above;
$R^3$ is H or OH;

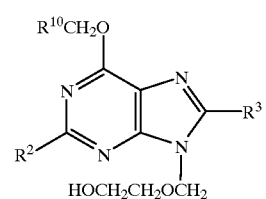

wherein
$R^{10}$ is as defined above;
$R^2$ is as defined for formula II;
$R^3$ is H or OH;

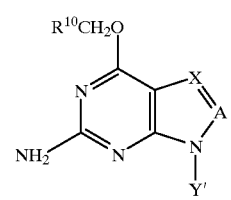

wherein
$R^{10}$ is as defined above;
Y' is as defined for formula II;
X is CH or N;
provided that if X is N and Y is H, then $R^{10}$ is not phenyl;

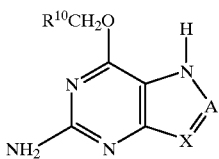

wherein
R¹⁰ is as defined above;
X is CH or N;
A is CH or N;

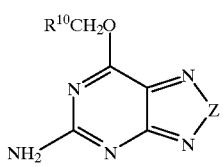

wherein
R¹⁰ is as defined above;
Z is O or S or CH=CH;

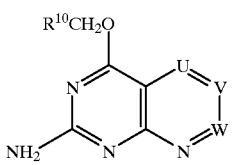

wherein
R¹⁰ is as defined above;
U is CH or N;
V is CH or N;
W is CH or N;

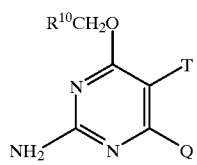

wherein
R¹⁰ is as defined above;
T is H, NH₂ or NO_n wherein n–1 or 2;
Q is H, NH₂ or HO_n wherein n=1 or 2;
provided that
: if Q is NH₂ and T is NO or NO₂, or
: if Q is H and T is NO₂, or
: if Q and T are both NH₂, or
: if Q is NH₂, and T is H, then
R¹⁰ is not phenyl.

2. A compound according to claim 1 which is of Formula IV

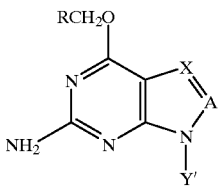

wherein:
R and Y' are as defined in claim 1;
X is CH or N;
A is CH or N;
provided that if X is N and A is CH, Y' is not H, ribosyl, deoxyribosyl, or

wherein X is O or S, R" and R"' are alkyl or substituted alkyl.

3. A compound according to claim 1 wherein R is a 5-membered heterocyclic ring, or a substituted 5-membered heterocyclic ring, having at least one S atom therein.

4. A compound according to claim 1 wherein R is a member selected from the group consisting of a thiophene ring, a substituted thiophene ring, a furan ring and a substituted furan ring.

5. A compound according to claim 1 wherein R is a cyclic group having at least one 5- or 6-membered heterocyclic ring, optionally with a carbocyclic or heterocyclic ring fused thereto, wherein the heterocyclic or carbocyclic ring is substituted by halo, haloalkyl, cyano, SO_nR⁷ where R⁷ is alkyl and n=0, 1 or 2, or —COOR⁸ wherein R⁸ is alkyl.

6. A compound according to claim 1 wherein R is a member selected from the group consisting of a thiophene ring, a bromo-substituted thiophene ring, a cyano-substituted thiophene ring a furan ring, a bromo-substituted furan ring and a cyano-substituted furan ring.

7. A compound according to claim 1 wherein R is a member selected from the group consisting of a thiophene ring and a furan ring with a chloro-, bromo- or cyano-substituent in a 1,3- or 1,4-relationship with the methyleneoxy group attached to the pyrimidine residue.

8. A compound according to claim 1 wherein Y' is alkoxymethyl optionally substituted with OH on the alkyl of the alkoxy group.

9. Guanine derivatives of formula XIII

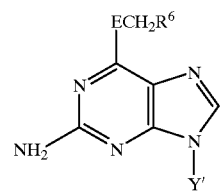

wherein
E is O or S,

Y' is H, ribosyl, deoxyribosyl, arabinosyl,

wherein X is O or S, R" is alkyl or substituted alkyl and R"' is H, alkyl, or substituted alkyl, $R^6$ is a cyclic group having at least one 5- or 6-membered heterocyclic ring, or a substituted 5- or 6-membered heterocyclic ring, optionally with a carbocyclic, substituted carbocyclic, heterocyclic or substituted heterocyclic ring fused thereto, the or each heterocyclic ring or substituted heterocyclic ring having at least one hetero atom chosen from O, N or S;

and pharmaceutically acceptable salts thereof, with the proviso that the following compounds are disclaimed;
$O^6$-thenylguanine,
$O^6$-(3-thienylmethyl)guanine,
$O^6$-piperonylguanine,
$O^6$-furfurylguanine,
$O^6$-(3-furylmethyl)guanine,
$O^6$-(2-benzo[b]thienylmethyl)guanine,
$O^6$-(2-benzofuranylmethyl)guanine,
$O^6$-(5-thiazolylmethyl)guanine,
$O^6$-(5-methoxycarbonylfurfuryl)guanine,
$O^6$-(5-bromothenyl)guanine,
$O^6$-(5-cyanofurfuryl)guanine,
$O^6$-(2-benzo[b]thienylmethyl)guanosine,
$O^6$-(4-picolyl)guanine,
$O^6$-(2-naphthylmethyl)guanine, and with the further proviso that $R^6$ is not a cyclic group having a heterocyclic ring with more than one S atom in the ring.

10. A compound according to claim 9 wherein $R^6$ is a 5-membered heterocyclic ring or a substituted 5-membered heterocyclic ring having at least one S atom therein.

11. A compound according to claim 9 wherein $R^6$ is a member selected from the group consisting of a thiophene ring, a substituted thiophene ring, a furan ring and a substituted furan ring.

12. A compound according to claim 9 wherein $R^6$ is a cyclic group having at least one 5- or 6-membered heterocyclic ring, optionally with a carbocyclic or heterocyclic ring fused thereto, wherein the heterocyclic or carbocyclic ring is substituted by halo, haloalkyl, cyano, $SO_nR^7$ where $R^7$ is alkyl and n=0, 1 or 2, or —$COOR^8$ wherein $R^8$ is alkyl.

13. A compound according to claim 9 wherein $R^6$ is a member selected from the group consisting of a thiophene ring, a bromo-substituted thiophene ring, a cyano-substituted thiophene ring, a furan ring, a bromo-substituted furan ring and a cyano-substituted furan ring.

14. A compound according to claim 9 wherein $R^6$ is a member silected from the group consisting of a thiophene ring and a furan ring with a chloro-, bromo- or cyano-substituent in a 1,3- or 1,4-relationship with the methyleneoxy group attached to the purine ring.

15. Guanine derivatives of formula XIV:

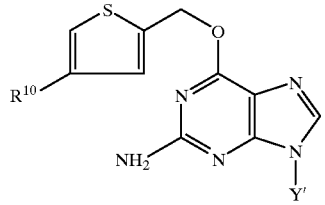

XIV wherein $R^{10}$ is bromo, chloro or cyano, and Y' is H, ribosyl, deoxyribosyl, arabinosyl,

wherein X is O or S, R" is alkyl or substituted alkyl and R"' is H, alkyl, or substituted alkyl.

16. A compound according to claim 15 wherein Y' is H, ribosyl, deoxyribosyl, or

wherein X is O or S, R" is alkyl or substituted alkyl, and R"' is H, alkyl, or substituted alkyl.

17. A compound according to claim 13 which is a member selected from the group consisting of:
$O^6$-(4-methylthiothenyl)guanine, and
$O^6$-(4-azidothenyl)guanine.

18. A pharmaceutical composition comprising a compound according to claim 1 and a pharmaceutically acceptable excipient.

19. A pharmaceutical composition according to claim 18 further comprising an alkylating agent.

20. A composition according to claim 19 wherein the alkylating agent is a member selected from the group consisting of 1,3bis(2-chloroethyl)-1-nitrosourea (BCNU) and temozolomide.

21. A method for depleting $O^6$-alkylguanine-DNA alkyltransferase activity in a host comprising:
administering to the host an effective $O^6$-alkylguanine-DNA alkyltransferase activity depleting amount of a composition according to claim 18.

22. A method for treating tumour cells in a host comprising:
administering to the host a composition comprising an inactivator compound according to claim 1 in an amount effective to deplete $O^6$-alkylguanine-DNA alkyltransferase activity sufficiently to enhance the effectiveness of a chemotherapeutic alkylating agent; and
administering to the host a composition comprising an alkylating agent in an amount which is effective in combination with the said inactivator compound for treating said tumour cells.

23. $O^6$-(methylene[$^3$H]-(4-bromothenyl)guanine.

24. A compound according to claim 22 which is a member selected from the group consisting of:
$O^6$-(4-bromothenyl)-9-(2-hydroxyethoxymethyl)guanine,
9(β-D-arabinofuranosyl)-$O^6$-(4-bromothenyl)guanine,
$O^6$-(4-bromothenyl)guanosine, $O^6$-(4-bromothenyl)-2-deoxyguanosine, $O^6$-(4-bromothenyl)-9-(ethoxymethyl)guanine, and $O^6$-(4-bromothenyl)-9-(octyloxymethyl)guanine.

25. A pharmaceutical composition comprising a compound according to claim 9 and a pharmaceutically acceptable excipient.

26. A pharmaceutical composition comprising a compound according to claim 15 and a pharmaceutically acceptable excipient.

27. A method for treating tumour cells in a host comprising:

administering to the host a composition comprising an inactivator compound according to claim 9 in an amount effective to deplete $O^6$-alkylguanine-DNA alkyltransferase activity sufficiently to enhance the effectiveness of a chemotherapeutic alkylating agent; and administering to the host a composition comprising an alkylating agent in an amount which is effective in combination with the said inactivator compound for treating said tumour cells.

28. A method for treating tumour cells in a host comprising:

administering to the host a composition comprising an inactivator compound according to claim 22 in an amount effective to deplete $O^6$-alkylguanine-DNA alkyltransferase activity sufficiently to enhance the effectiveness of a chemotherapeutic alkylating agent; and administering to the host a composition comprising an alkylating agent in an amount which is effective in combination with the said inactivator compound for treating said tumour cells.

29. A compound according to claim 9 wherein Y' is alkoxymethyl optionally substituted with OH on the alkyl of the alkoxy group.

30. A compound according to claim 15 wherein Y' is alkoxymethyl optionally substituted with OH on the alkyl of the alkoxy group.

31. A compound according to claim 29 wherein Y' is alkoxymethyl having 1 to 10 carbon atoms in the alkoxy group and optionally substituted with OH on the alkyl of the alkoxy group.

32. A compound according to claim 30 wherein Y' is alkoxymethyl having 1 to 10 carbon atoms in the alkoxy group and optionally substituted with OH on the alkyl of the alkoxy group.

33. A compound according to claim 29 wherein Y' is hydroxyalkoxymethyl other than hydroxyethoxymethyl.

34. A compound according to claim 29 wherein Y' is hydroxyalkoxymethyl other than hydroxyethoxymethyl.

* * * * *